(12) United States Patent
Berezin et al.

(10) Patent No.: US 9,359,405 B2
(45) Date of Patent: Jun. 7, 2016

(54) ANTAGONISTS OF THE INTERLEUKIN-1 RECEPTOR

(75) Inventors: Vladimir Berezin, Copenhagen N (DK); Elisabeth Bock, Charlottenlund (DK)

(73) Assignee: Phlogo ApS, Hellerup (DK)

( * ) Notice: Subject to any disclaimer, the term of this patent is extended or adjusted under 35 U.S.C. 154(b) by 60 days.

(21) Appl. No.: 14/003,824

(22) PCT Filed: Mar. 14, 2012

(86) PCT No.: PCT/DK2012/000022
§ 371 (c)(1),
(2), (4) Date: Nov. 22, 2013

(87) PCT Pub. No.: WO2012/122985
PCT Pub. Date: Sep. 20, 2012

(65) Prior Publication Data
US 2014/0073556 A1   Mar. 13, 2014

(30) Foreign Application Priority Data

Mar. 14, 2011  (DK) ................................ 2011 70120

(51) Int. Cl.
| | | |
|---|---|---|
| C07K 7/08 | (2006.01) | |
| A61K 38/00 | (2006.01) | |
| C07K 14/54 | (2006.01) | |
| C07K 14/545 | (2006.01) | |
| C07K 7/06 | (2006.01) | |

(52) U.S. Cl.
CPC . *C07K 7/08* (2013.01); *A61K 38/00* (2013.01); *C07K 7/06* (2013.01); *C07K 14/54* (2013.01); *C07K 14/545* (2013.01)

(58) Field of Classification Search
None
See application file for complete search history.

(56) References Cited

U.S. PATENT DOCUMENTS

| | | | |
|---|---|---|---|
| 5,075,222 A | 12/1991 | Hannum et al. | |
| 5,739,282 A | 4/1998 | Colotta et al. | |
| 6,159,460 A | 12/2000 | Thompson et al. | |
| 6,599,873 B1 | 7/2003 | Sommer et al. | |
| 6,858,409 B1 | 2/2005 | Thompson et al. | |
| 7,430,476 B2 * | 9/2008 | Carr et al. .................. | 702/19 |
| 7,482,323 B2 | 1/2009 | Hasty et al. | |
| 7,619,066 B2 | 11/2009 | Raibekas et al. | |
| 7,674,464 B2 | 3/2010 | Hasty et al. | |
| 2003/0083301 A1 | 5/2003 | Perez-Polo et al. | |
| 2004/0029179 A1 * | 2/2004 | Koentgen .................. | 435/7.1 |
| 2004/0076991 A1 * | 4/2004 | Carr et al. ................. | 435/6 |
| 2005/0159590 A1 | 7/2005 | Rotman et al. | |
| 2005/0260159 A1 | 11/2005 | Hasty et al. | |
| 2006/0094663 A1 | 5/2006 | Chemtob et al. | |
| 2007/0027082 A1 | 2/2007 | Hasty et al. | |
| 2008/0193382 A1 | 8/2008 | Rock et al. | |
| 2010/0041609 A1 | 2/2010 | Chemtob et al. | |
| 2010/0239554 A1 * | 9/2010 | Schellenberger et al. ... | 424/94.3 |

FOREIGN PATENT DOCUMENTS

| | | | |
|---|---|---|---|
| WO | WO 89/11540 | | 11/1989 |
| WO | WO 96/09323 | | 3/1996 |
| WO | WO 00/64938 | * | 4/2000 |
| WO | WO 2005/086695 A2 | | 9/2005 |
| WO | WO 2005/105830 A1 | | 11/2005 |
| WO | WO 2007/004060 A2 | | 1/2007 |
| WO | WO 2009/025763 A2 | | 2/2009 |
| WO | WO 2009/048961 A1 | | 4/2009 |

OTHER PUBLICATIONS

UniProt P18510—IL1RA_HUMAN, Nov. 1, 1990.*
Chang et al., "Modulation of Neuroimmune Responses on Glia in the Central Nervous System: Implication in Therapeutic Intervention against Neuroinflammation," Cellular & Molecular Immunology, vol. 6, No. 5, pp. 317-326 (2009).
Cawthorne et al., "Biodistribution, pharmacokinetics and metabolism of interleukin-1 receptor antagonist (IL-1RA) using [18F]-IL1RA and PET imaging in rats," British Journal of Pharmacology Research Paper, pp. 659-672 (2011).
Clark et al., "Interleukin-1 receptor antagonist penetrates human brain at experimentally therapeutic concentrations," Journal of Cerebral Blood Flow & Metabolism, pp. 387-394 (2008).
Dahlen et al., "Development of Interleukin-1 Receptor Antagonist Mutants with Enhanced Antagonistic Activity In Vitro and Improved Therapeutic Efficacy in Collagen-Induced Arthritis," Journal of Immunotoxicology, 5:189-199, (2008).
Dinarello, "blood Biologic basis for interleukin-1 in disease," The Journal of The American Society of Hematology, vol. 87, No. 6, pp. 2095-2147 (1996).
Ditlevsen et al., "The role of phosphatidylinositol 3-kinase in neural cell adhesion molecule-mediated neuronal differentiation and survival," Journal of Neurochemistry, vol. 84, pp. 546-556 (2003).
Gabay et al., "IL•1 pathways in inflammation and human diseases," Nature Reviews Rheumatology, vol. 6, pp. 232-241 (2010).
Galea et al., "Intravenous anakinra can achieve experimentally effective concentrations in the central nervous system within a therapeutic time window: results of a dose-ranging study," Journal of Cerebral Blood Flow & Metabolism, vol. 31, pp. 439-447 (2011).
Hallegua et al., "Potential therapeutic uses of interleukin 1 receptor antagonists in human diseases," Annals of the Rheumatic Diseases, The Eular Journal, vol. 61, pp. 960-967 (2002).

(Continued)

*Primary Examiner* — Christina Bradley
(74) *Attorney, Agent, or Firm* — Postemak Blankstein & Lund LLP

(57) ABSTRACT

The present invention discloses novel peptides derived from the IL-1 receptor antagonist protein (IL1 RA), capable of binding to the cell surface IL-1 receptor 1 (IL1 R1) and interfere with the binding of IL-1 to IL1 R1. This binding thus effectively antagonizes the inflammatory effects of IL-1, such as by reducing TNF-alpha secretion from macrophages. This is of potential use as an anti-inflammatory factor throughout the human body, including the central nervous system. The use of said peptides as anti-inflammatory agents for treatment of pathological conditions wherein IL-1 plays a prominent role, such as inflammatory conditions of the body and the central nervous system, is thus an aspect of the present invention.

20 Claims, 33 Drawing Sheets

(56) References Cited

OTHER PUBLICATIONS

Heneka et al., "Neuroinflammatory processes in Alzheimer's disease," Journal of Neural Transmission, vol. 117, pp. 919-947 (2010).

Kluczyk et al., "Immunomodulatory Activity of Oligopeptides Related to Interleukin 1 Receptor Antagonist Sequence," Archivum Immunologiae et Therapiae Experimentalis, vol. 45, pp. 427-433 (1997).

Kluczyk et al., "The "two-headed" peptide inhibitors of interleukin-1 action," Peptides, vol. 21, Issue 9, pp. 1411-1420 (2000).

Koprich et al., "Neuroinflammation mediated by IL-1β increases susceptibility of dopamine neurons to degeneration in an animal model of Parkinson's disease," Journal of Neuroinflammation, 5:8, (2008).

Krause et al., "Neuroinflammation, Microglia and Implications for Anti-Inflammatory Treatment in Alzheimer's Disease," International Journal of Alzheimer's Disease, vol. 2010, Issue 732806, pp. 1-9 (2010).

Massoud et al., "Update on the Pharmacological Treatment of Alzheimer's Disease," Current Neuropharmacology, vol. 8, No. 1, pp. 69-80 (2010).

Neiiendam et al., "An NCAM-derived FGF-receptor agonist, the FGL-peptide, induces neurite outgrowth and neuronal survival in primary rat neurons," Journal of Neurochemistry, vol. 91, pp. 920-935 (2004).

Relton et al., "Interleukin-1 Receptor Antagonist Inhibits Ischaemic and Excitotoxic Neuronal Damage in the Rat," Brain Research Bulletin, vol. 29, pp. 243-246 (1992).

Ronn et al., "A simple procedure for quantification of neurite outgrowth based on stereological principles," Journal of Neuroscience Methods, vol. 100, pp. 25-32 (2000).

Schreuder et al., "A new cytokine-receptor binding mode revealed by the crystal structure of the IL-1 receptor with an antagonist," Nature, vol. 386 pp. 194-200 (1997).

Secher et al., "A Neural Cell Adhesion Molecule-Derived Fibroblast Growth Factor Receptor Agonist, the FGL-Peptide, Promotes Early Postnatal Sensorimotor Development and Enhances Social Memory Retention," Neuroscience, vol. 141, pp. 1289-1299 (2006).

Siemion et al., "Anti-IL-1 Activity of Peptide Fragments of IL-1 Family Proteins," Peptides, vol. 19, No. 2, pp. 373-382 (1998).

Soroka et al., "Molecular Basis of Cell and Developmental Biology: Induction of Neuronal Differentiation by a Peptide Corresponding to the Homophilic Binding Site of the Second Ig Module of the Neural Cell Adhesion Molecule," The Journal of Biological Chemistry, vol. 277, No. 27, pp. 24676-24683 (2002).

Spulber et al., "IL-1/IL-1ra balance in the brain revisited—Evidence from transgenic mouse models," Brain, Behavior, and Immunity, vol. 23, pp. 573-579 (2009).

Tarkowski et al., "Decreased Levels of Intrathecal Interleukin 1 Receptor Antagonist in Alzheimer's Disease," Dementia and Geriatric Cognitive Disorders, vol. 12, pp. 314-317 (2001).

Wieczorek et al., "A Hexapeptide VTKFYF From C-Terminal Part of Interleukin-1 Receptor Antagonist, an Inhibitor of IL-1-IL-1 Receptor Interaction," Polish Journal of Pharmacology, vol. 49, pp. 107-117 (1997).

Wieczorek et al., "The search for inhibitors of interleukin-1 based on the sequence of interleukin-1 receptor antagonist," Biomedical Peptides, Proteins & Nucleic Acids, vol. 2, pp. 123-129 (1997).

* cited by examiner

Figure 3

| Ligand | $k_a$ (M$^{-1}$s$^{-1}$) | $K_b$ (s$^{-1}$) | $K_D$ (M) |
|---|---|---|---|
| Ilantafin | $8.56 \pm 2.79 \times 10^3$ | $7.53 \pm 2.03 \times 10^{-4}$ | $1.71 \times 10^{-7} \pm 7.07 \times 10^{-9}$ |
| ILRa | $5.47 \pm 5.53 \times 10^5$ | $3.62 \pm 0.65 \times 10^{-3}$ | $4.80 \times 10^{-8} \pm 1.32 \times 10^{-8}$ |
| IL1β | $1.84 \pm 0.20 \times 10^5$ | $2.69 \pm 0.58 \times 10^{-3}$ | $2.75 \times 10^{-8} \pm 7.86 \times 10^{-9}$ |

ANTAGONISTS OF THE INTERLEUKIN-1 RECEPTOR

FIELD OF INVENTION

The present invention relates to novel compounds comprising short peptides derived from the IL-1 receptor antagonist protein (IL1RA), capable of binding to the cell surface IL-1 receptor 1 to antagonise the inflammatory effects of IL-1 throughout the human body. Also disclosed is the use of said peptides as anti-inflammatory agents for treatment of pathological conditions wherein IL-1 plays a prominent role, such as inflammatory conditions of the body and the central nervous system.

BACKGROUND OF INVENTION

Interleukin 1 (IL-1) is a general name for two distinct proteins, IL-1 alpha and IL-1 beta, which are major pro-inflammatory cytokines. IL-1 exerts its effects by binding to specific transmembrane receptors (IL-1RI) on multiple cell types. The effects of IL-1 are counteracted by natural inhibitors such as soluble IL-1 receptors and IL-1R antagonist protein (IL1RA or IL1Ra). IL1RA inhibits the effect of IL-1 by blocking its interaction with the cell surface receptors.

Therapeutic approaches for targeting IL-1 for anti-inflammatory purposes have been addressed in the art. These include administration of recombinant IL-1R antagonist protein, IL-1 trap fusion proteins, anti-IL-1 antibodies, anti-IL-1RI and soluble IL-1RI and II in experimental models of arthritis (reviewed in Gabay C et al. 2010).

Peptides with IL-1R antagonist activity are disclosed in e.g. US20060094663A1. These sequences are derived from IL-1RAcP (IL-1RI accessory protein).

Recombinant IL-1R antagonist protein for use as an anti-inflammatory drug has been commercialised: Anakinra, sold under the trade name 'Kinerer' (See U.S. Pat. No. 5,075,222). It has been approved for treatment of rheumatoid arthritis. The drawbacks of anakinra is that (1) it is delivered as an injection concentrate with 100 mg in each dose; (2) it is prepared from genetically modified E. coli using recombinant DNA technology; and (3) it has a high molecular weight (corresponding to full-length IL-1RA)

Thus, identification of shorter and potent peptides derived from IL1RA may address these disadvantages, in that (1) a lower concentration of the present peptides may be used, (2) the smaller peptides are stable in solution and can be more easily chemically synthesised with a lower associated cost, and (3) the lower molecular weight of the small mimetic peptides enable them to more easily pass the blood-brain barrier, meaning a lower peptide amount is needed to reach working concentrations in the brain—this makes them particularly useful also for treatment of neuroinflammatory diseases. Specific targeting also has the potential of fewer side-effects and improved efficacy.

The WO05086695A2 patent family discloses specific peptide fragments of the IL-1R antagonist protein. These fragments are capable of inhibiting tissue destruction in inflammatory disorders, and may be used to treat chronic inflammatory disorders and rheumatoid arthritis (US2007027082; patent application of issued U.S. Pat. No. 7,674,464). No effect on neurodegenerative disorders is addressed.

According to US2007027082, the disclosed peptide fragments preferably comprise the subsequence LVAGY ("SEQ ID NO:42"); being present in "SEQ ID NOs:13, 18, 21, 23, 24 and 43" of US2007027082. Reversal of IL-1 induced effects were observed for "SEQ ID NO:13, 15, 23 and 24" in vitro (Example 3), and "SEQ ID NO:18 and 43" in vivo (Example 10).

"SEQ ID NOs:13, 18 and 19" of US2007027082 further comprise the subsequence SGRKSSKMQA of ILR1A (present SEQ ID NO:1). The shortest peptide comprising the subsequence SGRKSSKMQA of ILR1A having an effect according to US2007027082 is 35 amino acids long ("SEQ ID NO:13"), being 42 amino acids long when a nuclear localisation signal is added for optimisation ("SEQ ID NO:18"). When examined as short as 15 amino acids—excluding the LVAGY subsequence ("SEQ ID NO:19"), no effect is observed on inhibiting the collagenase production stimulated by IL-1 in vitro (Example 3). It is thus concluded in US2007027082 that all peptides active in inhibiting MMP-1 (a collagenase) by IL-1 beta contain residues LVAGY of IL1RA; being common to all 4 isoforms of IL1RA (US2007027082 [0115]).

The present invention discloses further peptide fragments of IL-1RA; in one embodiment being as short as 10 amino acids and in one embodiment comprising or consisting of SGRKSSKMQA (SEQ ID NO:1). Such fragments are shown herein to directly bind to IL-1RI and interfere with the binding of IL-1R to IL-1 beta; which is in contrast to the 35-amino acid long peptide fragment ("SEQ ID NO:13") of US2007027082 that does not bind IL1R1.

Short peptides according to the present invention may comprise or consist of SGRKSSKMQA (SEQ ID NO:1) or variants, fragments, or variants of fragments thereof. They have the advantage over both full-length IL1RA (anakinra) and the 35 and 42 amino-acid long peptides of US2007027082 (both comprising the subsequence SGRKSSKMQA) that they are very stable, has a high solubility and also have a low cost of synthesis. These effects occur with a retained ability of the peptides to bind IL1R1 and antagonise the effect of IL-1.

Further short peptides of the present invention derived from IL1RA invention comprise or consist of RIWDVNQKT (SEQ ID NO:29), TAMEADQPVS (SEQ ID NO:35) or GPNAKLEEKA (SEQ ID NO:36) or variants, fragments, or variants of fragments thereof; having the same advantages as outlined for SEQ ID NO:1 herein.

Furthermore, peptides of a certain short length; such as the 10-amino acid peptide of SEQ ID NO:1, have an increased capability of passing the blood-brain-barrier (BBB) to elicit an effect on cells of the central nervous system (CNS); thus enabling use of said short peptides on neuroinflammatory disorders associated with IL-1. An effect on neurons of IL1RA or peptide fragments thereof has not been addressed in the art previously, nor has passing the BBB. A positive effect on neurite outgrowth and neuronal cell survival is shown herein.

SUMMARY OF INVENTION

The present invention relates to truncated forms of IL1RA having improved properties over the full-length IL1RA protein and anakinra.

The peptides are shown herein by the present inventors to bind to IL-1R1, and interfere with the binding of IL-1R1 to the cytokine IL-1 beta, thus having an inhibitory effect on IL-1 downstream signalling including inhibition of NF-κB activation and reduced TNF-alpha increase. Also, a positive effect on neurite outgrowth and cell survival is observed in neurons, and signs of rheumatoid arthritis are ameliorated in vivo.

It is an aspect of the present invention to provide an isolated peptide consisting of a peptide sequence of 5 to 20 contiguous amino acid residues derived from IL-1 receptor antagonist protein (IL1RA), said peptide consisting of the amino acid sequence of any one of SEQ ID NO:1, SEQ ID NO:29, SEQ ID NO:35 or SEQ ID NO:36; or a fragment consisting of 5 or more consecutive amino acids of any one of SEQ ID NO:1, SEQ ID NO:29, SEQ ID NO:35 or SEQ ID NO:36; or a variant of any one of SEQ ID NO:1, SEQ ID NO:29, SEQ ID NO:35 or SEQ ID NO:36, said variant consisting of an amino acid sequence of 5 to 20 amino acids having at least 50% identity to any one of SEQ ID NO:1, SEQ ID NO:29, SEQ ID NO:35 or SEQ ID NO:36, wherein said peptide is capable of binding to IL-1 receptor type 1 (IL1RI), and capable of interfering with the binding of IL-1 to IL1RI.

It is also an aspect of the present invention to provide a compound comprising at least one peptide according to the present invention. Said compound may be formulated as a monomer consisting of a single copy of the peptide, or may be formulated as a multimeric compound comprising two or more peptides according to the invention. Said two or more peptides may be identical or not, with respect to each other. Said multimer may in a particular embodiment be a dimer or a tetrameric dendrimer.

Also provided herein is a composition, such as a pharmaceutical composition or formulation, comprising a peptide or a compound according to the invention.

In an interesting aspect, the peptides, compounds and compositions according to the invention are provided for use as a medicament.

Said use may comprise the treatment of a subset of inflammatory disorders, especially those wherein IL-1 plays a prominent role. These include rheumatoid arthritis, diabetes mellitus, such as diabetes mellitus type I, neurodegenerative disorder wherein said neurodegenerative disorder has a neuro-inflammatory component, including Alzheimer's disease, Parkinson's disease, Huntington's disease and Multiple Sclerosis.

DESCRIPTION OF DRAWINGS

FIG. 3 shows affinity and rate constants for interaction between Ilantafin (SEQ ID NO:1), IL1β and IL1Ra, and IL1RI.

Figure 1:
FIG. 1 shows a tertiary structure model of the complex between IL1Ra (space filling presentation) and IL1RI (backbone secondary structures). The location of the Ilantafin (aka. Ilantide) peptide sequence (SEQ ID NO:1) is shown in black.

Further details on the figures may be found in the Examples herein below.

DEFINITIONS AND ABBREVIATIONS

IL1RA or IL1Ra: IL-1 receptor antagonist protein, may also be denoted IL-1 receptor antagonist herein.

IL1R1 or IL1RI: IL1 receptor type 1.

Affinity: the strength of binding between receptors and their ligands.

Ilantafin/Ilantide: Used interchangeably herein to denote fragments of IL1RA; Ilantafin-8 has been examined mostly and given the sequence identifier SEQ ID NO:1. SEQ ID NO:1 may also be denoted simply as 'Ilantafin' or 'Ilantide' herein.

The term "Individual" refers to vertebrates, particular members of the mammalian species, preferably primates including humans. As used herein, 'subject' and 'individual' may be used interchangeably.

A "polypeptide" or "protein" is a polymer of amino acid residues preferably joined exclusively by peptide bonds, whether produced naturally or synthetically. The term "polypeptide" as used herein covers proteins, peptides and polypeptides, wherein said proteins, peptides or polypeptides may or may not have been post-translationally modified. A peptide is usually shorter in length than a protein.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatised forms.

An "amino acid residue" can be a natural or non-natural amino acid residue linked peptide bonds or bonds different from peptide bonds. The amino acid residues can be in D-configuration or L-configuration. An amino acid residue comprises an amino terminal part ($NH_2$) and a carboxy terminal part (COOH) separated by a central part comprising a carbon atom, or a chain of carbon atoms, at least one of which comprises at least one side chain or functional group. $NH_2$ refers to the amino group present at the amino terminal end of an amino acid or peptide, and COOH refers to the carboxy group present at the carboxy terminal end of an amino acid or peptide. The generic term amino acid comprises both natural and non-natural amino acids. Natural amino acids of standard nomenclature as listed in J. Biol. Chem., 243:3552-59 (1969) and adopted in 37 C.F.R., section 1.822(b)(2) belong to the group of amino acids listed in Table 1 herein below. Non-natural amino acids are those not listed in Table 1. Also, non-natural amino acid residues include, but are not limited to, modified amino acid residues, L-amino acid residues, and stereoisomers of D-amino acid residues.

TABLE 1

Natural amino acids and their respective codes.

| Symbols | | |
|---|---|---|
| 1-Letter | 3-Letter | Amino acid |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

An "equivalent amino acid residue" refers to an amino acid residue capable of replacing another amino acid residue in a polypeptide without substantially altering the structure and/or functionality of the polypeptide. Equivalent amino acids thus have similar properties such as bulkiness of the side-chain, side chain polarity (polar or non-polar), hydrophobicity (hydrophobic or hydrophilic), pH (acidic, neutral or basic) and side chain organization of carbon molecules (aromatic/aliphatic). As such, "equivalent amino acid residues" can be regarded as "conservative amino acid substitutions".

The classification of equivalent amino acids refers in one embodiment to the following classes: 1) HRK, 2) DENQ, 3) C, 4) STPAG, 5) MILV and 6) FYW Within the meaning of the term "equivalent amino acid substitution" as applied herein, one amino acid may be substituted for another, in one embodiment, within the groups of amino acids indicated herein below:

i) Amino acids having polar side chains (Asp, Glu, Lys, Arg, His, Asn, Gln, Ser, Thr, Tyr, and Cys,)
ii) Amino acids having non-polar side chains (Gly, Ala, Val, Leu, Ile, Phe, Trp, Pro, and Met)
iii) Amino acids having aliphatic side chains (Gly, Ala Val, Leu, Ile)
iv) Amino acids having cyclic side chains (Phe, Tyr, Trp, His, Pro)
v) Amino acids having aromatic side chains (Phe, Tyr, Trp)
vi) Amino acids having acidic side chains (Asp, Glu)
vii) Amino acids having basic side chains (Lys, Arg, His)
viii) Amino acids having amide side chains (Asn, Gln)
ix) Amino acids having hydroxy side chains (Ser, Thr)
x) Amino acids having sulphur-containing side chains (Cys, Met),
xi) Neutral, weakly hydrophobic amino acids (Pro, Ala, Gly, Ser, Thr)
xii) Hydrophilic, acidic amino acids (Gln, Asn, Glu, Asp), and
xiii) Hydrophobic amino acids (Leu, Ile, Val)

A "Bioactive agent" (i.e., biologically active substance/agent) is any agent, drug, compound, composition of matter or mixture which provides some pharmacologic, often beneficial, effect that can be demonstrated in-vivo or in vitro. It may refer to the Ilantafin/Ilantide peptide sequences, or compounds comprising these. As used herein, this term further includes any physiologically or pharmacologically active substance that produces a localized or systemic effect in an individual. Further examples of bioactive agents include, but are not limited to, agents comprising or consisting of an oligosaccharide, agents comprising or consisting of a polysaccharide, agents comprising or consisting of an optionally glycosylated peptide, agents comprising or consisting of an optionally glycosylated polypeptide, agents comprising or consisting of a nucleic acid, agents comprising or consisting of an oligonucleotide, agents comprising or consisting of a polynucleotide, agents comprising or consisting of a lipid, agents comprising or consisting of a fatty acid, agents comprising or consisting of a fatty acid ester and agents comprising or consisting of secondary metabolites. It may be used either prophylactically, therapeutically, in connection with treatment of an individual, such as a human or any other animal.

The terms "drug", "medicament" as used herein includes biologically, physiologically, or pharmacologically active substances that act locally or systemically in the human or animal body.

The terms "treating", "treatment" and "therapy" as used herein refer equally to curative therapy, prophylactic or preventative therapy and ameliorating or palliative therapy. The term includes an approach for obtaining beneficial or desired physiological results, which may be established clinically. For purposes of this invention, beneficial or desired clinical results include, but are not limited to, alleviation of symptoms, diminishment of extent of disease, stabilized (i.e., not worsening) condition, delay or slowing of progression or worsening of condition/symptoms, amelioration or palliation of the condition or symptoms, and remission (whether partial or total), whether detectable or undetectable. The term "palliation", and variations thereof, as used herein, means that the extent and/or undesirable manifestations of a physiological condition or symptom are lessened and/or time course of the progression is slowed or lengthened, as compared to not administering compositions of the present invention.

A "treatment effect" or "therapeutic effect" is manifested if there is a change in the condition being treated, as measured by the criteria constituting the definition of the terms "treating" and "treatment." There is a "change" in the condition being treated if there is at least 5% improvement, preferably 10% improvement, more preferably at least 25%, even more preferably at least 50%, such as at least 75%, and most preferably at least 100% improvement. The change can be based on improvements in the severity of the treated condition in an individual, or on a difference in the frequency of improved conditions in populations of individuals with and without treatment with the bioactive agent, or with the bioactive agent in combination with a pharmaceutical composition of the present invention.

A treatment according to the invention may be prophylactic, ameliorating or curative.

"Pharmacologically effective amount", "pharmaceutically effective amount" or "physiologically effective amount" of a "bioactive agent" is the amount of an active agent present in a pharmaceutical composition as described herein that is needed to provide a desired level of active agent in the bloodstream or at the site of action in an individual (e.g. the lungs, the gastric system, the colorectal system, prostate, etc.) to be treated to give an anticipated physiological response when such composition is administered. The precise amount will depend upon numerous factors, e.g., the active agent, the activity of the composition, the delivery device employed, the physical characteristics of the composition, intended patient use (i.e. the number of doses administered per day), patient considerations, and the like, and can readily be determined by one skilled in the art, based upon the information provided herein. An "effective amount" of a bioactive agent can be administered in one administration, or through multiple administrations of an amount that total an effective amount, preferably within a 24-hour period. It can be determined using standard clinical procedures for determining appropriate amounts and timing of administration. It is understood that the "effective amount" can be the result of empirical and/or individualized (case-by-case) determination on the part of the treating health care professional and/or individual.

The terms "enhancing" and "improving" a beneficial effect, and variations thereof, as used herein, refers to the therapeutic effect of the bioactive agent against placebo, or an increase in the therapeutic effect of a state-of-the-art medical treatment above that normally obtained when a pharmaceutical composition is administered without the bioactive agent of this invention. "An increase in the therapeutic effects" is manifested when there is an acceleration and/or increase in intensity and/or extent of the therapeutic effects obtained as a result of administering the bioactive agent(s). It also includes extension of the longevity of therapeutic benefits. It can also manifest where a lower amount of the pharmaceutical composition is required to obtain the same benefits and/or effects when it is co-administered with bioactive agent(s) provided by the present invention as compared to the administration in a higher amount of the pharmaceutical composition in the absence of bioactive agent. The enhancing effect preferably, but not necessarily, results in treatment of acute symptoms for which the pharmaceutical composition alone is not effective or is less effective therapeutically. Enhancement is achieved when there is at least a 5% increase in the therapeutic effects, such as at least 10% increase in the therapeutic effects when a bioactive agent of the present invention is co-administered with a pharmaceutical composition compared with administration of the pharmaceutical composition alone. Preferably the increase is at least 25%, more preferably at least 50%, even more preferably at least 75%, most preferably at least 100%.

"Co-administering" or "co-administration" of bioactive agents and state-of-the-art medicaments, as used herein, refers to the administration of one or more bioactive agents of the present invention, or administration of one or more bioactive agents of the present invention and a state-of-the-art pharmaceutical composition within a certain time period. The time period is preferably less than 72 hours, such as 48 hours, for example less than 24 hours, such as less than 12 hours, for example less than 6 hours, such as less than 3 hours. However, these terms also mean that the bioactive agent and a therapeutic composition can be administered together.

An "individual in need thereof" refers to an individual who may benefit from the present invention. In one embodiment, said individual in need thereof is a diseased individual, wherein said disease may be an immune disease wherein IL-1 plays a prominent role.

The term "Kit of parts" as used in the present invention provides the one or more peptides, compounds or compositions according to the present invention and a second bioactive agent for administration in combination. The parts of the kit are meant to be for simultaneous, separate or sequential use. The use may be a therapeutic use, such as the treatment of inflammation wherein IL-1 plays a prominent role.

Due to the imprecision of standard analytical methods, molecular weights and lengths of polymers are understood to be approximate values. When such a value is expressed as "about" X or "approximately" X, the stated value of X will be understood to be accurate to +/−20%, such as +/−10%, for example +/−5%.

DETAILED DESCRIPTION OF THE INVENTION

Inflammation

Inflammation (Latin, inflammare, to set on fire) is part of the complex biological response of vascular tissues to harmful stimuli, such as pathogens, damaged cells, or irritants. Inflammation is a protective attempt by the organism to remove the injurious stimuli and to initiate the healing process. Inflammation is not a synonym for infection, even in cases where inflammation is caused by infection. Although infection is caused by a microorganism, inflammation is one of the responses of the organism to the pathogen.

Inflammation can be classified as either acute or chronic. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells present at the site of inflammation and is characterized by simultaneous destruction and healing of the tissue from the inflammatory process Interleukins Interleukins are a group of cytokines (secreted proteins/ signaling molecules) that were first seen to be expressed by white blood cells (leukocytes). The term interleukin derives from (inter-) "as a means of communication", and (-leukin) "deriving from the fact that many of these proteins are produced by leukocytes and act on leukocytes". The name is something of a relic though as it has since been found that interleukins are produced by a wide variety of cells.

The function of the immune system depends in a large part on interleukins, and rare deficiencies of a number of them have been described, all featuring autoimmune diseases or immune deficiency. The majority of interleukins are synthesized by helper CD4+ T lymphocytes, as well as through monocytes, macrophages, and endothelial cells. They promote the development and differentiation of T, B, and hematopoietic cells.

Interleukin-1 (IL-1)

Interleukin 1 (IL-1) is a general name for two distinct proteins, IL-1 alpha (IL1A) and IL-1 beta (IL1B), which are major pro-inflammatory cytokines. They participate in the regulation of immune responses, inflammatory reactions, tissue injury and hematopoiesis.

The IL1 gene family consists of three members, IL1α, IL1β, and IL1RA (IL-1 receptor antagonist protein, also IL1Ra). IL1RA consists of a six-stranded β-barrel closed on one side by three β-hairpin loops. Although IL1α and IL1β are agonists of the IL1 receptor, the naturally occurring IL1RA functions as a specific antagonist of the receptor (Hallegua and Weisman, 2002).

IL-1 Alpha

Interleukin-1 alpha (IL-1α) is a protein that in humans is encoded by the IL1A gene. The protein encoded by this gene is a cytokine of the interleukin-1 family. Interleukin-1 alpha possesses a wide spectrum of metabolic, physiological, haematopoietic activities, and plays one of the central roles in the regulation of the immune responses. It binds to the interleukin-1 receptor. IL-1a is a unique member in the cytokine family in the sense that the structure of its initially synthesized precursor does not contain a signal peptide fragment (same is known for IL-1β and IL-18). After processing by the removal of N-terminal amino acids by specific proteases, the resulting peptide is called "mature" form. Calpain, a calcium-activated cysteine protease, associated with the plasma membrane, is primarily responsible for the cleavage of the IL-1α precursor into a mature molecule. Both the 31 kDa precursor form of IL-1α and its 18 kDa mature form are biologically active.

The 31 kDa IL-1α precursor is synthesized in association with cytoskeletal structures (micro-tubules), unlike most proteins, which are translated in the endoplasmic reticulum.

The three-dimensional structure of the IL-1α contains an open-ended barrel composed entirely of beta-pleated strands. Crystal structure analysis of the mature form of IL-1α shows that it has two sites of binding to IL-1 receptor. There is a primary binding site located at the open top of its barrel, which is similar, but not identical to that of IL-1β.

IL-1α is constitutively produced by epithelial cells and is found in substantial amounts in normal human epidermis, where it has an essential role in maintenance of skin barrier function. With the exception of skin keratinocytes, some epithelial cells and certain cells in central nervous system, IL-1α is not observed in health in most of cell types, tissues and in blood. A wide variety of other cells only upon stimulation can be induced to transcribe the IL-1α genes and produce the precursor form of IL-1α. Among them are fibroblasts, macrophages, granulocytes, eosinophils, mast cells and basophils, endothelial cells, platelets, monocytes and myeloid cell lines, blood T-lymphocytes and B-lymphocytes, astrocytes, kidney mesangial cells, Langerhans cells, dermal dendritic cells, natural killer cells, large granular lymphocytes, microglia, blood neutrophils, lymph node cells, maternal placental cells and several other cell types.

The most important regulatory molecule for IL-1α activity is IL-1RA, which is usually produced in a 10-100-fold molar excess. In addition, the soluble form of the IL-1R type I has a high affinity for IL-1α and is produced in a 5-10 molar excess. IL-10 also inhibits IL-1α synthesis.

IL-1 Beta

Interleukin-1 beta (IL-16) also known as catabolin, is a cytokine protein that in humans is encoded by the IL1B gene. IL-1β precursor is cleaved by caspase 1 (interleukin 1 beta convertase). Cytosolic thiol protease cleaves the product to form mature IL-1β.

IL-1β is a member of the interleukin 1 cytokine family. This cytokine is produced by activated macrophages as a proprotein, which is proteolytically processed to its active form by caspase 1. This cytokine is an important mediator of the inflammatory response, and is involved in a variety of cellular activities, including cell proliferation, differentiation, and apoptosis. The induction of cyclooxygenase-2 (PTGS2/ COX2) by this cytokine in the central nervous system (CNS) is found to contribute to inflammatory pain hypersensitivity. This gene and eight other interleukin 1 family genes form a cytokine gene cluster on chromosome 2.

IL-1 Receptor Antagonist Protein (IL1RA)

The interleukin-1 receptor antagonist protein (IL1RA) is a protein that in humans is encoded by the IL1RN gene. It is a member of the IL-1 cytokine family that inhibits the activities of IL1A and IL1B, and modulates a variety of IL-1 related immune and inflammatory responses. This gene and five other closely related cytokine genes form a gene cluster spanning approximately 400 kb on chromosome 2. Four alternatively spliced transcript variants encoding distinct isoforms have been reported. Mutations in the IL1RN gene results in a rare disease called deficiency of the interleukin-1-receptor antagonist (DIRA). Variants of the IL1RN gene are also associated with risk of schizophrenia.

In terms of protein similarities, IL-1β is more closely related to IL-1RA than it is to IL-1α. The amino acids that are identical between mature human IL-1α and mature IL-1β is 22% while it is 26% when comparing IL-1β to IL-1RA and only 18% when comparing IL-1α to IL-1RA.

The sequence of IL1RA is disclosed herein below ('sequences'), for all 4 isoforms of IL1RA.

IL-1 Receptors

IL1 has two distinct receptors, IL1RI and IL1RII (IL-1 receptor type I and II, or 1 and 2, respectively). IL1RI comprises an extracellular portion with three immunoglobulin-like modules for IL1 binding and a long cytoplasmic domain, whereas IL1RII contains the same ectodomain but a shorter cytoplasmic domain.

The receptors both exist in transmembrane (TM) and soluble forms: the soluble IL-1 receptors are thought to be post-translationally derived from cleavage of the extracellular portion of the membrane receptors. Both IL-1 receptors (CD121a/IL1R1, CD121b/IL1R2) appear to be well conserved in evolution, and map to the same chromosomal location. The receptors can both bind all three forms of IL-1 (IL-1 alpha, IL-1 beta and IL-1RA).

IL1 associates with IL1RI with low affinity, and the binding of the IL1R accessory protein (IL1R-AcP) to the complex results in high-affinity binding that forms an asymmetric tertiary complex composed of IL1, IL1RI, and IL1R-AcP, resulting in receptor activation and subsequent intracellular signal transduction and cellular responses. IL1RA binds primarily to IL1RI but does not induce signal transduction because it lacks a second binding site. IL1RII is a decoy receptor because the binding of IL1 to ILRII is unable to trigger intracellular signals. The naturally occurring IL1RA and the decoy receptor attenuate the effects of IL1, and thus appears to be a unique phenomenon in cytokine biology (Dinarello, 1996).

Peptide Fragments of the Present Invention

The present invention discloses truncated forms of IL1RA having improved properties over the full-length IL1RA protein and anakinra. The improved properties of the short peptides of the present invention relate to increased solubility, increased stability and lower cost of synthesis. Furthermore, the peptide of the present invention retains its ability to bind to IL-1R1 and interfere with binding of IL-1 beta to this receptor; in addition to several desirable downstream effects addressed herein elsewhere.

The provision of a short peptide according to the present invention also allow for better passage of said short peptide across the blood-brain barrier. This is especially interesting in that the peptide of the present invention (SEQ ID NO:1) of 10 amino acid residues, has been shown by the present inventors to have a positive effect on neurite outgrowth and neuronal cell survival.

The blood-brain barrier (BBB) is a separation of circulating blood and the cerobrospinal fluid (CSF) in the central nervous system (CNS), provided to maintain homeostasis. It occurs along all brain capillaries and consists of tight junctions around the capillaries that do not exist in normal circulation. Endothelial cells restrict the diffusion of microscopic objects (e.g. bacteria) and large or hydrophilic molecules into the cerebrospinal fluid, while allowing the diffusion of small hydrophobic molecules ($O_2$, hormones, $CO_2$). Cells of the barrier actively transport metabolic products such as glucose across the barrier with specific proteins. This barrier also includes a thick basement membrane and astrocytic endfeet. The BBB thus effectively blocks entry into the brain of most molecules. This means that many drugs, which would otherwise be capable of treating disorders of the CNS, are denied access to the very regions where they would be affective.

While most peptides may be able to penetrate the BBB to some extent, there is a clear correlation between the molecular weight (MW) of the protein and the degree of penetration—shorter, unbranched peptides with a low MW thus have a better degree of penetration, meaning that a lower amount of peptide is needed for small MW peptides to reach working concentrations in the brain.

A peptide according to the invention comprises a short fragment of the IL1RA protein. In one embodiment, said peptide comprises or consists of SGRKSSKMQA (SEQ ID NO:1), or a functional fragment or variant thereof.

A 'fragment or variant thereof' as used herein refer to fragments of SEQ ID NO:1 (length), variants of SEQ ID NO:1 (identity), and variants of fragments of SEQ ID NO:1 (identity and length). The latter may be denoted 'variant fragment'.

Both fragments and variants of amino acid sequences according to the invention are meant to be the functional equivalents of said sequences, i.e. retaining their ability to bind to IL1R1.

Further short peptides of the present invention derived from IL1RA invention comprise or consist of RIWDVNQKT (SEQ ID NO:29), TAMEADQPVS (SEQ ID NO:35) or GPNAKLEEKA (SEQ ID NO:36) or variants, fragments, or variants of fragments thereof; as outlined for SEQ ID NO:1 herein.

In a preferred embodiment, the peptides according to the present invention are specific, in that the peptide sequence have no or substantially reduced effect when the amino acid sequence is scrambled or reversed. Also, the peptides are preferably specific to antagonising the effect of IL-1, and not other proteins and interleukins.

A functional fragment or variant of e.g. SEQ ID NO:1 is a fragment or variant (or variant of a fragment) which retain its ability to bind to IL-1R1 and interfere with the binding of IL-1 beta to said receptor, and/or retain the ability to affect downstream effects to a comparable level as SEQ ID NO:1 with respect to inhibition of IL-1 induced NF-κB activation, reduction of IL-1 induced TNF-alpha release from macrophages, induction of neurite outgrowth and/or promotion of neuronal cell survival. The same applies to SEQ ID NOs:29, 35 and 36.

In the present context the standard one-letter code for amino acid residues as well as the standard three-letter code is applied. Abbreviations for amino acids are in accordance with the recommendations in the IUPAC-IUB Joint Commission on Biochemical Nomenclature Eur. J. Biochem, 1984, vol. 184, pp 9-37. Throughout the application either the three letter code or the one letter code for natural amino acids are used. Where the L or D form (optical isomers) has not been specified it is to be understood that the amino acid in question has the natural L form, cf. Pure & Appl. Chem. Vol. (56(5) pp 595-624 (1984) or the D form, so that the peptides formed may be constituted of amino acids of L form, D form, or a sequence of mixed L forms and D forms.

Where nothing is specified it is to be understood that the C-terminal amino acid of a peptide according to the invention exists as the free carboxylic acid, this may also be specified as "—OH". However, the C-terminal amino acid of a peptide for use according to the invention may in another embodiment be the amidated derivative, which is indicated as "—NH₂". Where nothing else is stated the N-terminal amino acid of the peptide comprises a free amino-group, this may also be specified as "H-". However, the N-terminal amino acid of a peptide according to the invention may in another embodiment be the acetylated derivative, which is indicated as "-Acetyl" or "COCH$_3$".

A peptide according to the invention in one embodiment comprises at least 5 of the twenty-two amino acids naturally incorporated into polypeptides, called proteinogenic or natural amino acids. Of these, 20 are encoded by the universal genetic code. The remaining 2; selenocysteine and pyrrolysine, are incorporated into proteins by unique synthetic mechanisms. A peptide according to the invention can also comprise one or more unnatural, non-proteinogenic or non-standard amino acids.

In a preferred embodiment, the peptide of the present invention consists of or comprises SGRKSSKMQA (SEQ ID NO:1), or a fragment or a variant, or a variant fragment thereof.

In another embodiment, the peptide of the present invention consists of or comprises SEQ ID NOs:29, 35 or 36, or a fragment or a variant, or a variant fragment thereof.

In one embodiment, the peptide comprises a contiguous amino acid sequence of at most 14 amino acids, such as at most 13 amino acids, for example at most 12 amino acids, for example at most 11 amino acids, such as at most 10 amino acids derived from IL1RA which comprises SEQ ID NO:1, or a fragment or a variant, or a variant fragment thereof.

The peptide of the present invention in one embodiment consists of 10 contiguous amino acid residues of IL1RA consisting of SEQ ID NO:1. In another embodiment, the peptide of the invention has a total length of less than or equal to 5, 6, 7, 8, 9, 10, 11, 12 13 or 14 contiguous amino acid residues derived from IL1RA and comprises SEQ ID NO:1 or a variant or a fragment, or a variant fragment, thereof.

A peptide of the present invention may consist of 5-10 contiguous amino acids, such as 6-10 amino acids contiguous, for example 8-10 contiguous amino acids. In one embodiment, the peptide of the invention consists of 5-6, such as 6-7, for example 7-8, such as 8-9, for example 9-10, such as 10-11, for example 11-12, such as 12-13, for example 13-14 contiguous amino acids comprising any of SEQ ID NOs:1, 29, 35 or 36, or a variant, a fragment or a variant fragment thereof.

In one embodiment, the peptide of the invention consists of 5-6, such as 6-7, for example 7-8, such as 8-9, for example 9-10, such as 10-11, for example 11-12, such as 12-13, for example 13-14, such as 14-15, for example 15-16, such as 16-17, for example 17-18, such as 18-19, for example 19-20 contiguous amino acids comprising any of SEQ ID NOs:29, 35 or 36, or a variant, a fragment or a variant fragment thereof.

The peptide of the present invention in another embodiment comprises a contiguous amino acid sequence having a total length of less than or equal to 5, 6, 7, 8, 9, 10, 11, 12 13, 14, 15, 16, 17, 18, 19 or 20 contiguous amino acid residues derived from IL1RA comprising SEQ ID NOs:29, 35 or 36, or a fragment or a variant, or a variant fragment thereof.

In yet another embodiment, the peptide of the invention comprises or consists of a fragment of SEQ ID NOs:1, 29, 35 or 36 comprising at least 5 contiguous amino acids of said peptide sequence(s); such as 5 contiguous amino acids, for example 6 contiguous amino acids, such as 7 contiguous amino acids, for example 8 contiguous amino acids, such as 9 contiguous amino acids of said peptide sequence(s).

A fragment of a peptide is thus defined herein as a peptide comprising at least 5 contiguous amino acids of SEQ ID NOs:1, 29, 35 or 36; such as 5 contiguous amino acids, for example 6 contiguous amino acids, such as 7 contiguous amino acids, for example 8 contiguous amino acids, such as 9 contiguous amino acids of SEQ ID NOs:1, 29, 35 or 36. A fragment of SEQ ID NOs:1, 35 or 36 may thus comprise between 5 and 9 amino acids of said sequences, and a fragment of SEQ ID NO:29 may thus comprise between 5 and 8 amino acids of said sequence.

A variant of a peptide of the invention, or a variant of a fragment of said peptides, may be an amino acid sequence which has at least 40% sequence identity with SEQ ID NOs:1, 29, 35 or 36 or a fragment thereof, such as at least 50%, 60%, 65%, 70%, 75%, 80%, 85%, 90% or 95% identity to SEQ ID NOs:1, 29, 35 or 36 or a fragment thereof, or an amino acid which has 40-50% identity, for example 50-60% identity, such as 60-70% identity, for example 70-80% identity, such as 80-90%, for example 95-99% sequence identity to SEQ ID NOs:1, 29, 35 or 36 or a fragment thereof, wherein the identity is defined as a percentage of identical amino acids in said variant sequence when it is collated with SEQ ID NOs:1, 29, 35 or 36 or a fragment thereof.

The identity between amino acid sequences may be calculated using well known algorithms such as BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, or BLOSUM 90, or by simple comparison of the specific amino acids present at corresponding positions in two peptide sequences to be compared.

Homology may be used as a synonym to identity/sequence identity.

A variant of a peptide of the invention may also be an amino acid sequence which has about 10% positive amino acid matches with SEQ ID NOs:1, 29, 35 or 36 or a fragment thereof, such as about 20% positive amino acid matches, for example about 30% positive amino acid matches, such as about 40% positive amino acid matches, for example about 50% positive amino acid matches, such as about 60% positive amino acid matches, for example about 70% positive amino acid matches, such as about 80% positive amino acid matches, for example about 90% positive amino acid matches, wherein a positive amino acid match is defined as the presence at the same position in two compared sequences of amino acid residues which has similar physical and/or chemical properties. Particular positive amino acid matches of the present invention are K to R, E to D, L to M, Q to E, I to V, I to L, A to S, Y to W, K to Q, S to T, N to S and Q to R.

Variants include sequences wherein an alkyl amino acid is substituted for an alkyl amino acid, wherein an aromatic amino acid is substituted for an aromatic amino acid, wherein a sulfur-containing amino acid is substituted for a sulfur-containing amino acid, wherein a hydroxy-containing amino acid is substituted for a hydroxy-containing amino acid, wherein an acidic amino acid is substituted for an acidic amino acid, wherein a basic amino acid is substituted for a basic amino acid, or wherein a dibasic monocarboxylic amino acid is substituted for a dibasic monocarboxylic amino acid.

In another embodiment, a variant of the peptide sequences according to the invention, or a variant of a fragment of the peptide sequence, may comprise at least one substitution, such as a plurality of substitutions introduced independently of one another. In one embodiment, the peptide variant comprises 1, 2, 3, 4, 5 or 6 amino acid substitutions with respect to the amino acid sequence of SEQ ID NOs:1, 29, 35 or 36 or a fragment thereof.

Variants of SEQ ID NOs:1, 29, 35 or 36, or of fragments thereof, may comprise one or more conservative substitutions independently of one another, that is the substitution of amino acids whose side chains have similar biochemical properties and thus do not affect the function of the peptide.

Among the common amino acids, for example, a "conservative amino acid substitution" can also be illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

The polypeptides according to the present invention can also comprise non-naturally occurring amino acid residues. Non-naturally occurring amino acids include e.g., without limitation, trans-3-methylproline, 2,4-methanoproline, cis-4-hydroxyproline, trans-4-hydroxyproline, N-methylglycine, allo-threonine, methylthreonine, hydroxylethylcysteine, hydroxyethylhomocysteine, nitroglutamine, homo-glutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine.

Conservative substitutions (or synonymous substitutions) may be introduced in any one or more positions of a peptide according to the invention or a fragment thereof, as long as the variant, or variant of a fragment, remains functional. It may however also be desirable to introduce non-conservative substitutions in one or more positions (non-synonymous substitutions).

A non-conservative substitution leading to the formation of a variant of the peptide according to the invention would for example differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on peptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Substitution of amino acids may in one embodiment be made based upon their hydrophobicity and hydrophilicity values and the relative similarity of the amino acid side-chain substituents, including charge, size, and the like.

In one embodiment, 1, 2 or 3 serine residues (Ser) of SEQ ID NO:1, or a fragment thereof, is substituted with an amino acid selected from the group consisting of Gln, Asn and Thr (all amino acids with polar uncharged side chains); and independently thereof, glycine (Gly) is substituted with an amino acid selected from the group consisting of Ala, Val, Leu, and Ile; and independently thereof, at least one arginine (Arg) is substituted with an amino acid selected from the group consisting of Lys and His (all have positively charged side shains); and independently thereof, 1 or 2 lysine residues (Lys) are substituted with an amino acid selected from the group consisting of Arg and His; and independently thereof, methionine (Met) is substituted with an amino acid selected from the group consisting of Leu, Pro, Ile, Val, Phe, Tyr and Trp (all have hydrophobic side chains); and independently thereof, at least one glutamine (Gln) is substituted with an amino acid selected from the group consisting of Asp, Glu, and Asn; and independently thereof, at least one alanine (Ala) is substituted with an amino acid selected from the group consisting of Gly, Val, Leu, and Ile.

SEQ ID NO:1 consists of 10 amino acids, referred to as positions 1 to 10. In one embodiment, Ser at position 1 of SEQ ID NO:1 is unchanged, deleted or substituted with Gly; Gly at position 2 is unchanged, deleted or substituted with Ala, Ser or Arg; Arg at position 3 is unchanged, deleted or substituted with Lys; Lys at position 4 is unchanged or substituted with Arg, Thr, Gln, Met, Gly or Ser; Ser at position 5 is unchanged or substituted with Pro, AlaArg, Leu, Gln, Asn, Gly or Lys; Ser at position 6 is unchanged or substituted with His, Gln, Trp, Asn, Glu, Pro, Ala, Thr, Cys, Gly or Arg; Lys at position 7 is unchanged or substituted with Arg, His, Glu or Ser; Met at position 8 is unchanged or substituted with Leu, Thr or Ser; Gln at position 9 is unchanged, deleted or substituted with Glu, His or Lys; and/or Ala at position 10 is unchanged, deleted or substituted with Leu or Met.

Furthermore, a functional variant of SEQ ID NOs:1, 29, 35 or 36 may comprise one or more amino acid additions within or at either end of said sequence, such as 1, 2, 3, 4 or 5 amino acids added within or at either end of SEQ ID NOs:1, 29, 35 or 36, or a variant, a fragment or a variant fragment thereof.

Examples of variants, fragments and variants of fragments of SEQ ID NO:1 according to the present invention include (identical amino acids compared to SEQ ID NO:1 are underlined, and 'missing' or omitted amino acids compared to SEQ ID NO:1 are indicated with an "-"; the overall identity score is indicated; as compared to SEQ ID NO:1):

```
SEQ ID NO:  1  SGRKSSKMQA   ('Ilantafin'/'Ilantide')
SEQ ID NO:  2  SGRKPSKMQA   Identity: 9/10 (90%)
SEQ ID NO:  3  SGRKSQKM--   Identity: 7/8 (87.5%)
SEQ ID NO:  4  --RKASKLQA   Identity: 6/8 (75%)
SEQ ID NO:  5  SARKSEKM--   Identity: 6/8 (75%)
SEQ ID NO:  6  SGRQSPKM--   Identity: 6/8 (75%)
SEQ ID NO:  7  SGRKSPHSKLPA Identity: 5/10 (50%)
SEQ ID NO:  8  SSRQSSKM--   Identity: 6/8 (75%)
SEQ ID NO:  9  SGKRPCKMQA   Identity: 6/10 (60%)
SEQ ID NO: 10  --RMNSKMQ-   Identity: 5/7 (71.4%)
SEQ ID NO: 11  ---KSPKMQ-   Identity: 5/6 (83.3%)
SEQ ID NO: 12  --RKGGKMQ-   Identity: 5/7 (71.4%)
SEQ ID NO: 13  SGRGKSSSKM   Identity: 4/10 (40%)
SEQ ID NO: 14  GRRSSRKMPA   Identity: 5/10 (50%)
SEQ ID NO: 15  --RKANKLQA   Identity: 5/8 (62.5%)
SEQ ID NO: 16  SGRKSHRLQ-   Identity: 6/9 (66.6%)
SEQ ID NO: 17  --RKAWKMQ-   Identity: 5/7 (71.4%)
SEQ ID NO: 18  --RKANKLQA   Identity: 5/8 (62.5%)
SEQ ID NO: 19  -GRRSSKTEA   Identity: 6/9 (66.6%)
SEQ ID NO: 20  --RTSSRMQ-   Identity: 5/7 (71.4%)
SEQ ID NO: 21  -GRKRSRMH-   Identity: 5/8 (62.5%)
SEQ ID NO: 22  -GRKRSKTQ-   Identity: 6/8 (75%)
SEQ ID NO: 23  SGRKLAKLQ-   Identity: 6/9 (66.6%)
SEQ ID NO: 24  --RKSTEMEA   Identity: 5/8 (62.5%)
```

-continued

SEQ ID NO: 25--RKQNKMEA    Identity: 5/8 (62.5%)

SEQ ID NO: 26--RRSSRLQA    Identity: 5/8 (62.5%)

SEQ ID NO: 27--RTSSRMQ-    Identity: 5/7 (71.4%)

A variant of a peptide of the invention may also mean that the peptide sequence may be modified. A modification may be any modification known to the skilled person, such as those referred to as posttranslational modifications. These include acetylation, phosphorylation, methylation, glucosylation, glycation, amidation, hydroxylation, deimination, deamidation, carbamylation and sulfation of one or more amino acid residues.

In one embodiment, the peptide of the present invention does not comprise or consist of the amino acid sequence RPSGRKSSKMQAFRI (SEQ ID NO:37), and/or does not comprise or consist of the amino acid sequence LVAGY (SEQ ID NO:38).

In one embodiment, the peptide according to the invention is an isolated peptide.

In one embodiment, the peptide according to the invention is a non-naturally occurring peptide; being derived from a naturally occurring protein (IL1RA). It is in one embodiment synthetically made.

In a particular embodiment, the peptides according to the present invention have a molecular weight in the range from 100 Da to 5000 Da, such as from 100 Da to 250 Da, for example 250 Da to 500 Da, such as from 500 Da to 750 Da, for example 750 Da to 1000 Da, such as from 1000 Da to 1500 Da, for example 1500 Da to 2000 Da, such as from 2000 Da to 3000 Da, for example 3000 Da to 4000 Da, such as from 4000 Da to 5000 Da.

It is an aspect of the present invention to provide a peptide according to the present invention for use as a medicament.

Synthetic Preparation

The methods for synthetic production of peptides are well known in the art. Detailed descriptions as well as practical advice for producing synthetic peptides may be found in Synthetic Peptides: A User's Guide (Advances in Molecular Biology), Grant G. A. ed., Oxford University Press, 2002, or in: Pharmaceutical Formulation: Development of Peptides and Proteins, Frokjaer and Hovgaard eds., Taylor and Francis, 1999.

Peptides according to the invention may be synthesized as monomers, dimers or tetramers (>80% purity, Schafer-N, Copenhagen, Denmark). Dimers and tetramers consist of two and four chains, respectively, in one embodiment coupled to a lysine backbone.

In one embodiment the peptide sequences of the invention are produced synthetically, in particular, by the Sequence Assisted Peptide Synthesis (SAPS) method or Solid-phase peptide synthesis (SPPS). These are well-known to the skilled person.

Peptides may be synthesised either batch wise on a fully automated peptide synthesiser using 9-fluorenylmethyloxycarbonyl (Fmoc) or tert-Butyloxycarbonyl (Boc) as N-a-amino protecting group and suitable common protection groups for side-chain functionalities.

After purification by reversed phase HPLC, peptides may be further processed to obtain for example cyclic or C- or N-terminal modified isoforms. The methods for cyclization and terminal modification are well-known in the art.

Compound of the Present Invention

It is an aspect of the present invention to provide a compound comprising or consisting of a peptide according to the present invention. In one embodiment, said peptide is formulated as a monomer (i.e. comprising 1 copy of the peptide), whereas in another embodiment, said peptide is formulated as a multimer.

It is an aspect of the present invention to provide a compound according to the present invention for use as a medicament.

Multimeric Compound

A peptide sequence of the present invention may be connected to another (identical or non-identical) peptide sequence of the present invention by a chemical bond or through a linker group. In some embodiments a peptide of the invention may be formulated as an oligomer or multimer of monomers, wherein each monomer is as a peptide sequence as defined herein above.

Thus, according to the invention a multimeric compound may be a polymer comprising two or more peptide sequences of the invention, said peptide sequences being identical or non-identical, wherein at least one of the two or more peptide sequences is a peptide according to the present invention. Preferably, both peptide sequences are a peptide according to the present invention.

In one embodiment the multimeric compound is a dimer, comprising two peptides according to the present invention, said two peptides being identical or non-identical with respect to each other.

In another embodiment the multimeric compound is a trimer or a tetramer, comprising three or four peptides according to the present invention, respectively, said peptides being identical or non-identical with respect to each other.

In one embodiment the multimeric compound is a dendrimer, such as a tetrameric dendrimer. Dendrimers are repeatedly branched, roughly spherical large molecules, typically symmetric around the core, and often adopts a spherical three-dimensional morphology. Dendrimers according to the present invention may comprise 4 peptides, 8 peptides, 16 peptides, or 32 peptides; preferably four peptides (i.e. tetrameric dendrimer).

In some particular embodiments, the multimeric compound may comprise two identical amino acid sequences of the present invention (dimer) or the compound may comprise four identical copies of an amino acid sequence of the present invention (tetrameric dendrimer).

The multimers according to the invention may be made by linking two or more peptide monomers via a peptide bond or a linker group. They may be linked to a lysine backbone, such as a lysine residue (a single lysine residue), or coupled to a polymer carrier, for example a protein carrier. Said linker group in one embodiment comprises a plurality of lysine residues, such as a core moiety having a plurality of lysine residues. However, any other linking of peptide monomers known to the skilled person may be envisioned.

The linking may in one embodiment occur at the N-terminal or C-terminal end of the peptide monomers.

Methods

It is also an aspect of the present invention to provide a method for stimulating neurite outgrowth and/or promoting survival of neurons, said method comprising administering an effective amount of a peptide, of a compound, or of a composition according to the present invention, to an individual in need thereof.

Also disclosed in a method for interfering with the binding of IL1RI to IL-1, said method comprising administering an effective amount of a peptide, of a compound, or of a composition according to the present invention, to an individual in need thereof.

In a preferred embodiment, said individual in a human being, such as a human being having a neurodegenerative condition.

The invention also relates to a method for identifying binding partners for peptides described herein, said method comprising the steps of extracting the polypeptide and isolating said binding partners.

Pharmaceutical Formulation

Whilst it is possible for the peptides or compounds of the present invention to be administered as the raw chemical (or peptide), it is sometimes preferred to present them in the form of a pharmaceutical formulation. Such a pharmaceutical formulation may be referred to as a pharmaceutical composition or pharmaceutically acceptable or safe composition.

Accordingly, the present invention further provides a pharmaceutical formulation, which comprises a peptide or compound of the present invention, or a pharmaceutically acceptable salt or ester thereof, and a pharmaceutically acceptable carrier and/or diluent. The pharmaceutical formulations may be prepared by conventional techniques, e.g. as described in Remington: The Science and Practice of Pharmacy 2005, Lippincott, Williams & Wilkins.

The pharmaceutically acceptable carriers can be either solid or liquid. Solid form preparations include powders, tablets, pills, capsules, cachets, suppositories, and dispersible granules. A solid carrier can be one or more excipients which may also act as diluents, flavoring agents, solubilizers, lubricants, suspending agents, binders, preservatives, wetting agents, tablet disintegrating agents, or an encapsulating material.

Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene, water, saline or a glucose solution. Similarly, the carrier or diluent may include any sustained release material known in the art, such as glycerol monostearate or glycerol distearate, alone or mixed with a wax.

Also included are solid form preparations which are intended to be converted, shortly before use, to liquid form preparations. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The compounds of the present invention may be formulated for parenteral administration and may be presented in unit dose form in ampoules, pre-filled syringes, small volume infusion or in multi-dose containers, optionally with an added preservative. The compositions may take such forms as suspensions, solutions, or emulsions in oily or aqueous vehicles, for example solutions in aqueous polyethylene glycol.

Examples of oily or non-aqueous carriers, diluents, solvents or vehicles include propylene glycol, polyethylene glycol, vegetable oils (e.g., olive oil), and injectable organic esters (e.g., ethyl oleate), and may contain agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the invention may also be formulated for topical delivery. Regions for topical administration include the skin surface and also mucous membrane tissues of the vagina, rectum, nose, mouth, and throat. The topical formulation may include a pharmaceutically acceptable carrier adapted for topical administration. Thus, the composition may take the form of a suspension, solution, ointment, lotion, sexual lubricant, cream, foam, aerosol, spray, suppository, implant, inhalant, tablet, capsule, dry powder, syrup, balm or lozenge, for example.

The pharmaceutical formulation described herein can be administered transdermally. Transdermal administration typically involves the delivery of a compound for percutaneous passage of the drug into the systemic circulation of the patient. The skin sites include anatomic regions for transdermally administering the drug and include the forearm, abdomen, chest, back, buttock, mastoidal area, and the like.

Transdermal delivery is accomplished by exposing a source of the compound to a patient's skin for an extended period of time. Transdermal patches have the added advantage of providing controlled delivery of a pharmaceutical agent-chemical modifier complex to the body. Such dosage forms can be made by dissolving, dispersing, or otherwise incorporating the pharmaceutical agent-chemical modifier complex in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel. For example, a simple adhesive patch can be prepared from a backing material and an acrylate adhesive.

Lotions according to the present invention also include those suitable for application to the eye. An eye lotion may comprise a sterile aqueous solution optionally containing a bactericide.

Formulations for use in nasal, pulmonary and/or bronchial administration are normally administered as aerosols in order to ensure that the aerosolized dose actually reaches the mucous membranes of the nasal passages, bronchial tract or the lung. The term "aerosol particle" is used herein to describe the liquid or solid particle suitable for nasal, bronchial or pulmonary administration, i.e., that will reach the mucous membranes.

Typically aerosols are administered by use of a mechanical devices designed for pulmonary and/or bronchial delivery, including but not limited to nebulizers, metered dose inhalers, and powder inhalers. With regard to construction of the delivery device, any form of aerosolization known in the art, including but not limited to spray bottles, nebulization, atomization or pump aerosolization of a liquid formulation, and aerosolization of a dry powder formulation, can be used.

Liquid aerosol formulations in general contain a compound of the present invention in a pharmaceutically acceptable diluent. Pharmaceutically acceptable diluents include but are not limited to sterile water, saline, buffered saline, dextrose solution, and the like.

Formulations for dispensing from a powder inhaler device will normally comprise a finely divided dry powder containing pharmaceutical composition of the present invention (or derivative) and may also include a bulking agent, such as lactose, sorbitol, sucrose, or mannitol in amounts which facilitate dispersal of the powder from the device. Dry powder formulations for inhalation may also be formulated using powder-filled capsules, in particularly capsules the material of which is selected from among the synthetic plastics.

The formulation is formulated to the type of device employed and may involve the use of an appropriate propellant material, in addition to the usual diluents, adjuvants and/or carriers useful in therapy and known to the person skilled in the art. The propellant may be any propellant generally used in the art. Specific non-limiting examples of such useful propellants are a chlorofluorocarbon, a hydrofluorocarbon, a hydrochlorofluorocarbon, or a hydrocarbon.

The formulations of the present embodiment may also include other agents useful for pH maintenance, solution stabilization, or for the regulation of osmotic pressure.

Pharmaceutically acceptable salts of the instant compounds, where they can be prepared, are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. If the parent compound is a base it is treated with an excess of an organic or inorganic acid in a suitable solvent. If the parent compound is an acid, it is treated with an inorganic or organic base in a suitable solvent.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

Dosage

The dosage requirements will vary with the particular drug composition employed, the route of administration and the particular subject being treated. It will also be recognized by one of skill in the art that the optimal quantity and spacing of individual dosages of a compound will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound given per day for a defined number of days, can be ascertained using conventional course of treatment determination tests.

The daily parenteral dosage regimen may be in the range of about 0.1 to about 100 mg/kg of total body weight, such as 0.1 to 1 mg/kg, 1 to 5 mg/kg, 5 to 10 mg/kg, 10 to 15 mg/kg, 15 to 20 mg/kg, 20 to 30 mg/kg, 30 to 40 mg/kg, 40 to 50 mg/kg, 50 to 60 mg/kg, 60 to 70 mg/kg, 70 to 80 mg/kg, 80 to 90 mg/kg and 90 to 100 mg/kg of total body weight. The dosage may be evaluated using a model as described in Example 7 herein, in which a daily dosage of 3.3 or 10 mg/kg is used in mice.

A dosage may be administered once a day, or at a frequency higher or lower than once a day. For example, a dosage may be administered 1, 2, 3, 4, 5, 6, 7, 8, 9 or 10 times a day. Alternatively, a dosage may be administered with intervals of 1, 2, 3, 4, 5, 6, 7, 8, 9, 10, 11, 12, 13 or 14 days, The term "unit dosage form" as used herein refers to physically discrete units suitable as unitary dosages for human and animal subjects, each unit containing a predetermined quantity of a compound, alone or in combination with other agents, calculated in an amount sufficient to produce the desired effect in association with a pharmaceutically acceptable diluent, carrier, or vehicle. The specifications for the unit dosage forms of the present invention depend on the particular compound or compounds employed and the effect to be achieved, as well as the pharmacodynamics associated with each compound in the host. The dose administered should be an "effective amount" or an amount necessary to achieve an "effective level" in the individual patient.

When the "effective level" is used as the preferred endpoint for dosing, the actual dose and schedule can vary, depending on inter-individual differences in pharmacokinetics, drug distribution, and metabolism. The "effective level" can be defined, for example, as the blood or tissue level desired in the patient that corresponds to a concentration of a compound according to the invention.

Administration

The main routes of administration are oral and parenteral in order to introduce a compound into the blood stream to ultimately target the sites of desired action. Oral administration is less preferred for protein compounds of the present invention due to degradation in the gastrointestinal tract. Parenteral administration is any administration route not being the oral/enteral route whereby the compound avoids first-pass degradation in the liver. Accordingly, parenteral administration includes any injections and infusions, for example bolus injection or continuous infusion, such as intravenous administration, intramuscular administration and subcutaneous administration. Furthermore, parenteral administration includes inhalations and topical administration.

As peptides are susceptible to degradation if ingested, parenteral administration is preferred. The peptide of the present invention has a high solubility that show no potential for aggregation, allowing it to be formulated for and administered e.g. intranasally and subcutaneously.

Co-Administration

In one embodiment the present invention relates to co-administration of a peptide, compound or composition according to the present invention, together with one or more other bioactive agents.

In one embodiment the present invention relates to co-administration of a peptide, compound or composition according to the present invention, together with one or more anti-inflammatory drugs.

In one embodiment the present invention relates to co-administration of a peptide, compound or composition according to the present invention, together with one or more anti-rheumatoid drugs.

In one embodiment the present invention relates to co-administration of a peptide, compound or composition according to the present invention, together with one or more anti-neurodegenerative drugs.

It follows, that co-administration should be targeted so that to optimise treatment of the patient; i.e. in a patient with rheumatoid arthritis, a drug approved for this specific purpose may be complemented with the peptide, compound or composition according to the present invention to optimise and improve treatment outcome for the patient. This is regardless of whether the approved drug for the specific purpose is prophylactic, ameliorating or curative.

Kit-of-Parts

The present invention also relates to a kit-of-parts comprising one or more of the peptides, compounds or composition described above, and at least an additional component. Said additional component may be drugs for treatment of an inflammatory condition, diabetes mellitus, a neurodegenerative condition etc.

Inflammatory Disorders

Abnormalities associated with inflammation comprise a large, unrelated group of disorders which underlie a variety of human diseases. The immune system is often involved with inflammatory disorders, demonstrated in both allergic reactions and some myopathies, with many immune system disorders resulting in abnormal inflammation. Non-immune diseases with aetiological origins in inflammatory processes are thought to include cancer, atherosclerosis, and ischaemic heart disease. A large variety of proteins are involved in inflammation, and any one of them is open to a genetic mutation which impairs or otherwise deregulates the normal function and expression of that protein.

Shortly after an onset of an infection into organism, IL-1 activates a set of immune system response processes. In particular, IL-1 stimulates fibroblasts proliferation; induces synthesis of proteases, subsequent muscle proteolysis, release of all types of amino acids in blood and stimulates acute phase proteins synthesis; changes the metallic ion content of blood plasma by increasing copper and decreasing zinc and iron concentration in blood; increases blood neutrophils and activates lymphocyte proliferation and induces fever.

It is an aspect of the present invention to provide a peptide according to the present invention for use in the treatment of inflammatory disorders, especially inflammatory disorders wherein IL-1 plays a prominent role.

It is also an aspect of the present invention to provide a peptide according to the present invention for the manufacture of a medicament for the treatment of inflammatory disorders, especially inflammatory disorders wherein IL-1 plays a prominent role.

In a further aspect of the present invention there is provided a method for treatment of an inflammatory disorder, such as an inflammatory disorder wherein IL-1 plays a prominent role, comprising administering a peptide according to the present invention to an individual in need thereof.

In one embodiment of the present invention, an inflammatory disease selected from the group consisting of Acne vulgaris, Asthma, Atherosclerosis, Autoimmune diseases, Behçet's disease, Chronic Inflammation, Chronic prostatitis, Dermatitis, Gout, Glumerulonephritis, Hypersensitives (including type 1 (immediate, or atopic, or anaphylactic) comprising Allergic asthma, Allergic conjunctivitis, Allergic rhinitis (hay fever), Anaphylaxis, Angioedema, Urticaria (hives), Eosinophilia, and response to Penicillin and Cephalosporin; Type 2 (antibody-dependent) comprising Autoimmune hemolytic anemia, Goodpasture's syndrome, Hepatitis, IBS (irritable bowel disease), Juvenile idiopathic arthritis (JIA), Pemphigus, Pernicious anemia (if autoimmune), Psoriasis, Psoriasis Arthritis, Immune thrombocytopenia, Transfusion reactions, Hashimoto's thyroiditis, Interstitial cystitis, Graves disease, Myastenia gravis, Rheumatic fever, Hemolytic disease of the newborn and Acute transplant rejection; Type 3 (immune complex) comprising Rheumatoid arthritis, Immune complex glumerulonephritis, Serum sickness, Subacute, bacterial endocarditis, Symptoms of malaria, Systemic lupus erythematosus (SLE), Arthus reaction, Farmer's lung and Polyarteritis nodosa; Type 4 (cell-mediated or delayed-type hypersensitivity DTH) comprising Contact dermatitis, Atopic dermatitis (eczema), Temporal arteritis, Sarcoidosis, Symptoms of leprosy, Symptoms of tuberculosis, Systemic sclerosis, Mantoux test, Coeliac disease and Chronic transplant rejection), Inflammatory bowel diseases (including Crohn's disease, Ulcerative colitis, Collagenous colitis, Lymphocytic colitis, Ischaemic colitis, Diversion colitis, Behcet's syndrome, Infective colitis and Indeterminate colitis), Myopathies (including dermatomyositis, polymyositis, and inclusion body myositis), Pelvic inflammatory disease, Podagra, Reperfusion Injury, Rheumatoid arthritis, Transplant rejection and Vasculitis, may be subject to use or treatment according to the present invention.

In one embodiment of the present invention, immune diseases selected from the group consisting of Achlorhydra Autoimmune Active Chronic Hepatitis, Acute disseminated encephalomyelitis (ADEM), Acute hemorrhagic leukoencephalitis, Addison's disease, Agammaglobulinemia, Allergies, Alopecia universalis, Amyotrophic Lateral Sclerosis, Anaphylaxis, Ankylosing spondylitis, Antiphospholipid Syndrome, Aplastic anemia, Asthma, Ataxia-Telangiectasia, Autoimmune Diseases, Autoimmune haemolytic anemia, Autoimmune hepatitis, Autoimmune Oophoritis, Behcet's disease, Celiac/Coeliac disease, Chagas' disease, Crohn's disease, Chronic fatigue syndrome, Chronic Granulomatous Disease, Common Variable Immunodeficiency, Diabetes mellitus type 1, DiGeorge Syndrome, Dysautonomia, Electrosensitivity, Endometriosis, Familial Mediterranean Fever, Gestational pemphigoid, Goodpasture's syndrome, Graft vs Host Disease, Graves' disease, Guillain-Barré syndrome (GBS), Hashimoto's disease, Hidradenitis suppurativa, HIV Infections, Hyper-IgM syndrome, Hypersensitivity, IgA Deficiency, Idiopathic thrombocytopenic purpura, IgG Subclass Deficiency, Immune Complex Diseases, Immune System Diseases, Immunologic Deficiency Syndromes, Intestinal cystitis, Kawasaki's disease, Lambert-Eaton Myasthenic Syndrome, Lyme disease, Lymphoproliferative Disorders, Mixed connective tissue disease, Morphea, Multiple Chemical Sensitivity, Multiple sclerosis (MS), Myasthenia gravis, Narcolepsy, Neuromyotonia, Opsoclonus myoclonus syndrome (OMS), Optic neuritis, Ord's thyroiditis, Pemphigus, Pernecious anemia, Polymyositis, polyarticular Arthritis, Primary biliary cirrhosis, Psoriasis, Psoriatic arthritis, Purpura, Rheumatoid arthritis (RA), Reiter's syndrome, Samter's Syndrome, Sarcoidosis, Schizophrenia, Schoenlein-Henoch, Scleroderma, Selective IgA deficiency, Severe Combined Immunodeficiency (SCID), Sick Building Syndrome, Sjogren's Syndrome, Systemic lupus erythromatosus (SLE), Takayasu's arteritis (giant cell arteritis), Ulcerative colitis, Uveitis, Vitiligo, Vulvodynia, Warm autoimmune hemolytic anemia, Wegener's granulomatosis and Wiskott-Aldrich Syndrome, may be subject to use or treatment according to the present invention.

Rheumatoid Arthritis

It is an aspect of the present invention to provide a peptide according to the present invention for use in the treatment of rheumatoid arthritis.

It is also an aspect of the present invention to provide a peptide according to the present invention for the manufacture of a medicament for the treatment of rheumatoid arthritis.

In a further aspect of the present invention there is provided a method for treatment of rheumatoid arthritis, comprising administering a peptide according to the present invention to an individual in need thereof.

Rheumatoid arthritis (RA) is a chronic, systemic inflammatory disorder that may affect many tissues and organs, but principally attacks synovial joints. The pathological process produces an inflammatory response of the synovium (synovitis) secondary to hyperplasia of synovial cells, excess synovial fluid, and the development of pannus (abnormal layer of fibrovascular tissue or granulation tissue) in the synovium. The pathology of the disease process often leads to the destruction of articular cartilage and ankylosis (stiffness) of the joints. Rheumatoid arthritis can also produce diffuse inflammation in the lungs, pericardium, pleura, and sclera, and also nodular lesions, most common in subcutaneous tissue. Although the cause of rheumatoid arthritis is unknown, autoimmunity plays a pivotal role in both its chronicity and progression, and RA is considered a systemic autoimmune disease.

About 1% of the world's population is afflicted by rheumatoid arthritis, women three times more often than men. Onset is most frequent between the ages of 40 and 50, but people of any age can be affected. It can be a disabling and painful condition, which can lead to substantial loss of functioning and mobility if not adequately treated. It is a clinical diagnosis made on the basis of symptoms, physical examination, radiographs (X-rays) and labs.

Various treatments are available today. Non-pharmacological treatment includes physical therapy, orthoses, occupational therapy and nutritional therapy but do not stop progression of joint destruction. Analgesia and anti-inflammatory drugs, including steroids, are used to suppress the symptoms, while disease-modifying antirheumatic drugs (DMARDs) are required to inhibit or halt the underlying immune process and prevent long-term damage. In recent times, the newer group of biologics has increased treatment options.

Gout/Podagra

It is an aspect of the present invention to provide a peptide according to the present invention for use in the treatment of gout and/or podagra.

It is also an aspect of the present invention to provide a peptide according to the present invention for the manufacture of a medicament for the treatment of gout and/or podagra.

In a further aspect of the present invention there is provided a method for treatment of gout and/or podagra, comprising administering a peptide according to the present invention to an individual in need thereof.

Gout (also known as podagra when it involves the big toe) is a medical condition usually characterized by recurrent attacks of acute inflammatory arthritis—a red, tender, hot, swollen joint. The metatarsal-phalangeal joint at the base of the big toe is the most commonly affected (~50% of cases). However, it may also present as tophi (deposit of monosodium urate crystals), kidney stones, or urate nephropathy. It is caused by elevated levels of uric acid in the blood which crystallize and are deposited in joints, tendons, and surrounding tissues. Diagnosis is confirmed clinically by the visualization of the characteristic crystals in joint fluid.

Gout has increased in frequency in recent decades affecting approximately 1-2% of the Western population at some point in their lives. The increase is believed to be due to increasing risk factors in the population, such as metabolic syndrome, longer life expectancy and changes in diet.

Current treatment modalities include nonsteroidal anti-inflammatory drugs (NSAIDs), steroids, or colchicine to improve symptoms. Once the acute attack has subsided, levels of uric acid are usually lowered via lifestyle changes, and in those with frequent attacks allopurinol or probenicid provide long-term prevention.

JIA (Juvenile Idiopathic Arthritis)

It is an aspect of the present invention to provide a peptide according to the present invention for use in the treatment of JIA.

It is also an aspect of the present invention to provide a peptide according to the present invention for the manufacture of a medicament for the treatment of JIA.

In a further aspect of the present invention there is provided a method for treatment of JIA, comprising administering a peptide according to the present invention to an individual in need thereof.

Juvenile idiopathic arthritis (JIA) is the most common form of persistent arthritis in children. Juvenile in this context refers to an onset before age 16, idiopathic refers to a condition with no defined cause, and arthritis is the inflammation of the synovium of a joint. JIA is a subset of arthritis seen in childhood, which may be transient and self-limited, or chronic. It differs significantly from arthritis commonly seen in adults (osteoarthritis, rheumatoid arthritis), and other types of arthritis that can present in childhood which are chronic conditions (e.g. psoriatic arthritis and ankylosing spondylitis). JIA is an autoimmune disease.

Diabetes Mellitus

It is an aspect of the present invention to provide a peptide according to the present invention for use in the treatment of diabetes mellitus.

It is also an aspect of the present invention to provide a peptide according to the present invention for the manufacture of a medicament for the treatment of diabetes mellitus.

In a further aspect of the present invention there is provided a method for treatment of diabetes mellitus, comprising administering a peptide according to the present invention to an individual in need thereof.

In one embodiment, said diabetes mellitus is diabetes mellitus type I. In another embodiment, said diabetes mellitus is diabetes mellitus type II.

Diabetes mellitus is a group of metabolic diseases in which a person has high blood sugar, either because the body does not produce enough insulin, or because cells do not respond to the insulin that is produced. This high blood sugar produces the classical symptoms of polyuria (frequent urination), polydipsia (increased thirst) and polyphagia (increased hunger).

Type 1 diabetes: results from the body's failure to produce insulin, and presently requires the person to inject insulin. (Also referred to as insulin-dependent diabetes mellitus, IDDM for short, and juvenile diabetes.)

Type 1 diabetes mellitus is characterized by loss of the insulin-producing beta cells of the islets of Langerhans in the pancreas leading to insulin deficiency. This type of diabetes can be further classified as immune-mediated or idiopathic. The majority of type 1 diabetes is of the immune-mediated nature, where beta cell loss is a T-cell mediated autoimmune attack.

Type 2 diabetes: results from insulin resistance, a condition in which cells fail to use insulin properly, sometimes combined with an absolute insulin deficiency. (Formerly referred to as non-insulin-dependent diabetes mellitus, NIDDM for short, and adult-onset diabetes.)

Type 2 diabetes mellitus is characterized by insulin resistance which may be combined with relatively reduced insulin secretion. The defective responsiveness of body tissues to insulin is believed to involve the insulin receptor. Type 2 diabetes is due primarily to lifestyle factors and genetics.

Gestational diabetes: is when pregnant women, who have never had diabetes before, have a high blood glucose level during pregnancy. It may precede development of type 2 DM.

Other forms of diabetes mellitus include congenital diabetes, which is due to genetic defects of insulin secretion, cystic fibrosis-related diabetes, steroid diabetes induced by high doses of glucocorticoids, and several forms of monogenic diabetes.

Diabetes without proper treatments can cause many complications. Acute complications include hypoglycemia, diabetic ketoacidosis, or nonketotic hyperosmolar coma. Serious long-term complications include cardiovascular disease, chronic renal failure and retinal damage. Adequate treatment of diabetes is thus important, as well as blood pressure control and lifestyle factors such as smoking cessation and maintaining a healthy body weight.

As of 2000 at least 171 million people worldwide suffer from diabetes, or 2.8% of the population. Type 2 diabetes is by far the most common, affecting 90 to 95% of the U.S. diabetes population Behçet's disease It is an aspect of the present invention to provide a peptide according to the present invention for use in the treatment of Behçet's disease.

It is also an aspect of the present invention to provide a peptide according to the present invention for the manufacture of a medicament for the treatment of Behçet's disease.

In a further aspect of the present invention there is provided a method for treatment of Behçet's disease, comprising administering a peptide according to the present invention to an individual in need thereof.

Behçet's disease is a rare, systemic, form of vasculitis (or inflammation of the blood vessels) that often presents with mucous membrane ulceration, and ocular involvements (involvement of the eyes). Ocular involvement can be in the form of posterior uveitis, anterior uveitis, or retinal vasculitis. As a systemic disease, it also involves visceral organs such as the gastrointestinal tract, pulmonary, musculoskeletal, and neurological systems. This syndrome can be fatal; death can be caused by complicated rupture of the vascular aneurysms, or severe neurological complications, and therefore immediate medical treatment is necessary.

Neurodegenerative Disorders

It is an aspect of the present invention to provide a peptide according to the present invention for use in the treatment of a neurodegenerative disorder.

It is also an aspect of the present invention to provide a peptide according to the present invention for the manufacture of a medicament for the treatment of a neurodegenerative disorder.

In a further aspect of the present invention there is provided a method for treatment of a neurodegenerative disorder, comprising administering a peptide according to the present invention to an individual in need thereof.

Particularly, said neurodegenerative disorder has a neuroinflammatory component and is selected from the group consisting of Alzheimer's disease, Parkinson's disease, Huntington's disease and Multiple Sclerosis. Especially, said neurodegenerative disorder may be those wherein IL-1 has a prominent role.

The brain is an immunologically privileged site under normal conditions. Suppression factors of the immune response include neurotransmitters, neurohormones, neurotrophic factors, anti-inflammatory factors, and cell-cell contacts via adhesion molecules or CD200. However, no single factor can fully account for immune control. Augmented cerebral immune responses observed in neurodegenerative diseases probably reflect stimulatory signals that override suppressive signals. However, the suppression of immune responses is not always beneficial to neurons in degenerative conditions (Chang et al., 2009). Thus, therapeutic interventions in neurodegenerative diseases should help re-establish the appropriate control of immune cells/microglia in the CNS.

Neurodegenerative diseases are a growing cause of disability in the aging community. Alzheimer's disease (AD) is the most common neurodegenerative disorder. The annual incidence of AD worldwide is estimated to be 4.6 million cases, with one new case every 7 s. By the year 2040, 80 million cases worldwide are expected (Massoud and Gauthier, 2010). Neurodegeneration; the slow progression of dysfunction with a loss of neurons and axonal connections in the central nervous system (CNS), is the primary pathological characteristic of such neurological disorders as AD, Parkinson's disease (PD) and Huntington's disease (HD) (Heneka et al., 2010). In AD, the main characteristics of neuroinflammation include microglial activation in regions associated with Aβ (amyloid beta) deposition and the expression of a variety of proinflammatory cytokines, such as IL1β and tumor necrosis factor α (TNFα). The ratio of the proinflammatory IL1β to the anti-inflammatory IL10 is markedly increased in serum in AD patients. The local inflammatory reaction in AD is sustained by activated microglia and reactive astrocytes. Microglial activation can either be neuroprotective or damaging. An acute neuroinflammatory response is generally beneficial to the CNS, minimizing further injury and contributing to the repair of damaged tissue, whereas chronic inflammation is detrimental and damaging to the nervous system. The progressive deposition of Aβ in AD is known to be chemoattractive for microglia and might therefore provide a chronic stimulus to microglial cells. A non-steroidal anti-inflammatory drug, ibuprofen, has recently been shown to be protective in AD (Heneka et al., 2010; Krause and Müller, 2010).

The implication of the IL1 system in neurodegeneration is supported by the following lines of evidence. Its expression is enhanced dramatically and rapidly following any type of brain injury. All chronic neurodegenerative diseases are accompanied by an increase in IL1 expression. Moreover, neuroinflammation mediated by IL1β increases the susceptibility of neurons to degeneration. Microglial cells are the main source of IL1β in neuroinflammation, although its production is also induced in astrocytes. Decreased levels of IL1Ra have been found in AD patients. Blocking IL1 signaling by increasing the amounts of IL1Ra following brain lesions results in improved outcomes in many experimental models of neurodegeneration. IL1Ra consistently provides neuroprotection. IL1Ra has been shown to penetrate the human brain at experimentally therapeutic concentrations, and clinical trials for introducing IL1Ra as a post-stroke therapy have been designed (Cawthorne et al., 2011; Clark et al., 2008; Koprich et al., 2008; Spulber et al., 2009; Tarkowski et al., 2001).

Alzheimer's Disease

It is an aspect of the present invention to provide a peptide according to the present invention for use in the treatment of Alzheimer's disease.

It is also an aspect of the present invention to provide a peptide according to the present invention for the manufacture of a medicament for the treatment of Alzheimer's disease.

In a further aspect of the present invention there is provided a method for treatment of Alzheimer's disease, comprising administering a peptide according to the present invention to an individual in need thereof.

Alzheimer's disease (AD) is the most common form of dementia. Most often, it is diagnosed in people over 65 years of age, although the less-prevalent early-onset Alzheimer's can occur much earlier. In 2006, there were 26.6 million sufferers worldwide. Alzheimer's is predicted to affect 1 in 85 people globally by 2050.

Although the course of Alzheimer's disease is unique for every individual, there are many common symptoms. The earliest observable symptoms are often mistakenly thought to be 'age-related' concerns, or manifestations of stress. In the early stages, the most commonly recognised symptom is inability to acquire new memories, such as difficulty in recalling recently observed facts. As the disease advances, symptoms include confusion, irritability and aggression, mood swings, language breakdown, long-term memory loss, and the general withdrawal of the sufferer as their senses decline.

Gradually, bodily functions are lost, ultimately leading to death. The mean life expectancy following diagnosis is approximately seven years.

Alzheimer's disease is characterised by loss of neurons and synapses in the cerebral cortex and certain subcortical regions. This loss results in gross atrophy of the affected regions, including degeneration in the temporal lobe and parietal lobe, and parts of the frontal cortex and cingulate gyrus. Both amyloid plaques and neurofibrillary tangles are clearly visible by microscopy in brains of those afflicted by AD. Plaques are dense, mostly insoluble deposits of amyloid-beta peptide and cellular material outside and around neurons. Tangles (neurofibrillary tangles) are aggregates of the microtubule-associated protein tau which has become hyperphosphorylated and accumulate inside the cells themselves.

Parkinson's Disease

It is an aspect of the present invention to provide a peptide according to the present invention for use in the treatment of Parkinson's disease.

It is also an aspect of the present invention to provide a peptide according to the present invention for the manufacture of a medicament for the treatment of Parkinson's disease.

In a further aspect of the present invention there is provided a method for treatment of Parkinson's disease, comprising administering a peptide according to the present invention to an individual in need thereof.

Parkinson's disease (PD) is a degenerative disorder of the central nervous system. It results from the death by unknown causes of the dopamine-containing cells of the substantia nigra, which is a region of the midbrain. Early in the course of the disease, the most obvious symptoms are movement-related, including shaking, rigidity, slow-ness of movement and difficulty with walking and gait. Later, cognitive and behavioral problems may arise, with dementia commonly occurring in the advanced stages of the disease. Other symptoms include sensory, sleep and emotional problems. PD is more common in the elderly with most cases occurring after the age of 50 years.

The pathology of the disease is characterized by the accumulation of a protein called alpha-synuclein into inclusions called Lewy bodies in neurons, and from insufficient formation and activity of dopamine produced in certain neurons of parts of the midbrain.

Modern treatments are effective at managing the early motor symptoms of the disease, mainly through the use of levodopa and dopamine agonists. As the disease progresses and dopamine neurons continue to be lost, a point eventually arrives at which these drugs become ineffective at treating the symptoms, while at the same time produce a complication called dyskinesia, marked by writhing movements. Medications to treat other symptoms of PD exist. Diet and some forms of rehabilitation have shown some effectiveness at alleviating symptoms. Surgery and deep brain stimulation have been used to reduce motor symptoms as a last resort in severe cases where drugs are ineffective.

Huntingtons Disease

It is an aspect of the present invention to provide a peptide according to the present invention for use in the treatment of Huntington's disease.

It is also an aspect of the present invention to provide a peptide according to the present invention for the manufacture of a medicament for the treatment of Huntington's disease.

In a further aspect of the present invention there is provided a method for treatment of Huntington's disease, comprising administering a peptide according to the present invention to an individual in need thereof.

Huntington's disease, chorea, or disorder (HD), is a neurodegenerative genetic disorder that affects muscle coordination and leads to cognitive decline and dementia. It typically becomes noticeable in middle age. HD is the most common genetic cause of abnormal involuntary writhing movements called chorea and is much more common in people of Western European descent than in those from Asia or Africa. The disease is caused by an autosomal dominant mutation on either of an individual's two copies of a gene called Huntingtin. Physical symptoms of Huntington's disease can begin at any age from infancy to old age, but usually begin between 35 and 44 years of age. About 6% of cases start before the age of 21 years with an akinetic-rigid syndrome; they progress faster and vary slightly. The variant is classified as juvenile, akinetic-rigid or Westphal variant HD.

The Huntingtin gene (HTT) codes for the protein Huntingtin (Htt). Part of this gene is a repeated section called a trinucleotide repeat, which varies in length between individuals and may change length between generations. When the length of this repeated section reaches a certain threshold, it produces an altered form of the protein, called mutant Huntingtin protein (mHtt). The differing functions of these proteins are the cause of pathological changes which in turn cause the disease symptoms as the mutated protein results in gradual damage to specific areas of the brain.

Symptoms of the disease can vary between individuals and even members of the same family, but the symptoms progress predictably for most individuals. The earliest symptoms are a general lack of coordination and an unsteady gait. As the disease advances, uncoordinated, jerky body movements become more apparent, along with a decline in mental abilities and behavioral and psychiatric problems. Physical abilities are gradually impeded until coordinated movement becomes very difficult, and mental abilities generally decline into dementia. Complications such as pneumonia, heart disease, and physical injury from falls reduce life expectancy to around twenty years after symptoms begin.

There is no cure for HD, and full-time care is required in the later stages of the disease, but there are emerging treatments to relieve some of its symptoms.

Multiple Sclerosis

It is an aspect of the present invention to provide a peptide according to the present invention for use in the treatment of Multiple sclerosis.

It is also an aspect of the present invention to provide a peptide according to the present invention for the manufacture of a medicament for the treatment of Multiple sclerosis.

In a further aspect of the present invention there is provided a method for treatment of Multiple sclerosis, comprising administering a peptide according to the present invention to an individual in need thereof.

Multiple sclerosis (MS, also known as disseminated sclerosis or encephalomyelitis disseminata) is an inflammatory disease in which the fatty myelin sheaths around the axons of the brain and spinal cord are damaged, leading to demyelination and scarring as well as a broad spectrum of signs and symptoms. Disease onset usually occurs in young adults, and it is more common in females. It has a prevalence that ranges between 2 and 150 per 100,000.

MS affects the ability of nerve cells in the brain and spinal cord to communicate with each other. Nerve cells communicate by sending electrical signals called action potentials down long fibers called axons, which are wrapped in an insulating substance called myelin. In MS, the body's own immune system attacks and damages the myelin. When myelin is lost, the axons can no longer effectively conduct signals. The name multiple sclerosis refers to scars (scleroses—better known as plaques or lesions) particularly in the white matter of the brain and spinal cord, which is mainly composed of myelin.

Almost any neurological symptom can appear with the disease, and often progresses to physical and cognitive disability. MS takes several forms, with new symptoms occurring either in discrete attacks (relapsing forms) or slowly accumulating over time (progressive forms). Between attacks, symptoms may go away completely, but permanent neurological problems often occur, especially as the disease advances.

There is no known cure for Multiple sclerosis. Treatments attempt to return function after an attack, prevent new attacks, and prevent disability. MS medications can have adverse effects or be poorly tolerated, and many patients pursue alternative treatments, despite the lack of supporting scientific study. Life expectancy of patients is 5 to 10 years lower than that of the unaffected population Sequences Amino acid sequence of the Interleukin-1 receptor antagonist protein (full-length; SEQ ID NO:28)
UniProt Accession No.: P18510 (IL1RA_HUMAN)
Short names: IL-1RN, IL1RN, IL-1ra, IRAP, IL1F3, IL1RA.
Alternative name(s): ICIL-1RA, IL1 inhibitor, INN=Anakinra
4 isoforms (1 secreted, 3 cytoplasm).
Isoform 1 (identifier: P18510-1), 177 amino acids long, has been chosen as the 'canonical' sequence:

```
                                            (SEQ ID NO: 28)
MEICRGLRSHLITLLLFLFHSETICRPSGRKSSKMQAFRIWDVNQKTFY
LRNNQLVAGYLQGPNVNLEEKIDVVPIEPHALFLGIHGGKMCLSCVKSG
DETRLQLEAVNITDLSENRKQDKRFAFIRSDSGPTTSFESAACPGWFLC
TAMEADQPVSLTNMPDEGVMVTKFYFQEDE
```

The Sequence of Ilantafin-8/Ilantafin (SEQ ID NO:1) is underlined.

Isoform 2 (identifier: P18510-2), 159 aa long (Also known as: icIL-1ra)

The sequence of this isoform differs from the canonical sequence as follows:

```
    aa 1-21: MEICRGLRSHLITLLLFLFHS → MAL
```

Isoform 3 (identifier: P18510-3), 180 aa long (Also known as: icIL-1ra type II)

The sequence of this isoform differs from the canonical sequence as follows:

```
aa 1-21:
MEICRGLRSHLITLLLFLFHS → MALADLYEEGGGGGEGEDNADSK
```

Isoform 4 (identifier: P18510-4), 143 aa long
The sequence of this isoform differs from the canonical sequence as follows: aa 1-34: Missing (deleted).
Further Ilantafin-Sequences (Fragments of IL1RA)
Ilantafin-1: RIWDVNQKT (SEQ ID NO:29)
Ilantafin-2: AGYLQGPNVN (SEQ ID NO:30)—soluble in water, not soluble in PBS or medium
Ilantafin-3: NQLVAGYLQGPNVN (SEQ ID NO:31)—not soluble in water
Ilantafin-4: VTKFYFQED (SEQ ID NO:32)—not soluble in water
Ilantafin-5: EGVMVTKFYFQED (SEQ ID NO:33)—completely insoluble when produced
Ilantafin-6: NQKTFYLRNNQL (SEQ ID NO:34)—soluble in water, not soluble in PBS or medium
Ilantafin-7: TAMEADQPVS (SEQ ID NO:35)
Ilantafin-8: Is Ilantafin, SEQ ID NO:1
Ilantafin-9: GPNAKLEEKA (SEQ ID NO:36)

EXAMPLES

Example 1

Location of the Ilantafin (Ilantide) sequence motif (SEQ ID NO:1) in the crystal structure of the complex of human IL1Ra and human IL1RI (FIG. 1).
Method:
Mapping of the location of the peptide was performed employing PyMOL™ software, based on PyMOL v0.99 (DeLano Scientific LLC, South San Francisco, Calif., U.S.A). This was done based on the crystal structure of the complex of human ILRa and human IL1RI, PDB ID: 1IRA (Schreuder et al., 1997).

Example 2

Figure 2A:
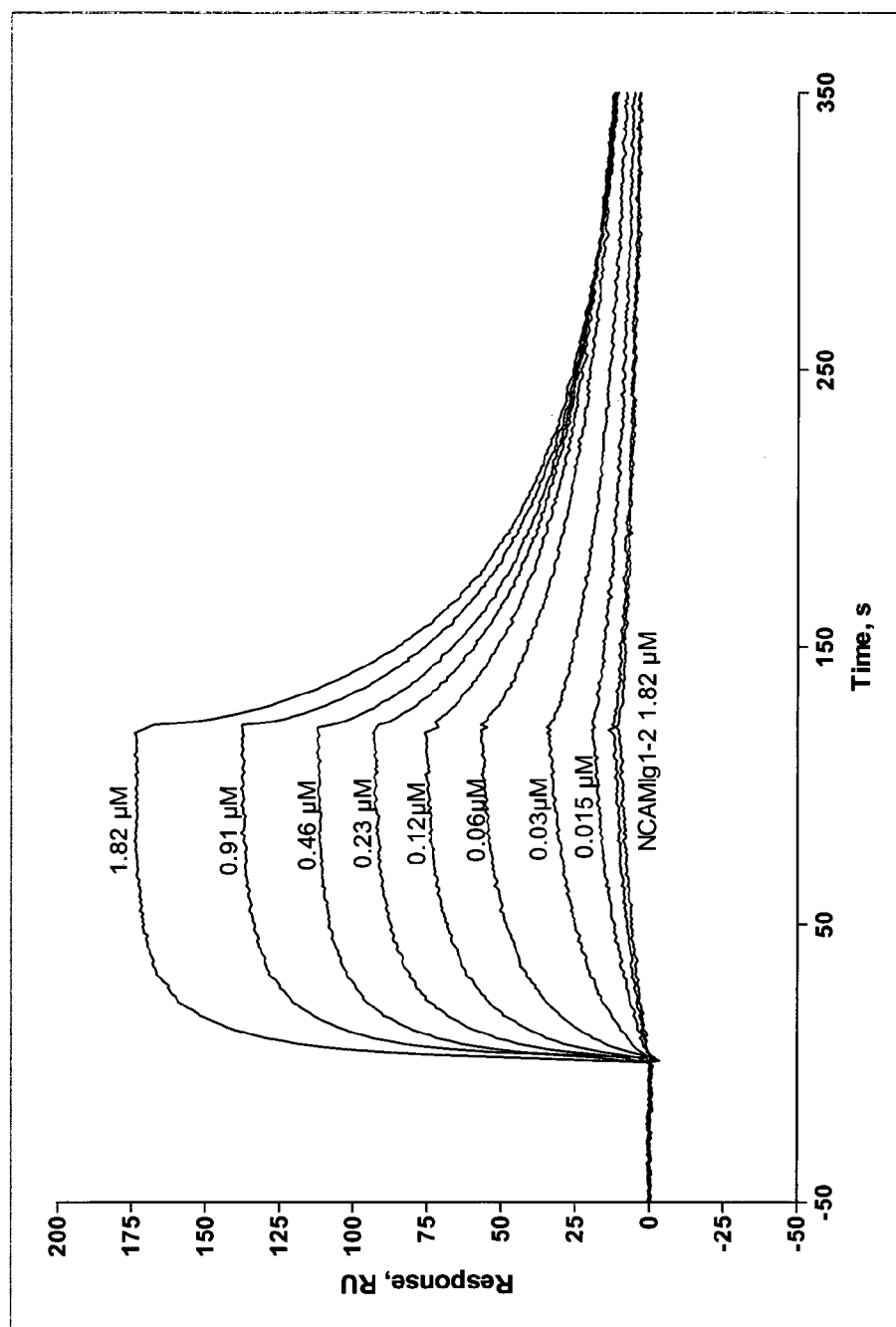
FIGS. 2A-2C show binding of IL1β (FIG. 2A), IL1Ra (FIG. 2B) and the Ilantafin peptide (SEQ ID NO:1, FIG. 2C) to the immobilized on a sensor chip IL1RI employing surface plasmon resonance (SPR) analysis. RU—resonance units.
Figure 2B:
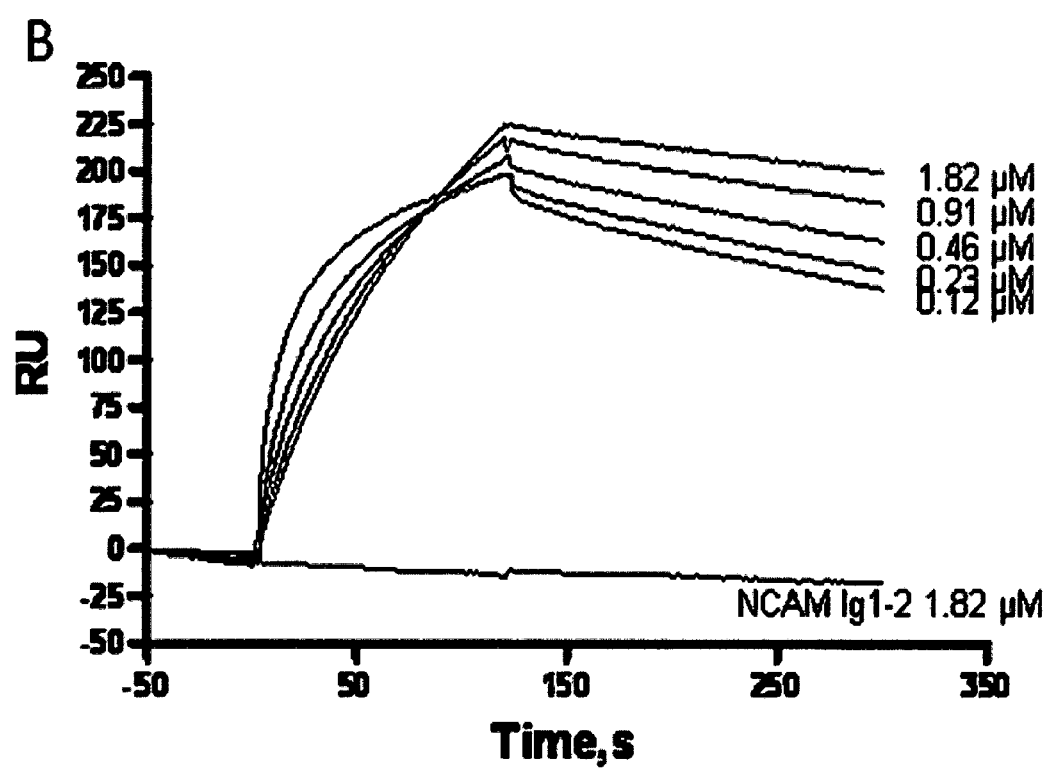
Figure 2C:
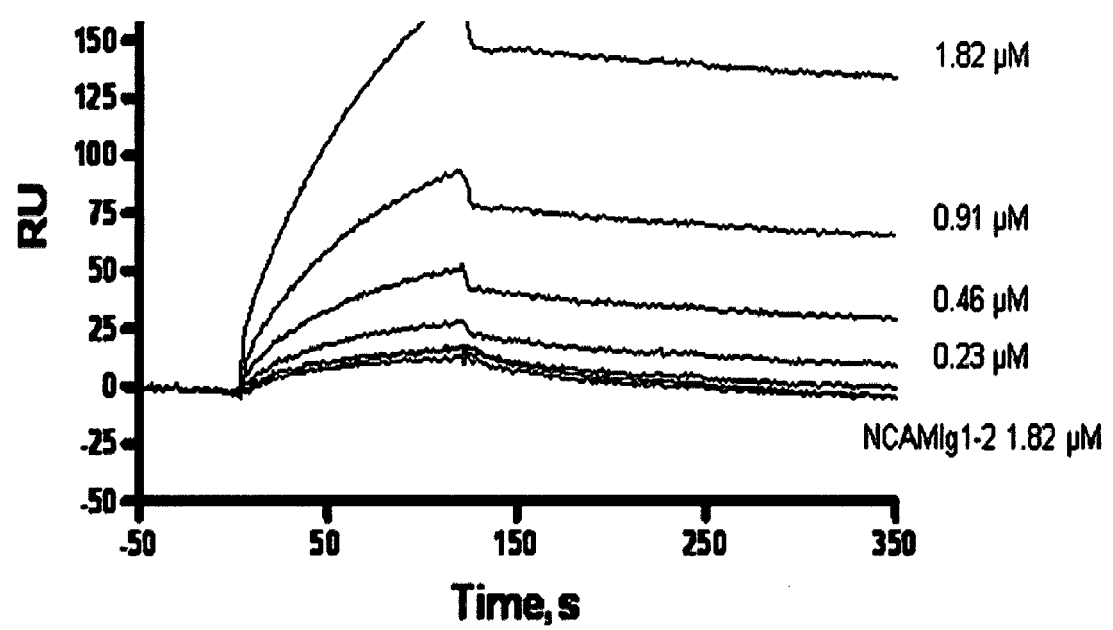
Figure 4:
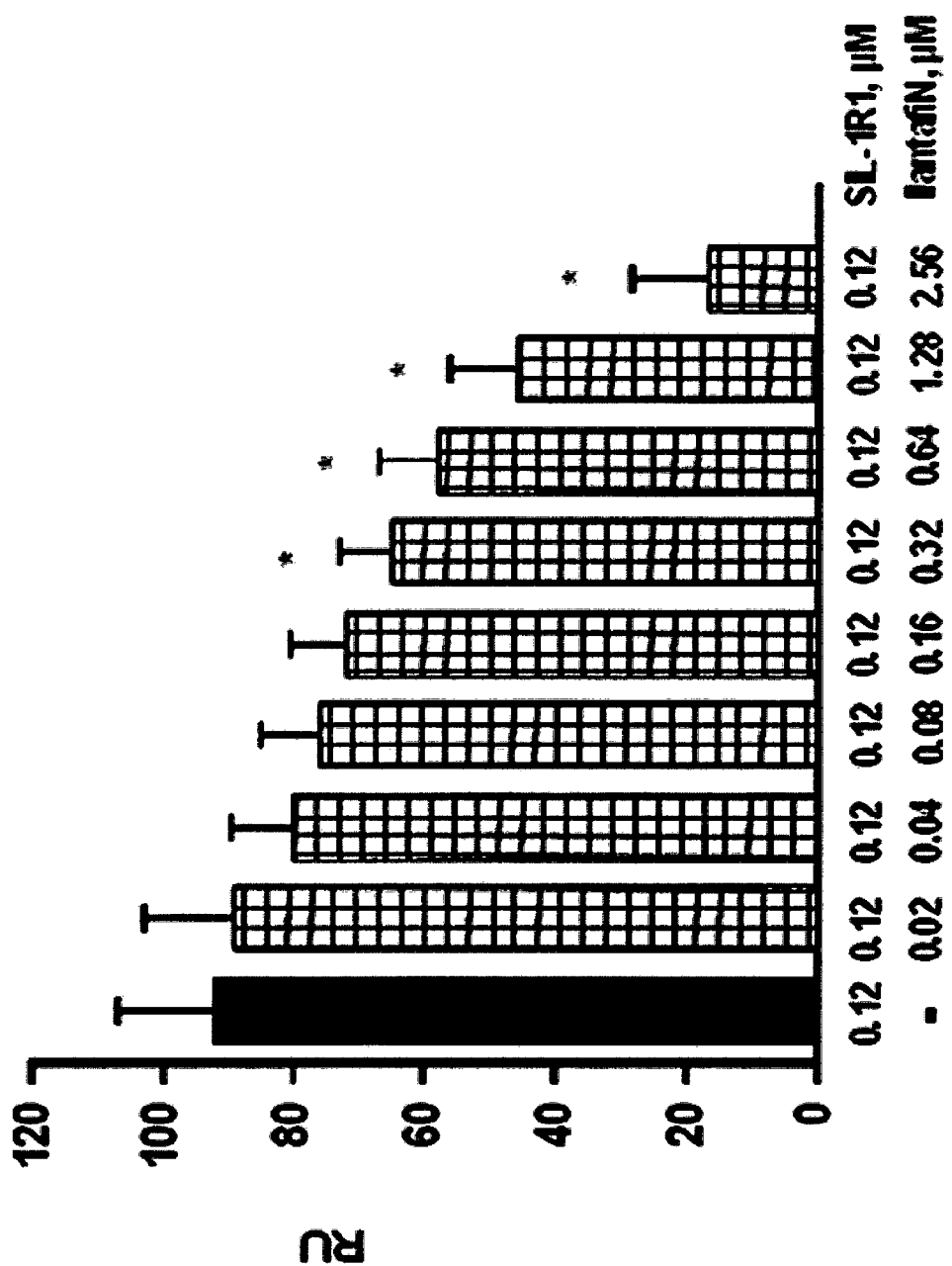
FIG. 4 shows competition between soluble IL1RI (SILR1) and the Ilantafin peptide (SEQ ID NO:1) for binding to the immobilized IL1β. *p<0.05, when compared to the binding of SILR1 alone.

The Ilantafin peptide (SEQ ID NO:1) interacts with the immobilized ectodomain of IL1RI with an affinity which is within the same order of magnitude as the binding affinities of IL1β and IL1Ra to IL1RI (FIGS. 2 and 3). Moreover the peptide competes with the receptor for the binding of IL1β (FIG. 3).
Method:
Binding analysis was performed using a BiaCore 2000 Instrument (BiaCore AB, Uppsala, Sweden) at 25° C. using 10 mM sodium phosphate (pH 7.4), 150 mM NaCl as running buffer. The flow-rate was 5 µl/min. Data were analysed by nonlinear curve fitting using the manufacturer's software. The recombinant protein comprising the whole extracellular part of IIL1RI was immobilised on the surface of a CM5 sensor chip by means of electrostatic interactions, and the peptide and the IL1β and IL1Ra proteins were injected at various concentrations. The curves corresponding to the difference between binding to peptides and a blank chip were used for analysis. In FIG. 4, the IL1β protein was immobilized on a sensor chip and the Ilantafin peptide in various concentrations and the soluble receptor (SIL1RI) in a concentration of 0.12 µM were injected.

Example 3

Figure 5:
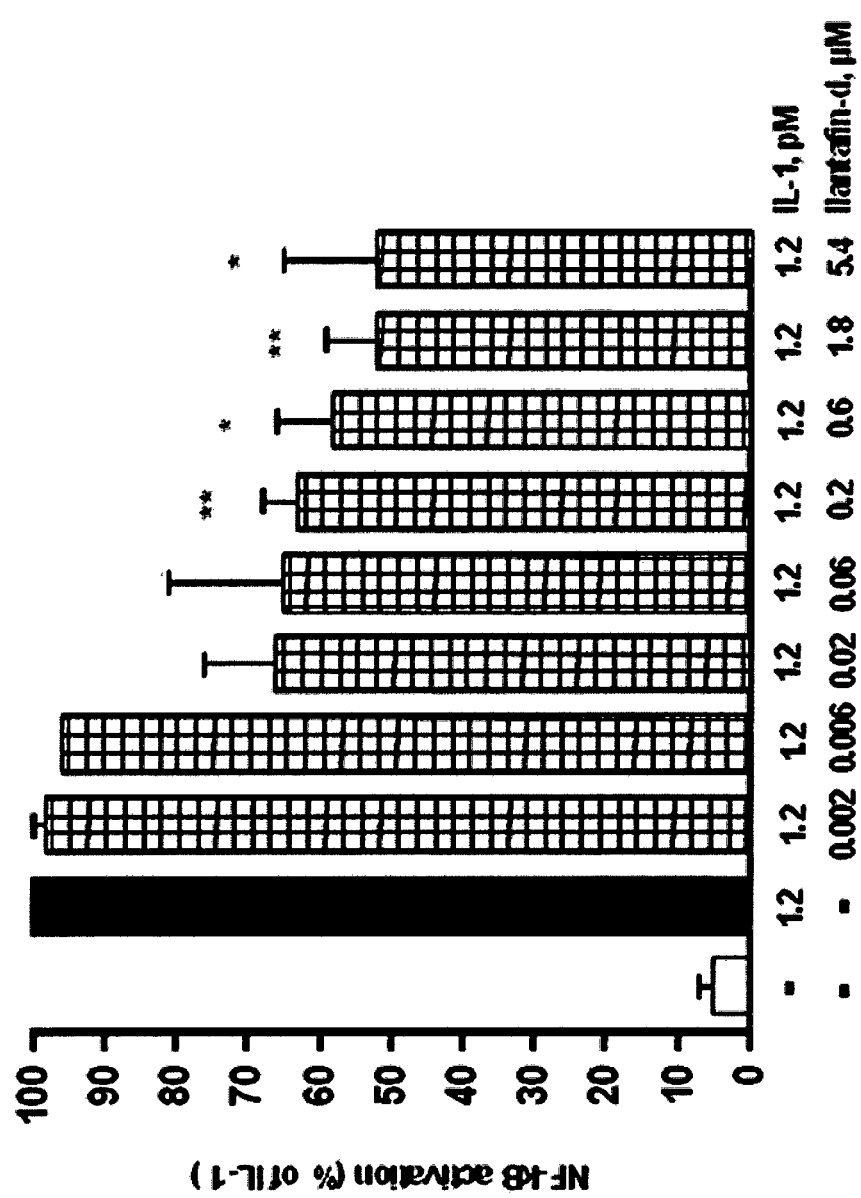
FIG. 5 shows the inhibitory effect of Ilantafin (SEQ ID NO:1) on NF-KB activated by IL1β. The Ilantafin peptide was synthesized as tetrameric dendrimer (Ilantafin-d) attached to a lysine backbone. *p<0.05. **p<0.01, when compared to the black bar.
Figure 6:
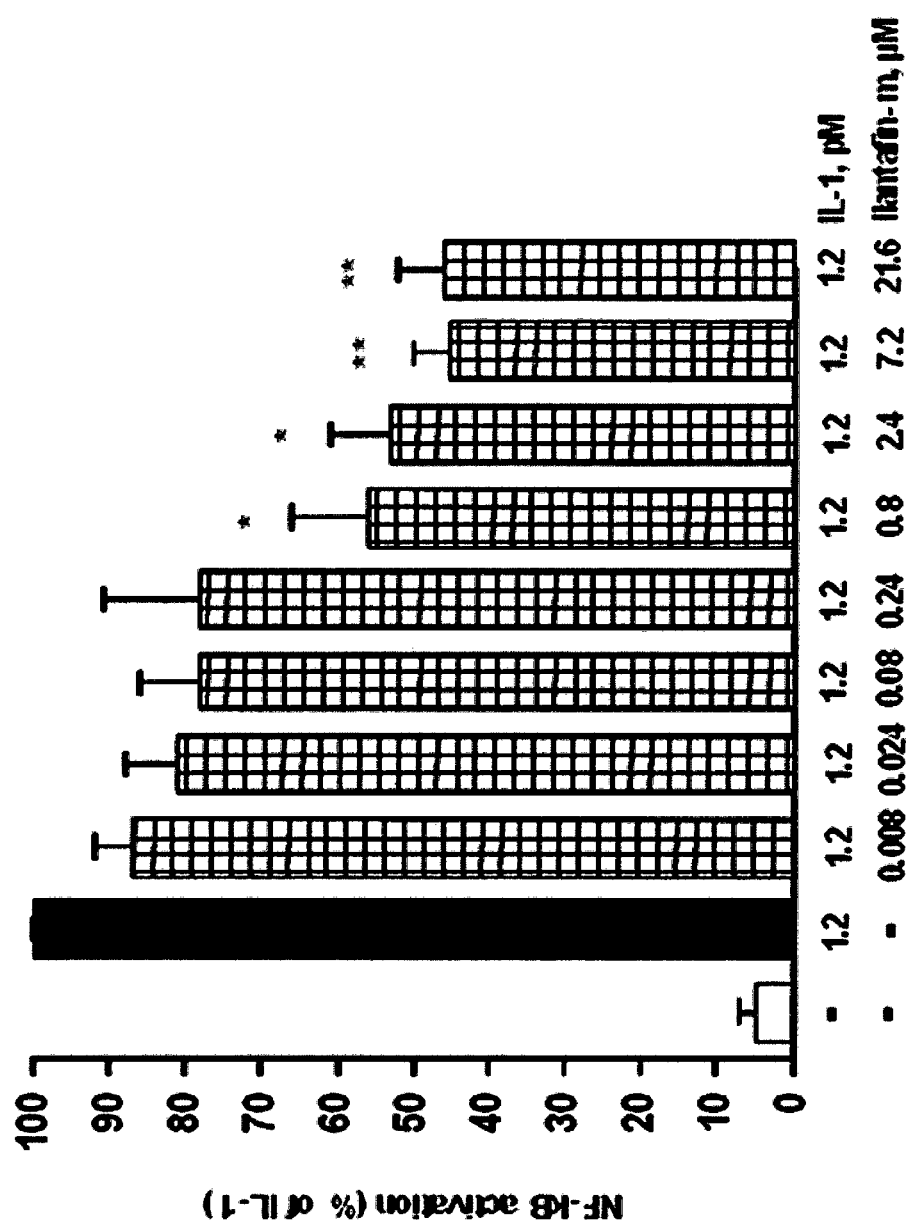
FIG. 6 shows the inhibitory effect of Ilantafin (SEQ ID NO:1) on NF-KB activated by IL1β. The Ilantafin peptide was synthesized as a monomer (Ilantafin-m). *p<0.05, **p<0.01, when compared to the black bar.
Figure 7A:
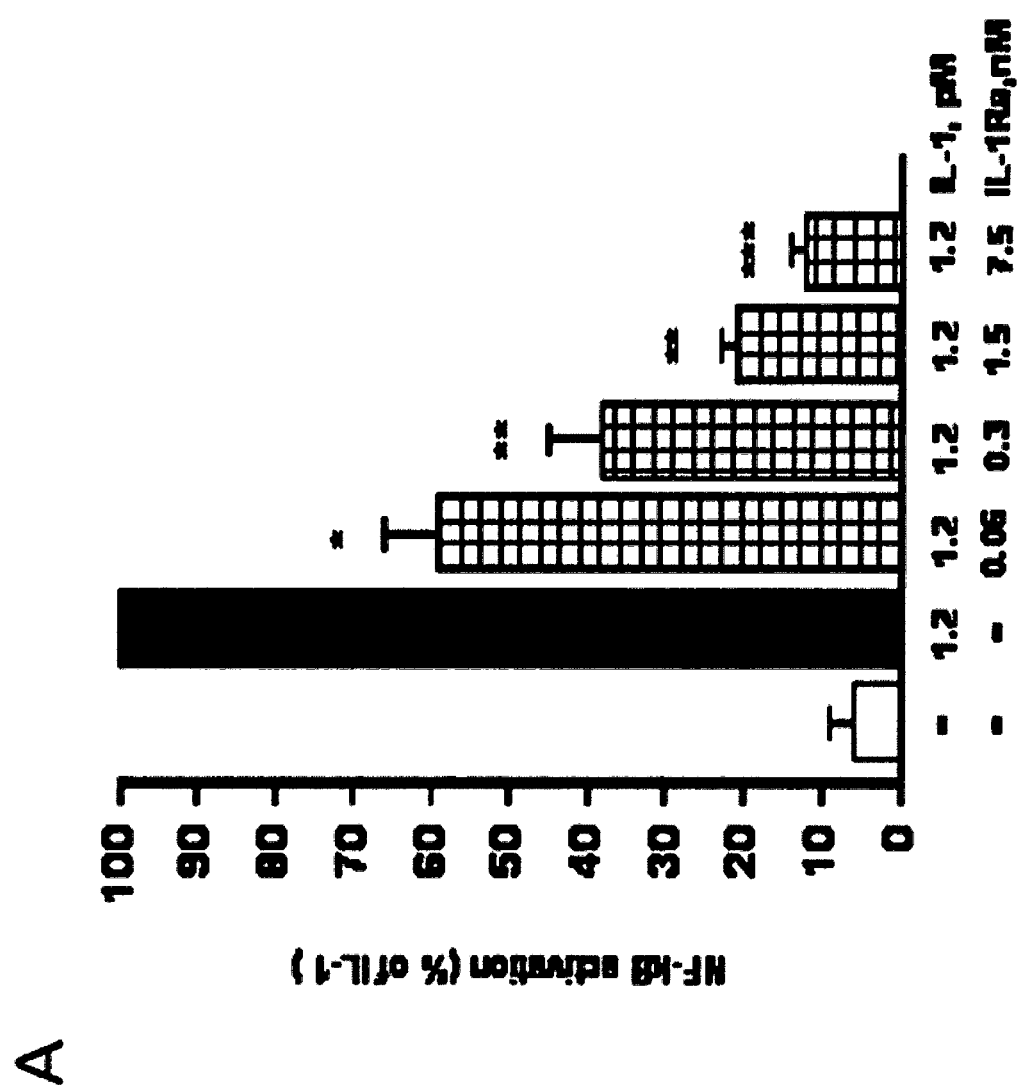
FIGS. 7A-7B show the inhibitory effect of the ILRa (FIG. 7A) and SILR1 (FIG. 7B) proteins on NF-KB activated by IL1β. *p<0.05, p<0.01, *p<0.001, when compared to the black bar.
Figure 7B:
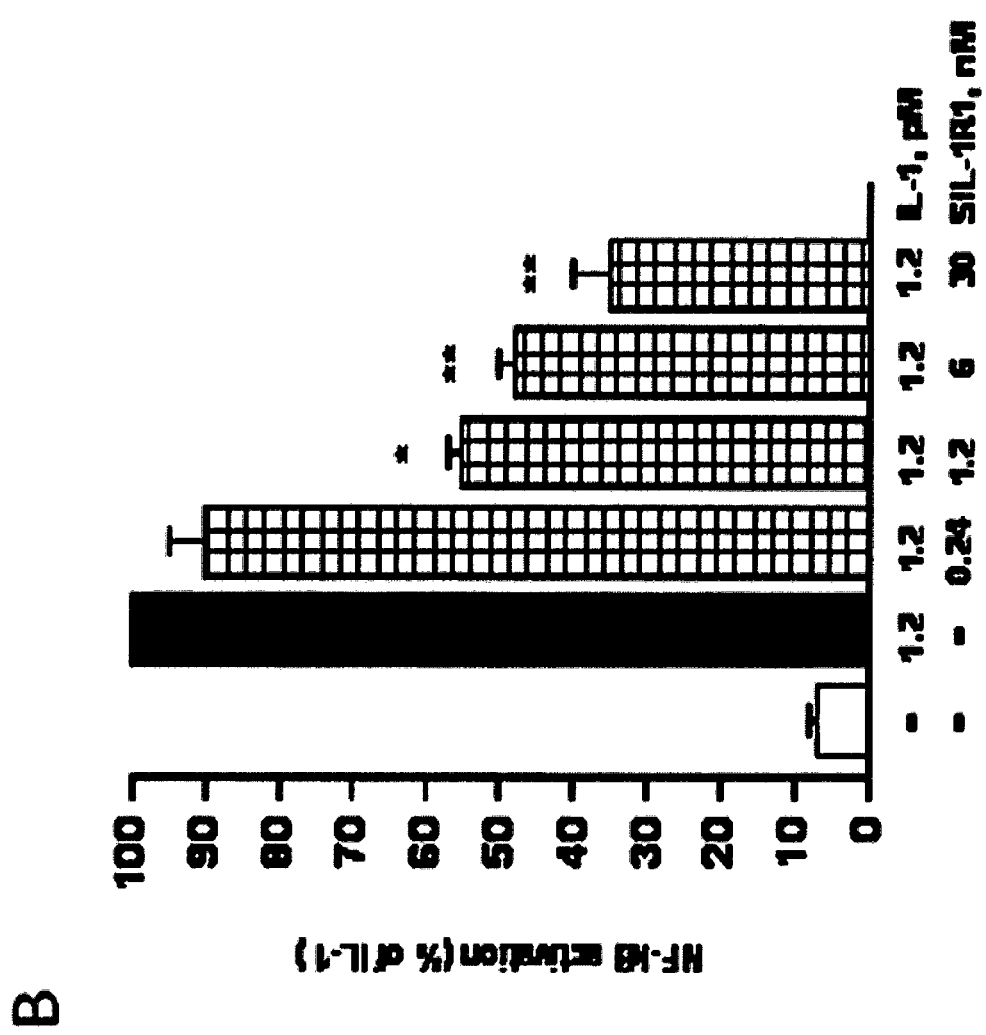
Figure 8:
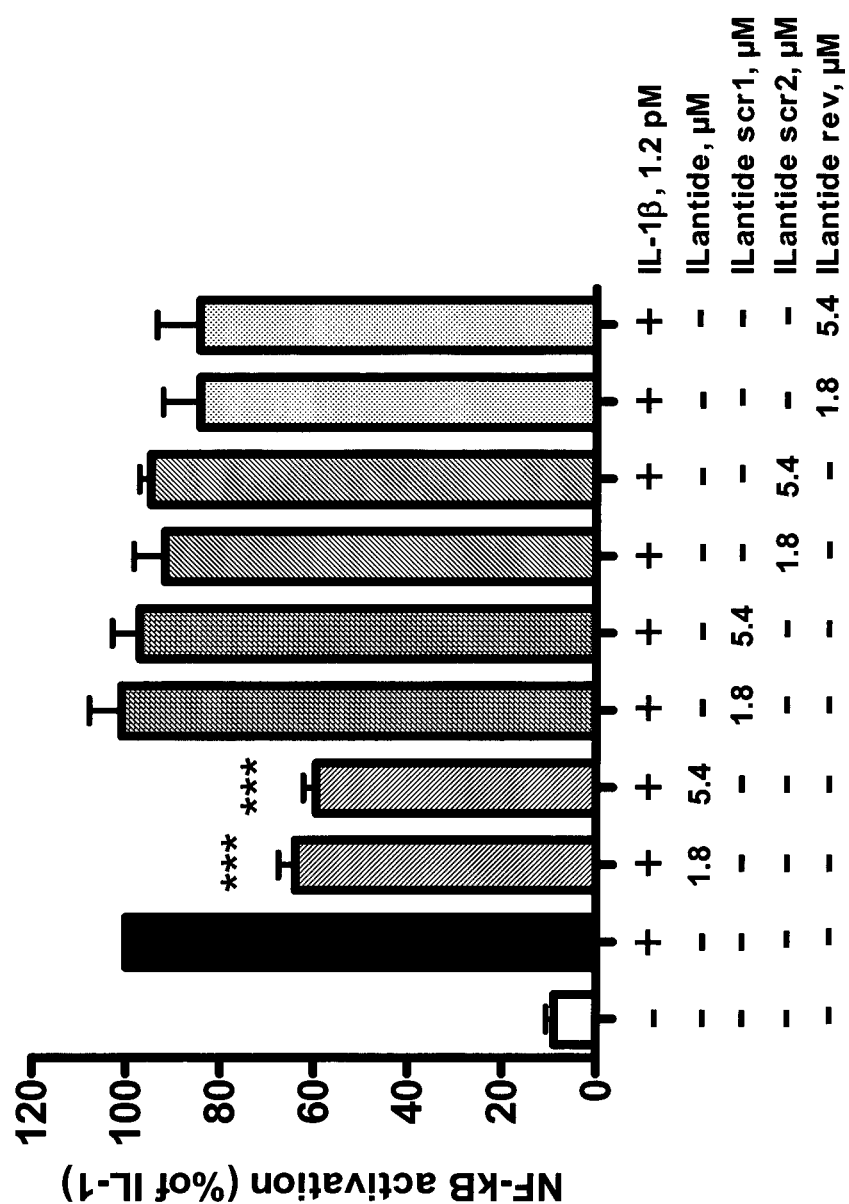
FIG. 8 shows that the effect of the Ilantafin-d peptide (tetrameric dendrimer of SEQ ID NO:1) is sequence-specific, since neither two peptides with scrambled sequences, Ilantafin scr-d1 (KQSAGKRSMS) (SEQ ID NO:39), Ilantafin scr-d2 (KASQKGMSRS) (SEQ ID NO:40), nor a peptide with the reverseequence, Ilantafin rev-d (AQMKSSKRGS) (SEQ ID NO:41) inhibit the activation of NF-KB induced by IL1β.
Figure 9:
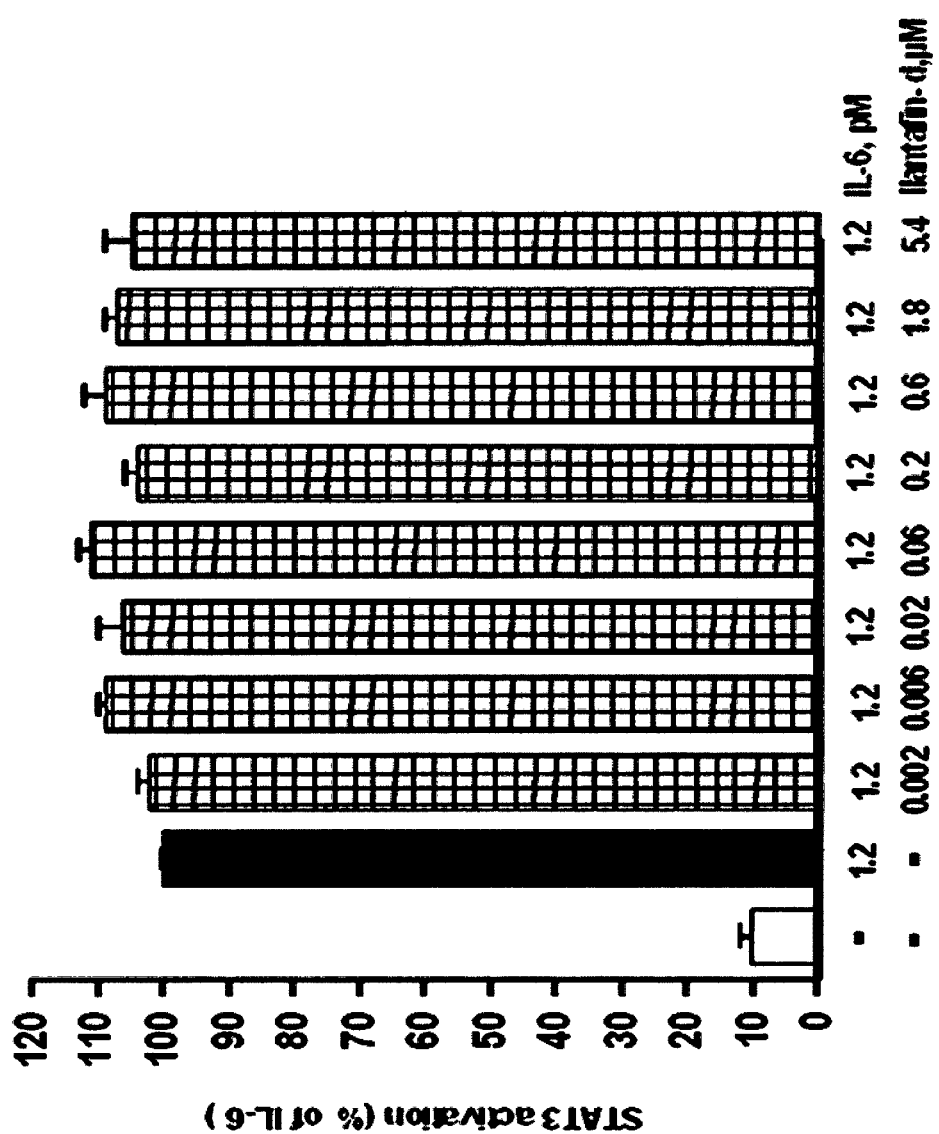
FIG. 9 shows that the effect of the Ilantafin-d peptide (tetrameric dendrimer of SEQ ID NO:1) is target (IL1RI)-specific, since the peptide does not affect the activation of STAT signalling induced by IL6.

The Ilantafin peptide SEQ ID NO:1 (made as a dendrimer/tetramer and in a monomeric form) inhibits activation of macrophages, which is induced by treatment with IL1β (FIG. 5, FIG. 6 and FIG. 7). The Ilantafin effect is sequence-specific, since various forms of a scrambled sequence of Ilantafin, and Ilantafin with the reverse sequence, do not inhibit activation of NF-κB by IL1β (FIG. 8). The Ilantafin effect is sequence-specific, since the peptide does not inhibit signaling induced by IL6 (FIG. 9).
Method:
IL1RI signaling assay: Commercially available Blue™ Cytokine Reporter Cell technology from InvivoGen (Denmark distributor: Sigma-Aldrich Denmark) was used. It is represented by an expanding family of engineered cell lines designed to provide a simple, rapid, and reliable method of monitoring the activation of signaling pathways induced by key cytokines. HEK-Blue™ IL1β cells are specifically engineered to selectively respond to IL1β, and they feature the secreted embryonic alkaline phosphatase (SEAP) reporter gene under the control of an NF-κB-inducible promoter. The inhibitory effect of the Ilantafin peptide in various concentrations on IL1β-induced (1.2 µM) activation of NF-κB was determined and compared with data obtained with commercial IL1Ra and IL1RI. A target/receptor-specificity of the Ilantafin effect was verified employing HEK-Blue™ IL6 cells.

Example 4

Figure 10:
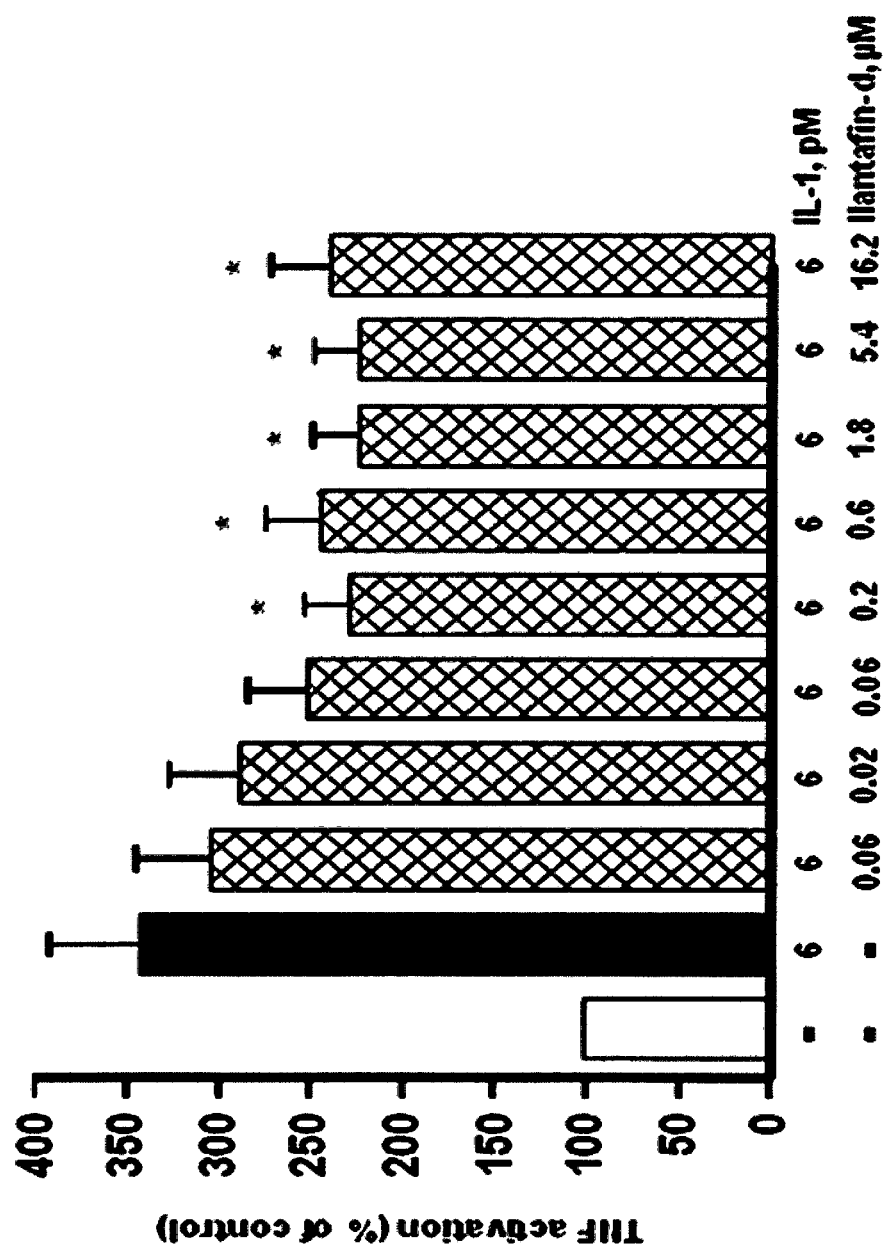
FIG. 10 shows the inhibitory effect of Ilantafin (SEQ ID NO:1) on TNFα secretion by IL1β-activated AMJ2-C8 macrophage cells. The Ilantafin peptide was synthesized as tetrameric dendrimer (Ilantafin-d) attached to a lysine backbone. *p<0.05, when compared to the black bar.
Figure 11:
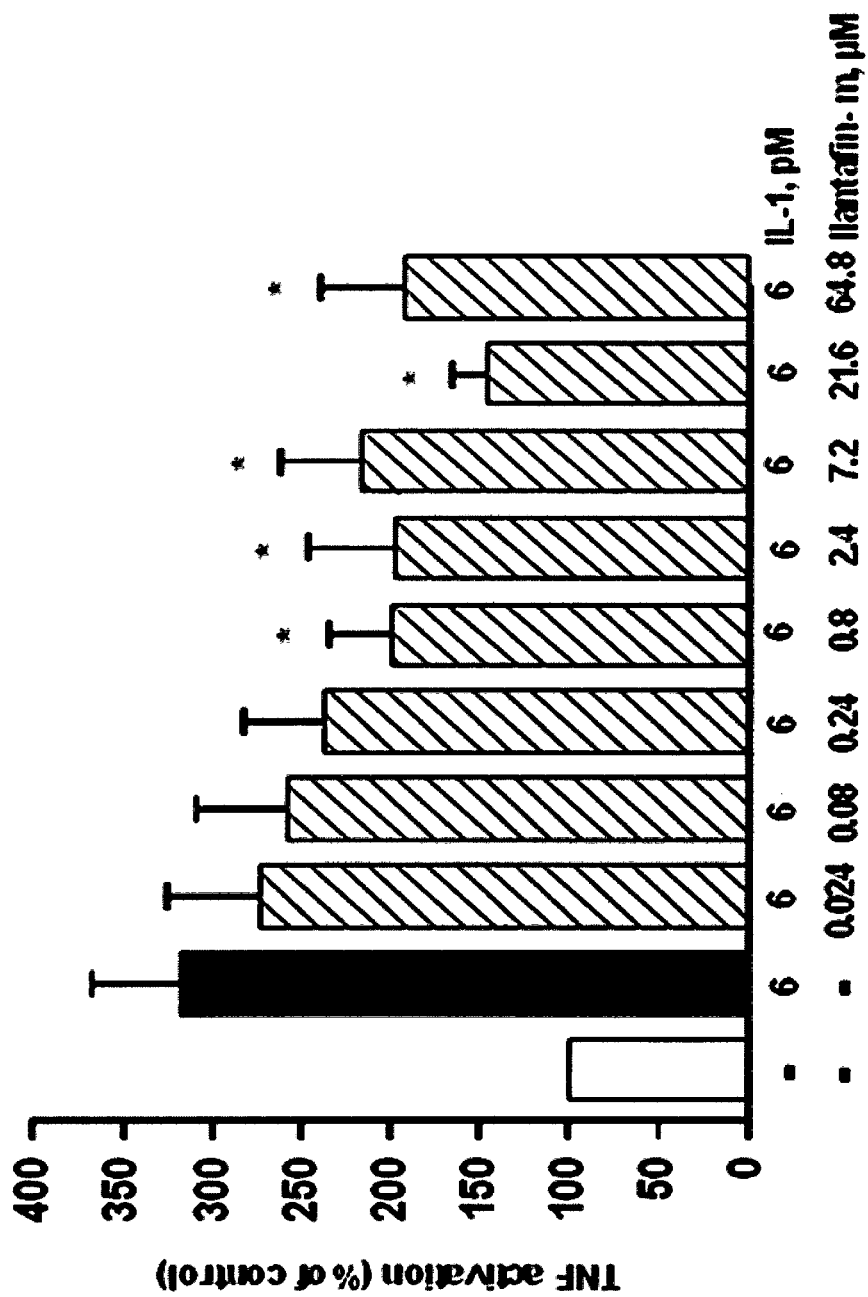
FIG. 11 shows the inhibitory effect of Ilantafin (SEQ ID NO:1) on TNFα secretion by IL1β-activated AMJ2-C8 macrophage cells. The Ilantafin peptide was synthesized as a monomer (Ilantafin-m). *p<0.05, when compared to the black bar.
Figure 12A:
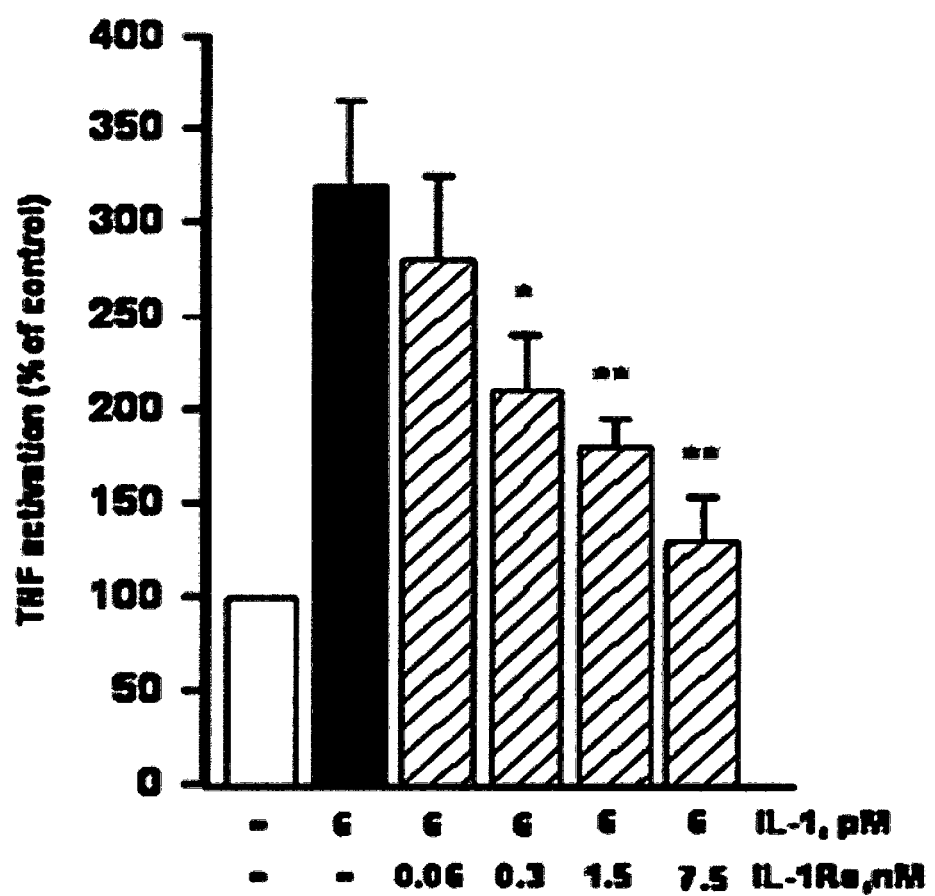
FIGS. 12A-12B show the inhibitory effect of ILRa (FIG. 12A) and SIL1R1 (FIG. 12B) on TNFα secretion by IL1β-activated AMJ2-C8 macrophage cells. *p<0.05, **p<0.01, when compared to the black bar.
Figure 12B:
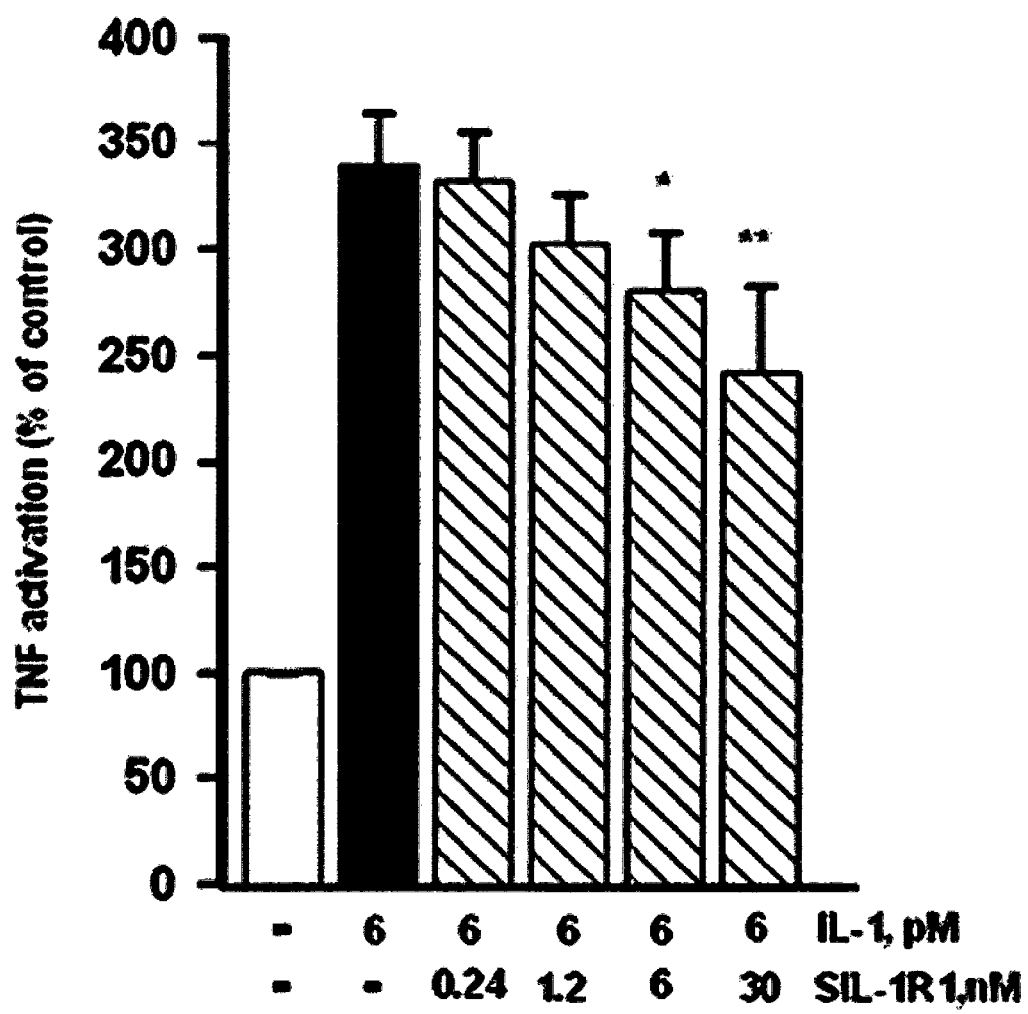
Figure 13A:
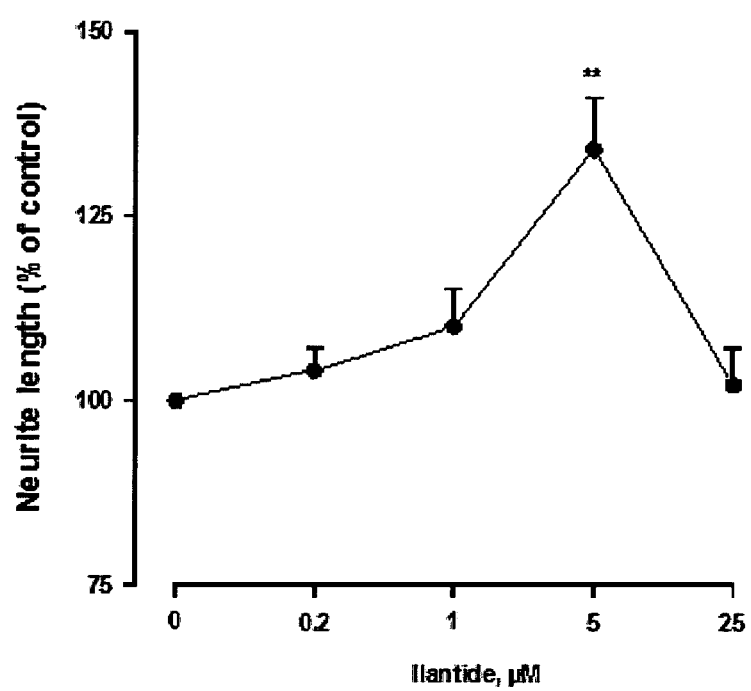
FIGS. 13A-13D show the effect of Ilantafin (SEQ ID NO:1, FIG. 13A), IL1Ra (FIG. 13B), SIL-1R1 (FIG. 13C) and IL1β (FIG. 13D) on neurite outgrowth in primary cultures of cerebellar granule neurons. *p<0.05, **p<0.01, when compared to untreated controls.
Figure 13B:
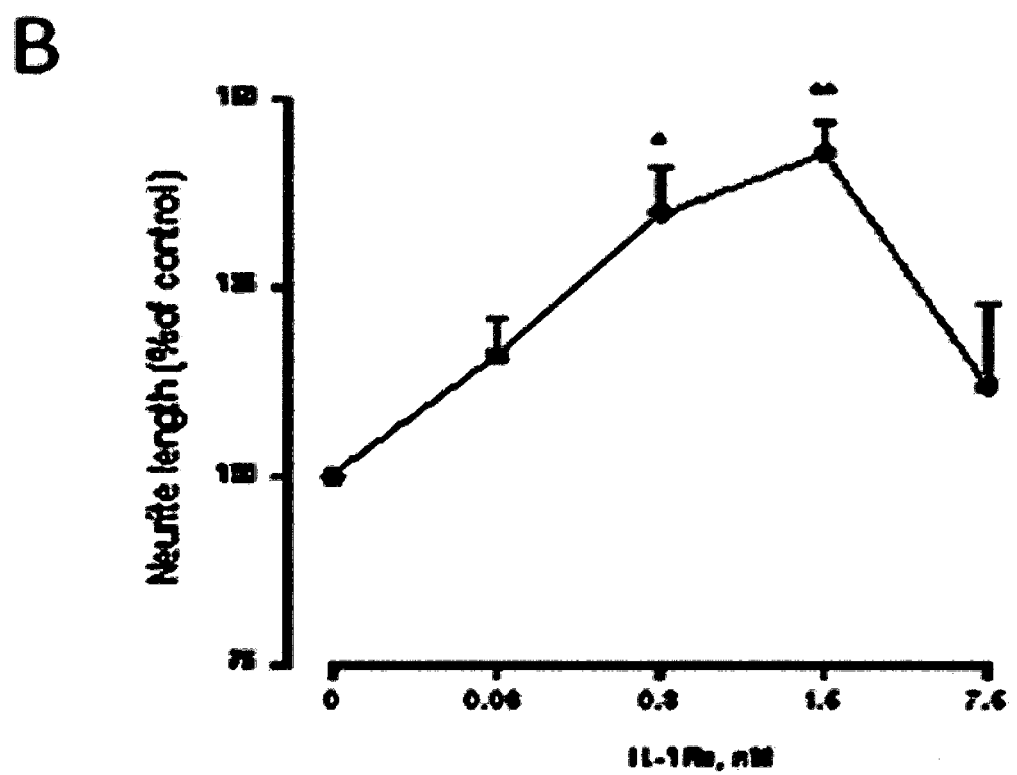
Figure 13C:
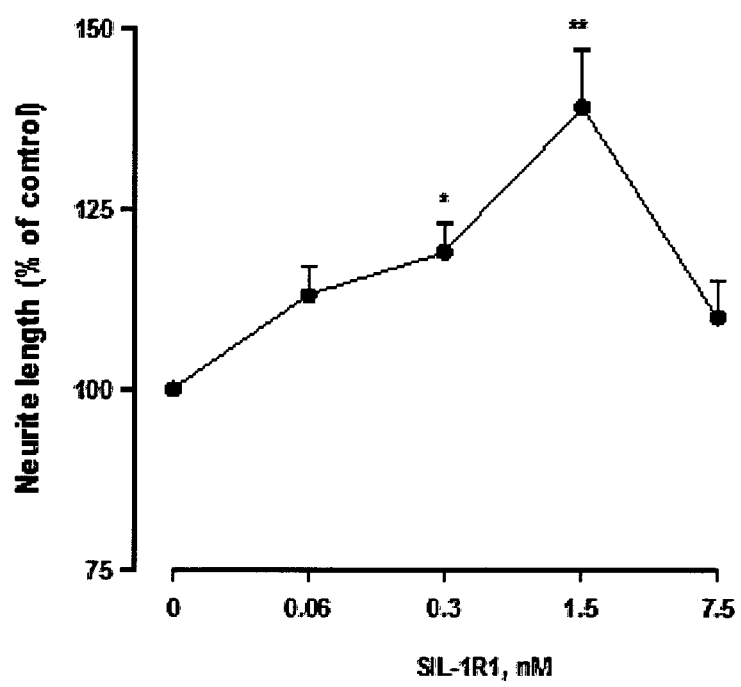
Figure 13D:
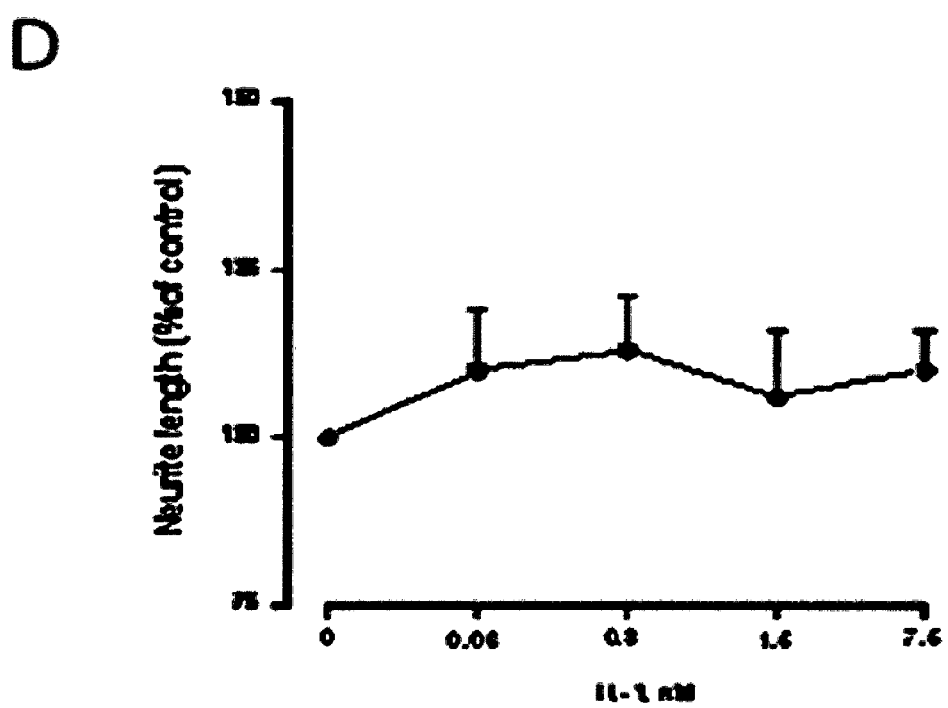

The Ilantafin peptide (SEQ ID NO:1), both as a dendrimer/tetramer or a monomer, in a dose dependent manner inhibits the IL1β-induced activation of macrophages as reflected by TNF-α secretion (FIG. 10, FIG. 11). The IL1Ra and SIL1RI proteins also inhibit macrophage activation (positive controls, FIG. 12).
Method:
The Ilantafin peptide or IL1Ra or IL1RI was added to cultures of macrophages (AMJ2-C8) seeded in 6-well multidishes (Nunc) ($2.5 \times 10^5$ cells/well). After 24 h of incubation at 37° C., IL1β (1.2 µM) was added to the cultures to activate the macrophages. L929 cells were seeded in a 96-well plate at a density of $2 \times 10^5$ cells/mL. Both cell cultures were incubated for 24 h at 37° C. Conditioned medium from the macrophage cultures was collected and added to the fibroblast cultures together with 0.6 µg/well actinomycin. D (Sigma-Aldrich). Finally, after 24 h of incubation at 37° C., 20 µl of 3-(4,5-dimethylthiazol-2-yl)-5-(3-carboxymethoxyphenyl)-2-(4-sulfophenyl)-2H-tetrazolium (MTS) (Promega, Madison, Wis., USA) was added to each well and the plates were incubated protected from light, at 37° C., for ~45 min and the optical density was measured at 490 nm in a Sunrise absorbance reader (Tecan, Männedorf, Switzerland). In order to calculate the amount of TNF-α in the conditioned medium, a standard curve was obtained by treating fibroblasts with different concentrations of TNF-α (R&D systems, Minneapolis, Minn., USA).

Example 5

Figure 14A:
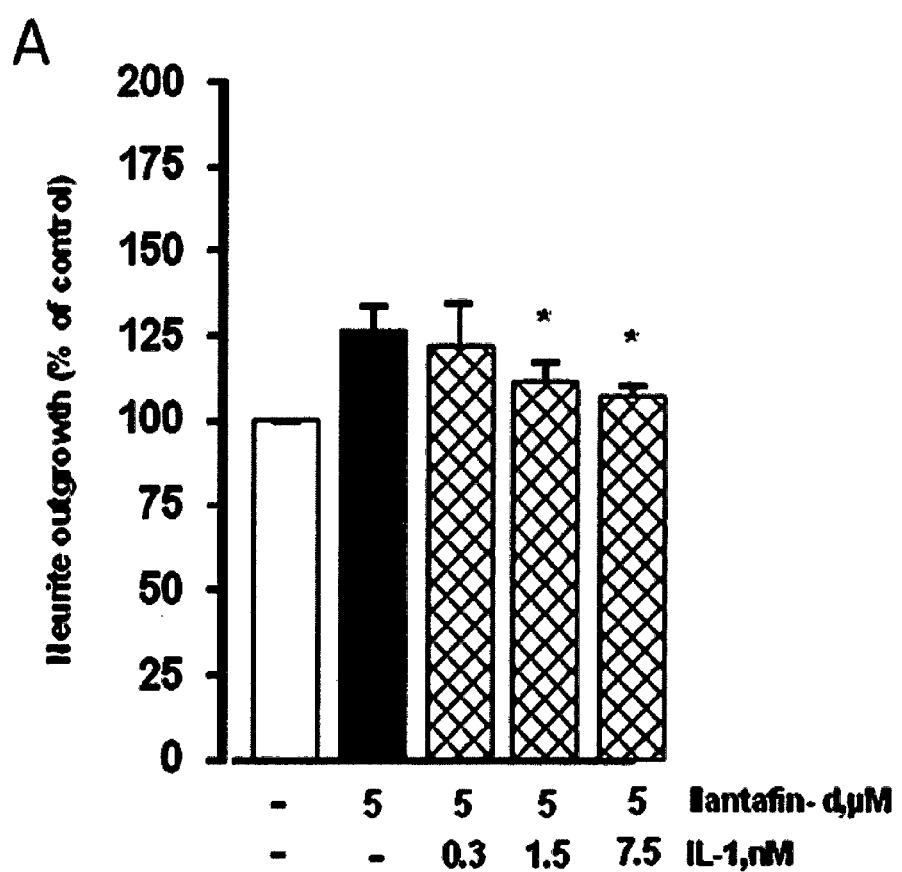
FIGS. 14A-14B show that IL1β competes with Ilantafin (SEQ ID NO:1) and IL1Ra thereby inhibiting Ilantafin (FIG. 14A)- and IL1Ra (FIG. 14B)-induced neurite outgrowth. *p<0.05, when compared to the black bar.
Figure 14B:
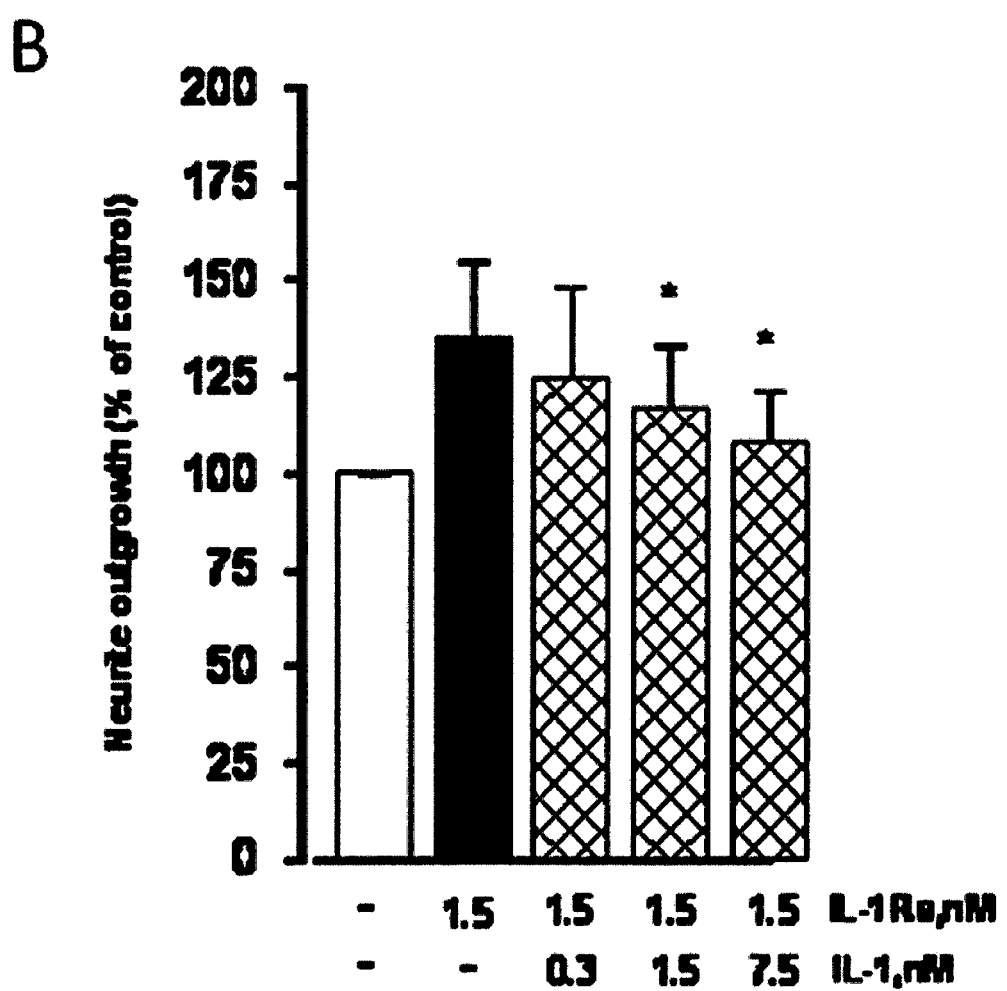

The Ilantafin peptide (SEQ ID NO:1), the IL1Ra and SIL1RI proteins induce neurite outgrowth in primary cerebellar neurons in a dose-dependent manner, whereas IL1β itself does not affect neuritogenesis. Moreover, IL1β inhibits Ilantafin- and IL1Ra induced neurite outgrowth. It indicates that the inhibition of IL1RI activation promotes neuronal differentiation (FIG. 13 and FIG. 19 (same data recalculated), FIG. 14).
Method:
Cerebellar granular neurons (CGN) were prepared from 3 or 7 postnatal (P) day Wistar rats (Charles River, Sulzfeld, Germany or Taconic, Ejby, Denmark). Cerebella were cleared of meninges and blood vessels, roughly homogenized by chopping, and trypsinized with trypsin from Sigma-Aldrich (Brøndby, Denmark). The neurons were washed in the presence of DNAse 1 and soybean trypsin inhibitor (Sigma-Aldrich), and cellular debris was pelleted by centrifugation before plating. CGNs were plated at a density of 10,000 cells/well onto uncoated eight-well Lab-Tek chamber slides (NUNC, Slangerup, Denmark) in Neurobasal-A medium supplemented with 0.4% (w/v) BSA. Peptides or proteins at various concentrations were added to the medium immediately after plating, and cells were maintained at 37° C. and 5% $CO_2$ for 24 h. Cultures then were fixed, blocked and incubated with polyclonal rabbit antibody against rat GAP-43 (Chemicon, Temecula, Calif., USA) followed by incubation with secondary Alexa Fluor488 goat anti-rabbit antibody (Molecular Probes, Eugene, Oreg., USA) as previously described (Neiiendam et al., 2004). The immunostained cultures were all recorded by computer-assisted fluorescence microscopy using a Nikon Diaphot inverted microscope (Nikon, Japan) equipped with a Nikon Plane 20× objective. Images were captured with a charge-coupled device video camera (Grundig Electronics, Nurnberg, Germany) using the software package Prima developed at the Protein Laboratory (University of Copenhagen, Copenhagen, Denmark). The length of neuronal processes per cell was estimated using the software package Process Length developed at the Protein Laboratory (Ronn et al. 2000). For estimation of neurite outgrowth, at least 200±20 cells were processed for each group in each individual experiment.

Example 6

Figure 15A:
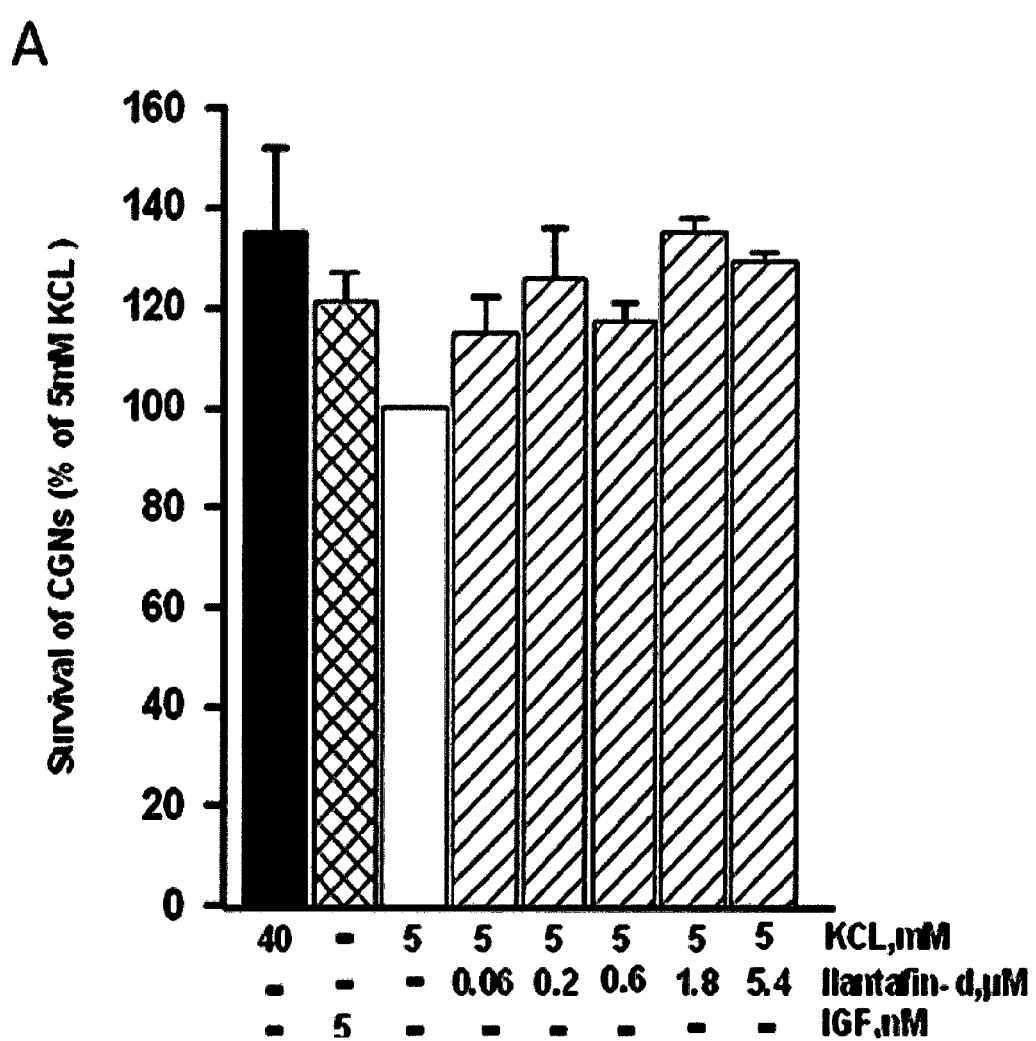
FIG. 15A-15B show that Ilantafin (SEQ ID NO:1), both as a dendrimer (Ilantafin-d, FIG. 15A) and a monomer (Ilantafin-m, FIG. 15B), promotes survival of cerebellar granule neurons induced to undergo apoptosis by lowering potassium concentration. IGF—insulin-like growth factor-1. Results from the two independent experiments are shown.
Figure 15B:
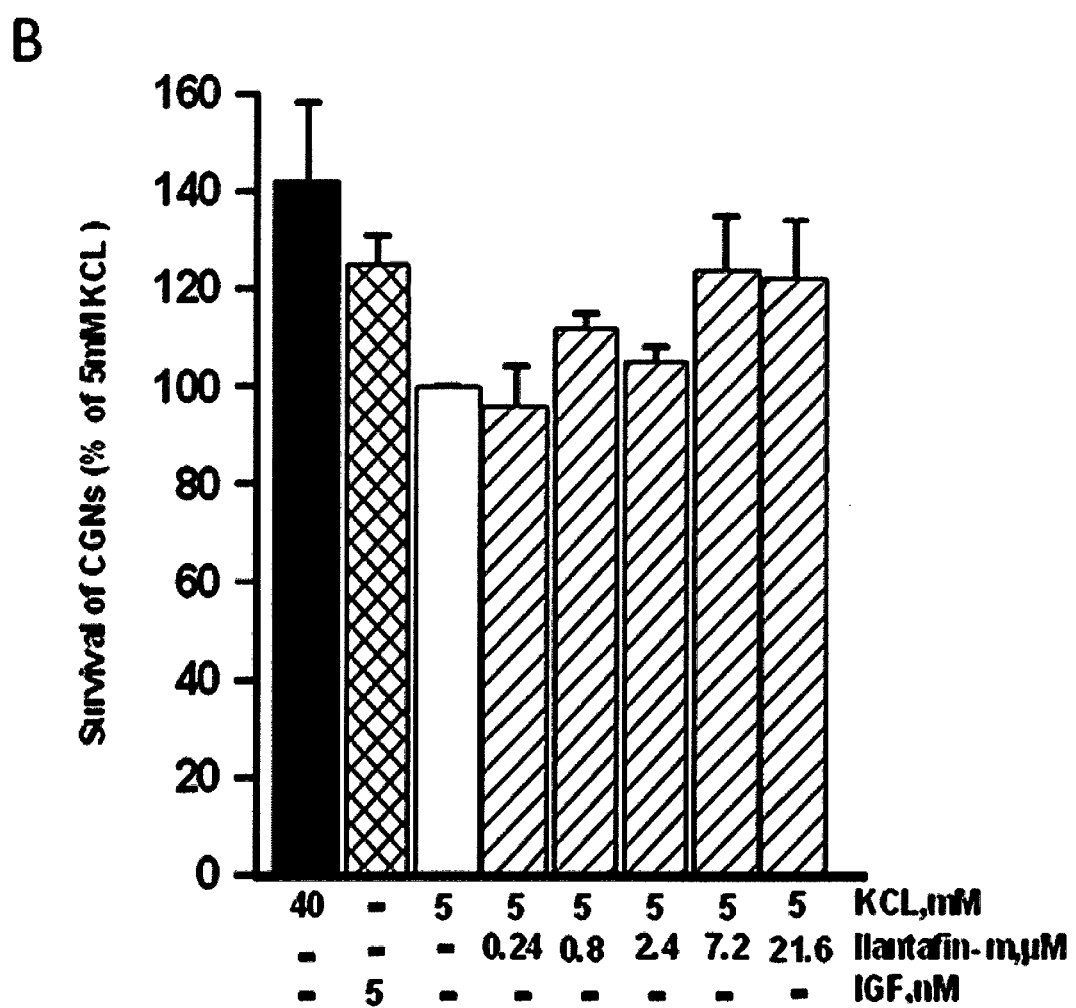
Figure 20A:
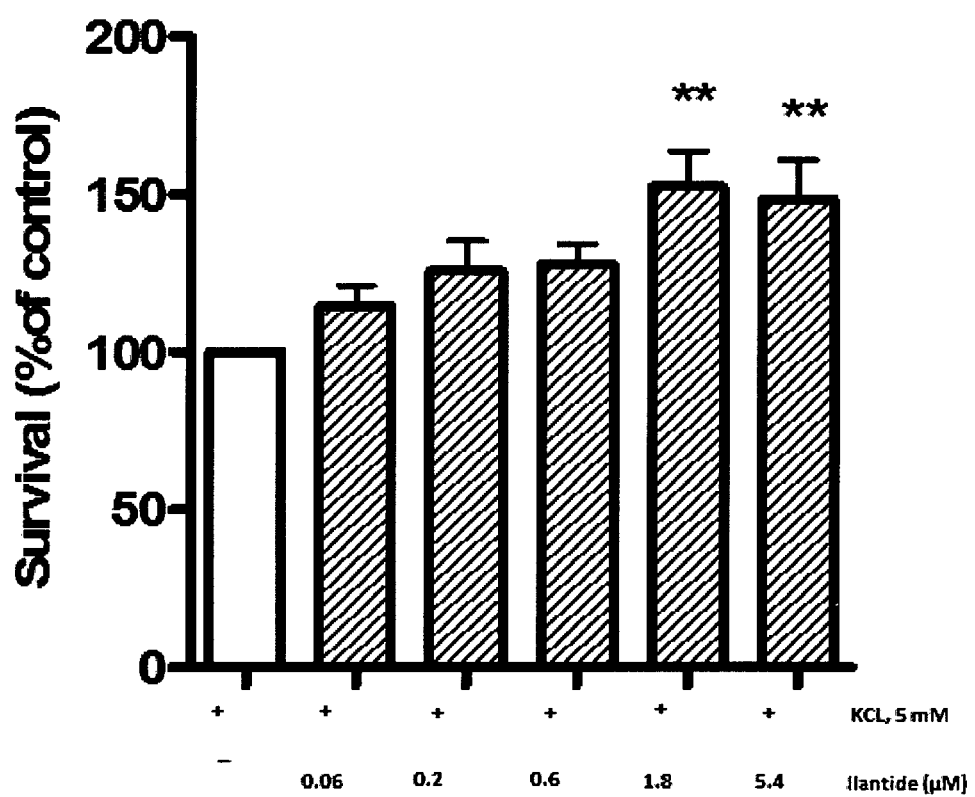
FIGS. 20A-20B show results similar to those presented in FIGS. 15A-15B.
Figure 20B:
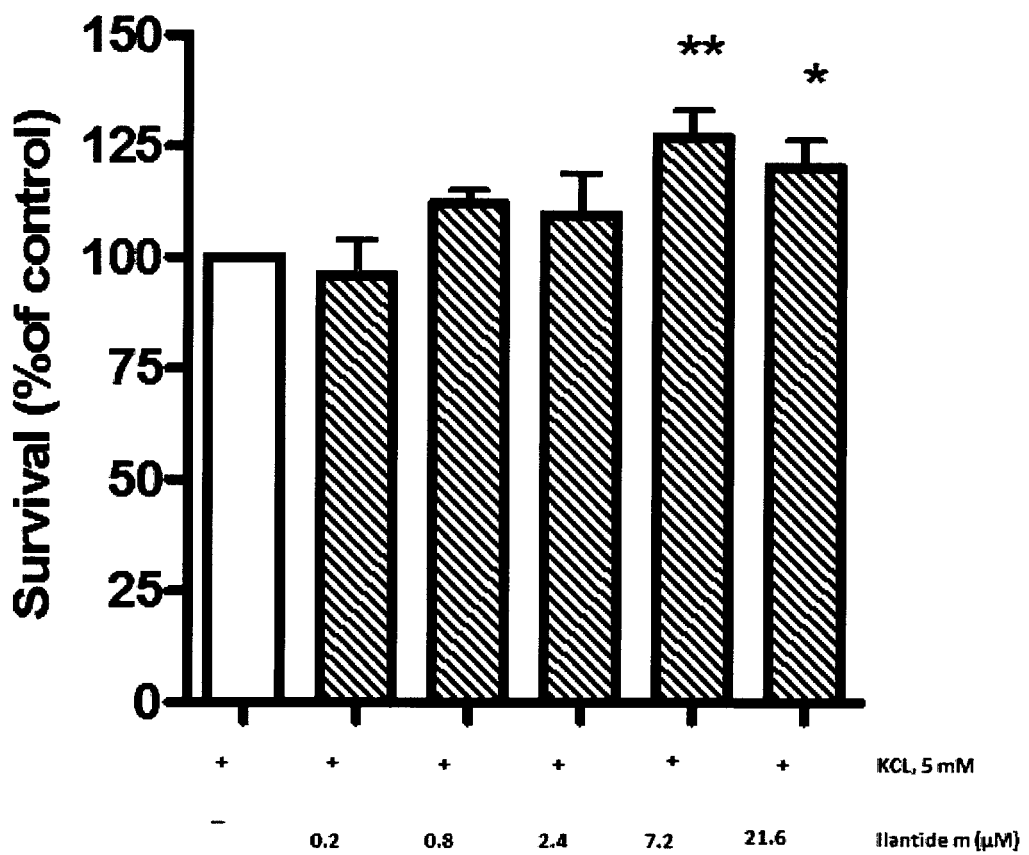

The Ilantafin peptide (SEQ ID NO:1) reduces neuronal cell death (apoptosis), which is induced by lowering concentrations of potassium chloride. The peptide effect is comparable with the effect of the neuronal survival factor IGF-1 (FIG. 15 and FIG. 20).
Method:
Survival assay: Primary cultures of CGN were plated at a density of 100,000 cells/cm2 on poly-L-lysine coated 8-well permanox slides in Neurobasal-A medium (Gibco BRL) supplemented with 2% (v/v) B27, 0.5% (v/v) glutamax, 100 units/mL penicillin, 100 lg/mL streptomycin and KCl, making the final concentration of KCl in the medium 40 mM. 24 hours after plating, cytosine-b-D-arabinofuranoside (Ara-C; Sigma-Aldrich) was added to a final concentration of 10 µM to avoid proliferation of glial cells, after which the neurons were allowed to differentiate for a further 6 days at 37° C. Apoptotic cell death was induced by washing twice and changing the medium to Basal Medium Eagle (BME; Gibco BRL) supplemented with 1% (v/v) glutamine, 100 U/mL penicillin and 100 lg/mL streptomycin, 3.5 g D-glucose/L and 1% (v/v) sodium pyruvate (Gibco BRL) together with various concentrations of peptide. Thereby the concentration of potassium in the cultures was reduced to 5 mM KCl (Ditlevsen et al., 2003). Two days after induction of apoptosis, the cells were fixed with 4% (v/v) formaldehyde and stained with Hoechst 33258 as described for the survival assay employing hippocampal neurons.

Example 7

Figure 16:
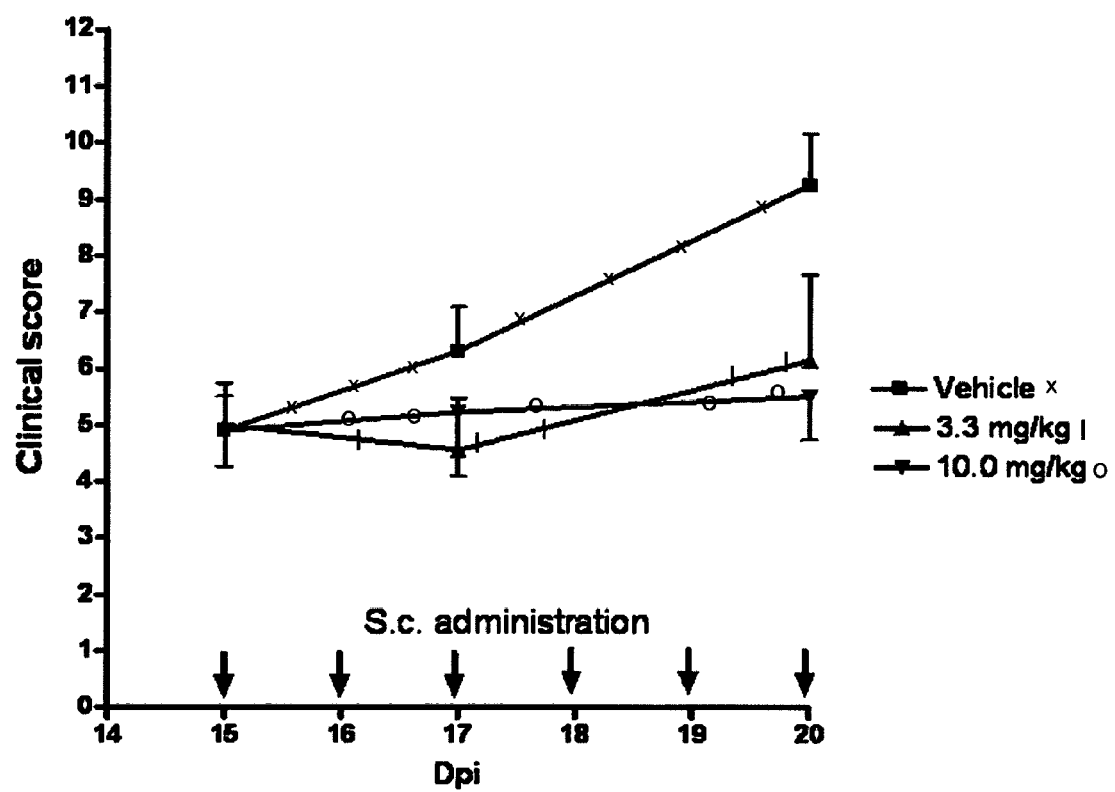
FIG. 16 shows the results of an in vivo study employing the collagen-induced rheumatoid arthritis model in rats. Treatment with Ilantafin-d (tetrameric dendrimer of SEQ ID NO:1) abrogated an increase in clinical manifestations of the disease, when compared with the untreated control group.

The Ilantafin peptide (SEQ ID NO:1) abrogates an increase in clinical manifestations of CIA in rats (FIG. 16).
Method:
Rheumatoid arthritis is a chronic, inflammatory, systemic autoimmune disease that affects about 1% of the general population in Western countries. Collagen-induced arthritis (CIA) in rats is a widely employed animal model for the screening of anti-inflammatory compounds. Collagen bovine, type II (CII, Cat.no.20021, Lot 090209, Chondrex, USA), Complete Freund's Adjuvant, containing 0.1% of *Mycobacterium tuberculosis* (CFA, Cat.no. F5581, Lot 049K8700, Sigma-Aldrich), Incomplete Freund's Adjuvant (IFA, Cat.no. F5506, Lot 058K8702, Sigma). PBS (Panum Institute, Copenhagen University). Isofluran (Baxter). Animals were immunized twice: on day 0 (CII+CFA) and on day 10 (CII+IFA, booster). On day 15 the mean clinical score reached a value of 5.0 and all animals were divided into 3 groups so that the severity of disease (mean clinical score) in all groups was almost equal. The peptide (two doses, 3.3 and 10 mg/kg) was administered subcutaneously daily starting at day 15. The clinical evaluation of the arthritis severity was assessed using the following grading system: 0—no redness or swelling in foot and palm; 1—slight swelling or redness in metatarsophalangeal joint and ankle joint foot or palm; 2—progressed swelling/inflammation and redness from ankle to mid foot or in entire palm; 3—swelling/inflammation of entire foot except toes; 4—swelling and inflammation of entire foot including toes.

Example 8

Detection of Ilantafin peptides (such as SEQ ID NO:1) in plasma and cerebrospinal fluid.

Blood samples are collected from the orbital plexus of anaesthetized 200 g Wistar rats at 15 min, 30 min, 1, 2, 4, 8 and 24 h after single subcutaneous Ilantafin (SEQ ID NO:1) administration (10 mg/kg) as described in Secher et al. (2006). Cerebrospinal fluid is sampled from the cisterna magna at 2 h, as previously described (Secher et al., 2006). Ilantafin concentrations in plasma samples were measured using a competitive enzyme-linked immunosorbent assay. Ninety-six-well Amino™ plates (Nunc) are coated with 30 mg/ml biotinylated albumin (Sigma-Aldrich) diluted in 100 mM carbonate buffer (pH 9.6). Plates are incubated for 2 h and washed three times with 0.05% v/v Tween 20 in phosphate buffered saline (PBST). One sample volume is mixed with three volumes of peroxidase-labelled streptavidin diluted 1:5000 in PBST and incubated for 30 min. A quantity of 100 ml/well of the mixture is then added to biotinylated albumin-coated plates. Plates are incubated for 1 h, washed three times with PBST and developed with TMB plus (Kem-En-Tec, Taastrup, Denmark). The enzymatic reaction is stopped with 0.2M sulphuric acid. Optical density is recorded at 450 nm using a Sunrise absorbance reader (Tecan, Männedorf, Switzerland). All samples are preferably run in duplicate.

To investigate whether SEQ ID NO:1 penetrates the blood-brain barrier in rats, biotin-Ilantafin is detected in plasma and the CSF after subcutaneous administration. If the peptide is present in both the plasma and the CSF, it suggests that systemically administered Ilantafin crosses the blood-brain barrier.

Example 9

The effect of the Ilantafins, such as SEQ ID NO:1 in reversing neuronal cytotoxicity may be evaluated by the following method: "Kainic acid-induced cytotoxicity"

Hippocampal neurons are plated at a density of $5\times10^4$ cells per well in poly-L-lysine-coated eight-well LabTek Permanox slides (Nunc) as previously described (Soroka et al., 2002). After 7 days in culture, neurons are treated with Ilantafin (0.001-3 mM) or full-length IL1RA for 1 h followed by the addition of 300 mM freshly reconstituted kainic acid (Sigma, Brøndby, Denmark). Cells are further cultured for 24 h. The cells are fixed in 4% v/v formaldehyde and stained with 5 mg/ml Hoechst 33258 (Invitrogen, Copenhagen, Denmark) or 5 mg/ml propidium iodide (Sigma). At least 1000 cells/condition are recorded in a systematic series of view fields, with the position of the first field chosen randomly as described in Ronn et al. (2000). Cell viability is estimated based on nuclear morphology (dead cells displaying condensed chromatin or fragmented nuclei) in a semi-automatic mode using software developed at the laboratory to minimize bias. Results are presented as the mean of the live cell ratio [n live cells/(n live cells+n dead cells)+/−SEM].

Example 10

The effect of the Ilantafins, such as SEQ ID NO:1 in attenuating seizures, decrease mortality and decreasing neurodegeneration may be evaluated by the following method: "Kainic acid-induced seizures".

Male C57BL/6J mice, 28-32 g, are injected subcutaneously with Ilantafin (10 mg/kg), full-length IL1RA or vehicle 48, 24 and 2 h prior to kainic acid treatment. Based on preliminary dose-adjustment experiments, two doses of kainic acid (intraperitoneal) are chosen to perform two sets of experiments to induce either low-grade seizures (20 mg/kg kainic acid) or high-grade seizures and mortality (30 mg/kg kainic acid). Measured parameters included latency of seizure onset, seizure severity and mortality. Seizure activity is recorded for 2 h following kainic acid administration by an observer blind to treatment and assessed according to a modified Racine scale (0=immobility; 1=facial automatism; 2=head nodding; 3=forelimb clonus; 4=rearing; 5=generalized convulsions; 6=death; Racine, 1972). Seizure grades 1-3 are regarded as low-grade seizures, and seizure grades 4-5 were regarded as high-grade seizures. The latency of immobility is measured as the time between kainic acid injection and the appearance of immobility. The control group of animals received a vehicle injection.

Example 11

Peptides were synthesized using the Fmoc protection strategy on TentaGel resin (Rapp Polymere, Tubingen, Germany) using Fmoc-(Calbiochem-Novabiochem) protected amino acids. Dendrimers were composed of four monomers coupled to a lysine backbone. Dimers were composed of two monomers coupled to a lysine residue. Peptides were at least 95% pure as estimated by high performance liquid chromatography and matrix-assisted laser desorption/ionization time-of-flight mass spectroscopy (VG TOF Spec E, Fisons Instruments, Beverly, Mass.).

Example 12

Peptide Solubility

Upon receiving the peptides from the synthesizing company (as powder), they were reconstituted in water, in PBS or in medium. Thus it is immediately apparent whether a peptide is soluble or not.

Example 13

Peptide Stability

A method for evaluating peptide stability is that the peptide amount in solution is measured spectrophotometrically or by MS (mass spectrometry; measures the mass-to-charge ratio of charged particles) as a function of time (1, 2, 3 etc days) when keeping the peptide in solution at 4° C. and at room temperature.

Example 14

Effect of Ilantafin SEQ ID NO:1 (SGRKSSKMQA) in a rat model of collagen-induced arthritis (CIA).
Method:
Collagen-induced arthritis in rats (CIA).
Induction of CIA. The CIA study was performed on a total of 40 male Wistar rats with an average weight of 150 g at the beginning of the experiment. CIA was induced by subcutaneous (s.c.) injection of bovine collagen type II (CII, Sigma-Aldrich) solubilised in 0.05 M acetic acid (2 mg/ml), and then emulsified 1:1 with CFA (Sigma-Aldrich) containing 1.0 mg/ml heat-inactivated *M. tuberculosis*. Under inhalation anaesthesia (Isofluran, 3%) 250 µl of the emulsion containing 250 µg of CII and 125 µg of *M. tuberculosis* was injected (s.c.) at the tail base (post-immunization day, dpi 0).

Treatment design. At dpi 8, before onset of clinical signs, all animals were randomly divided into two groups, 20 rats per group, and were dosed daily during 8 days (dpi 8-15) with Ilantafin (10.0 mg/kg, s.c.) or vehicle (PBS, 1.0 ml/kg, s.c.). Clinical evaluation was carried out on dpi 7-16, and was continued in the period without treatment on dpi 29-33.

Clinical scores. An observer blinded to treatment groups evaluated the severity of arthritis employing the following grading system: 0— no redness or swelling in foot; 1—slight redness in foot or redness and swelling in single interfalangeal joints; 2—moderate swelling and redness in ankle and metatarsal part of foot; 3—marked swelling and redness of entire foot, restricted usage of foot in locomotion; 4—marked swelling and redness of entire foot, impossibility of usage foot in locomotion and rearing. Since CIA typically involves only the hind limbs, the arthritic index of a rat was defined as the sum of the 2 limb scores. Animals were sacrificed when severity of the arthritis reached score 7.

Statistical analysis was performed employing two-way ANOVA and t-test.

Figure 17:
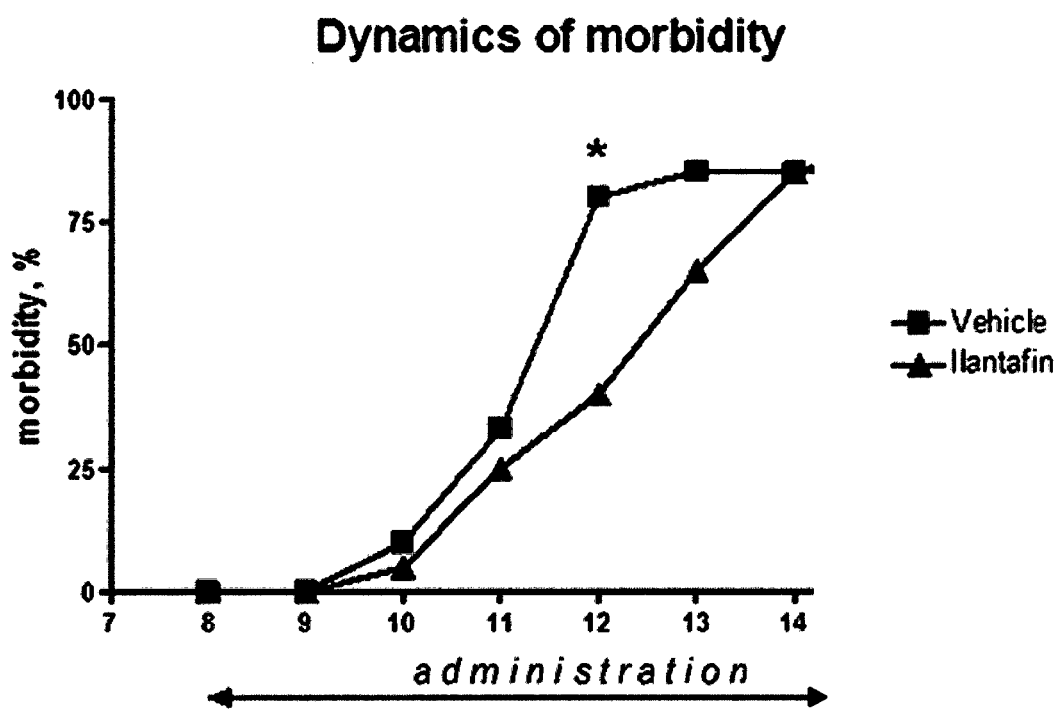
FIG. 17 shows how Ilantafin reduces morbidity of animals with CIA. Morbidity was expressed as a percentage of animals reached clinical index 7 and therefore sacrificed by the test day. Ilantafin significantly reduced morbidity by dpi 12. *-P<0.05 (unpaired t-test with Welch's correction).

Results:

Ilantafin reduces morbidity of animals with CIA, see FIG. 17. Morbidity was expressed as a percentage of animals reached clinical index 7 and therefore sacrificed by the test day. Ilantafin significantly reduced morbidity by dpi 12. *–$P<0.05$ (unpaired t-test with Welch's correction).

Figure 18:
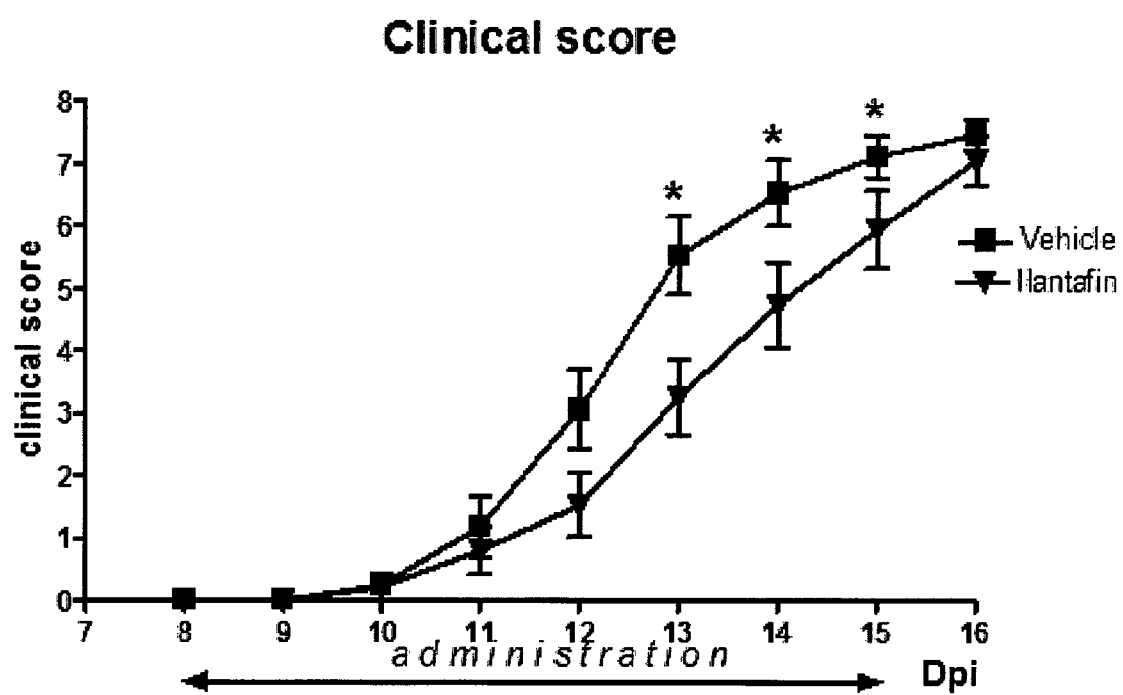
FIG. 18 shows how Ilantafin attenuates severity of CIA (clinical evaluation). Two-way ANOVA revealed significant effect of treatment on clinical score of animals with CIA [F(1, 238)=18.05, P<0.0001]. Ilantafin attenuated severity of CIA on dpi 13-15. *-P<0.05 (unpaired t-test with Welch's correction).
Figure 19A:
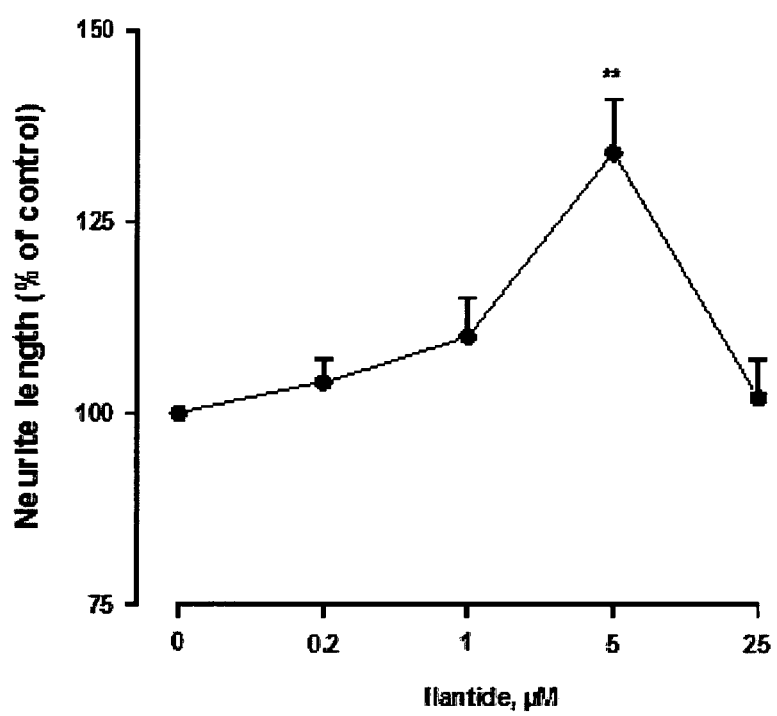
FIGS. 19A-19D show the same results as in FIGS. 13A-13D recalculated.
Figure 19B:
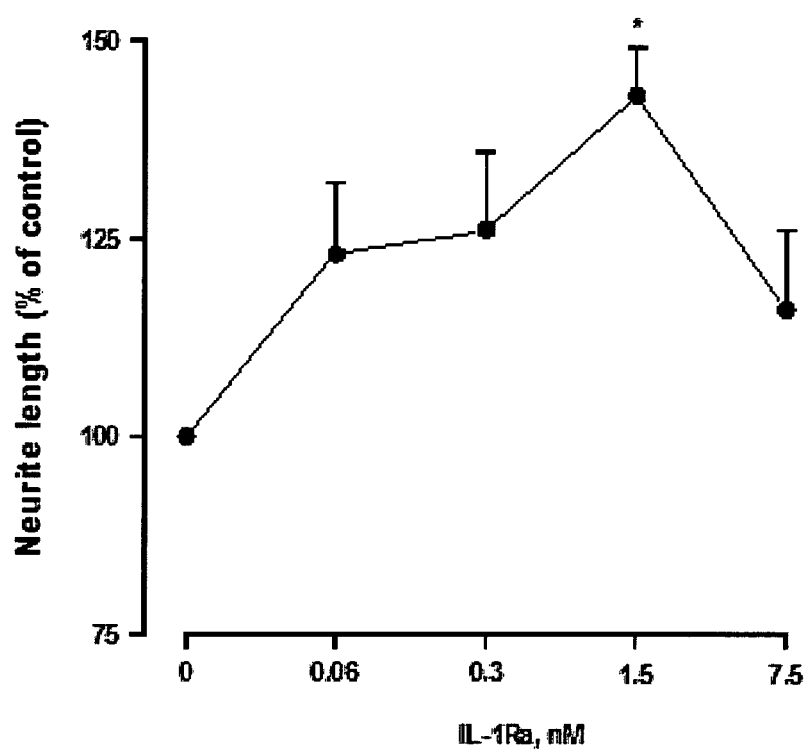
Figure 19C:
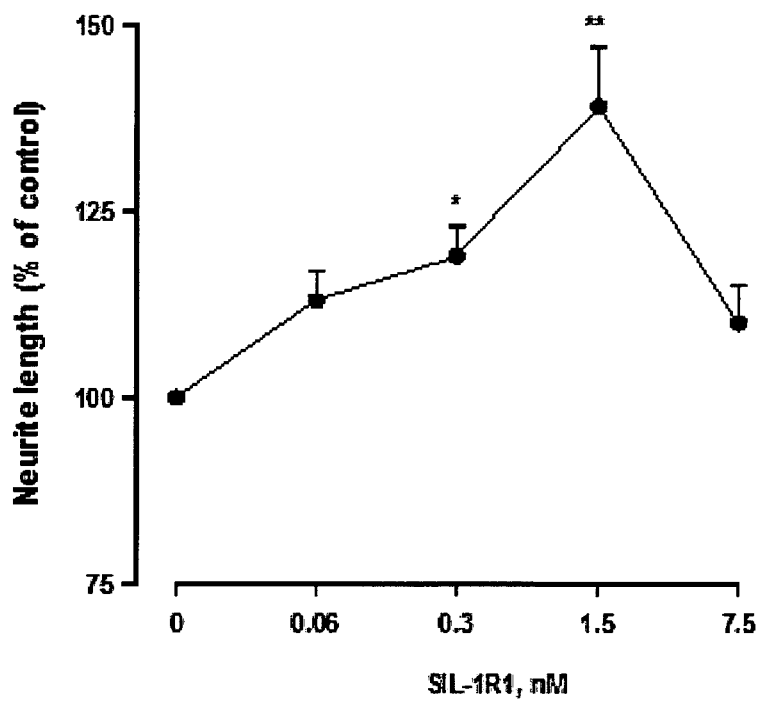
Figure 19D:
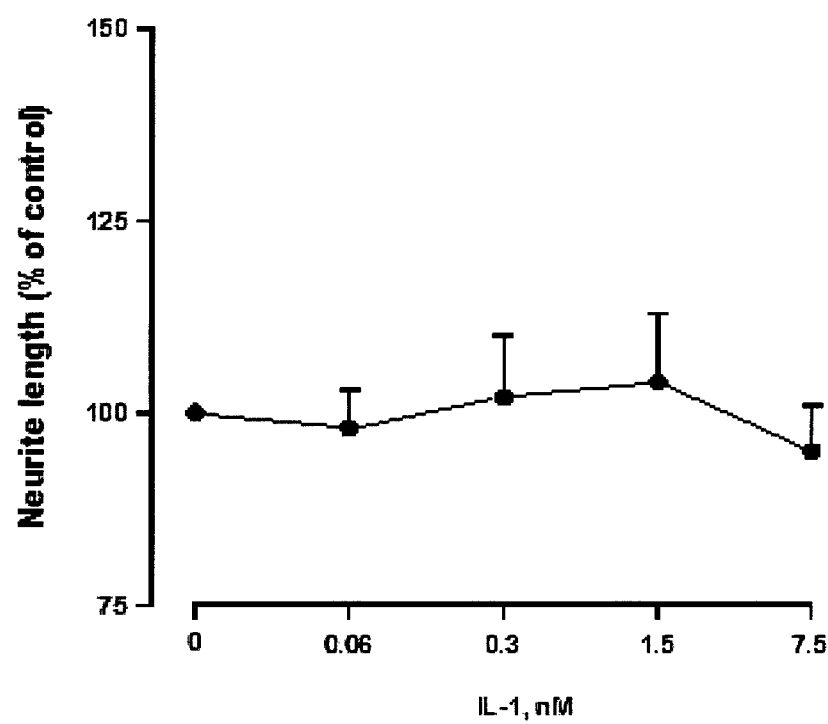

Furthermore, Ilantafin attenuates severity of CIA (clinical evaluation), see FIG. 18. Two-way ANOVA revealed significant effect of treatment on clinical score of animals with CIA [$F(1, 238)=18.05$, $P<0.0001$]. Ilantafin attenuated severity of CIA on dpi 13-15. *–$P<0.05$ (unpaired t-test with Welch's correction).

REFERENCES

Cawthorne C, Prenant C, Smigova A, Julyan P, Maroy R, Herholz K, Rothwell N, Boutin H (2011) Biodistribution, pharmacokinetics and metabolism of interleukin-1 receptor antagonist (IL-1RA) using [$^{18}$F]-IL1RA and PET imaging in rats. *Br J Pharmacol* 162:659-672.

Chang R C, Chiu K, Ho Y S, So K F (2009) Modulation of neuroimmune responses on glia in the central nervous system: implication in therapeutic intervention against neuroinflammation. *Cell Mol Immunol* 6:317-326.

Clark S R. McMahon C J, Gueorguieva I, Rowland M, Scarth S, Georgiou R, Tyrrell P J, Hopkins S J, Rothwell N J (2008) Interleukin-1 receptor antagonist penetrates human brain at experimentally therapeutic concentrations. *J Cereb Blood Flow Metab* 28:387-394.

Dinarello C A (1996) Biologic basis for interleukin-1 in disease. *Blood* 87:2095-2147.

Ditlevsen D K, Køhler L B, Pedersen M V, Rissel M, Kolkova K, Meyer M, Berezin V and Bock E. The role of phosphatidylinositol 3-kinase in neural cell adhesion molecule-mediated neuronal differentiation and survival. *J. Neurochem.* 2003, 84:546-556.

Hallegua D S, Weisman M H (2002) Potential therapeutic uses of interleukin 1 receptor antagonists in human diseases. *Ann Rheum Dis* 61:960-967.

Heneka M T, O'Banion M K, Terwel D, Kummer M P (2010) Neuroinflammatory processes in Alzheimer's disease. *J Neural Transm* 117:919-947.

Koprich J B, Reske-Nielsen C, Mithal P, Isacson O (2008) Neuroinflammation mediated by IL-1β increases susceptibility of dopamine neurons to degenertion in an animal model of Parkinson's disease. *J Neuroinflammation* 5:8.

Krause D L, Müller N (2010) Neuroinflammation, microglia and implications for anti-inflammatory treatment in Alzheimer's disease. Int J Alzheimers Dis pii:732806.

Massoud F, Gauthier S (2010) Update on the pharmacological treatment of Alzheimer's disease. *Curr Neuropharmacol* 8:69-80.

Neiiendam J L, Køhler L B, Christensen C, Li S, Pedersen M V, Ditlevsen D K, Kornum M K, Kiselyov W, Berezin V and Bock E. An NCAM-derived FGF-receptor agonist, the FGF-peptide, induces neurite outgrowth and neuronal survival in primary rat neurons. *J. Neurochem.* 2004, 91:920-935.

Rønn LC, Ralets I, Hartz B, Beck M, Berezin A, Berezin V, Møller A and Bock E. A simple procedure for quantification of neurite outgrowth based on stereological principles. *J. Neurosci. Meth.* 2000, 100:25-32.

Schreuder H, Tardif C, Trump-Kallmeyer S, Soffientini A, Sarubbi E, Akeson A, Bowlin T, Yanofsky S, Barrett R W (1997) A new cytokine-receptor binding mode revealed by the crystal structure of the IL-1 receptor with an antagonist. *Nature* 386:194-200.

Secher T, Novitskaia V, Berezin V, Bock E, Glenthoj B, Klementiev B. A neural cell adhesion molecule-derived fibroblast growth factor receptor agonist, the FGL-peptide, promotes early postnatal sensorimotor development and enhances social memory retention. Neuroscience 2006; 141: 1289-99.

Spulber S, Bartfai T, Schultzberg M (2009) IL-1/IL-1ra balance in the brain revisited: evidence from transgenic mouse models. *Brain Behav Immun* 23:573-579.

Soroka V, Kiryushko D, Novitskaya V, Ronn L C, Poulsen F M, Holm A, et al. Induction of neuronal differentiation by a peptide corresponding to the homophilic binding site of the second Ig module of the neural cell adhesion molecule. J Biol Chem 2002; 277: 24676-83.

Tarkowski E, Liljeroth A M, Nilsson A, Minthon L, Blennow K (2001) Decreased levels of intrathetical interleukin 1 receptor antagonist in Alzheimer's disease. *Dement Geriatr Cogn Disord* 12:314-317.

The invention claimed is:

1. A multimeric compound consisting of,
   i) two or more peptides wherein each of said two or more peptides consists of 10 to 14 consecutive amino acid residues derived from IL-1 receptor antagonist protein (IL1RA), each peptide:
   consisting of the amino acid sequence of SEQ ID NO:1 and optionally additional amino acid residues up to a total length of 11 to 14 amino acid residues; or
   consisting of a variant of SEQ ID NO:1 having at least 90% identity to SEQ ID NO:1, said variant comprising one conservative amino acid substitution, and optionally additional amino acid residues up to a total length of 11 to 14 amino acid residues;
   wherein each peptide is capable of binding to IL-1 receptor type 1 (IL1RI), and capable of interfering with the binding of IL-1 to IL1RI, and
   ii) optionally one or more linker groups.

2. The compound according to claim 1, wherein said multimeric compound is a dendrimer.

3. The compound according to claim 1, wherein said two or more peptides are identical with respect to each other.

4. The compound according to claim 1, wherein said two or more peptides are non-identical with respect to each other.

5. The compound according to claim 1, wherein each of said two or more peptides consists of SEQ ID NO: 1.

6. The compound according to claim 1, wherein said linker groups comprise a lysine backbone.

7. The compound according to claim 1, wherein said linker groups are parts of a polymer carrier.

8. The compound according to claim 2, wherein said dendrimer consists of 4, 8, 16 or 32 of said peptides, and optionally one or more linker groups.

9. The compound according to claim 8, wherein said dendrimer is a tetrameric dendrimer.

10. The compound according to claim 1, wherein said multimeric compound is selected from the group consisting of a dimer, a trimer and a tetramer.

11. A multimeric compound comprising two or more peptides, wherein each of said two or more peptides consists of 10 to 14 consecutive amino acid residues derived from IL-1 receptor antagonist protein (IL1RA), each peptide consisting of:
   the amino acid sequence of SEQ ID NO:1 and optionally additional amino acid residues up to a total length of 11 to 14 amino acid residues; or
   a variant of SEQ ID NO: 1 having at least 90% identity to SEQ ID NO: 1, said variant comprising one conservative amino acid substitution, and optionally additional amino acid residues up to a total length of 11 to 14 amino acid residues;
   wherein each peptide is capable of binding to IL-1 receptor type 1 (IL1RI), and capable of interfering with the binding of IL-1 to IL1RI; and
   wherein the two or more peptides are linked to each other by a linker group e consisting of one lysine residue, or a lysine backbone consisting of a plurality of lysine residues.

12. The compound according to claim 11, wherein each of said two or more peptides consists of SEQ ID NO:1.

13. The compound according to claim 11, wherein said multimeric compound is selected from the group consisting of a dimer, a trimer and a tetramer.

14. The compound according to claim 11, wherein said multimeric compound is selected from the group consisting of a dendrimer and a tetrameric dendrimer.

15. A multimeric compound comprising:
   three or more peptides wherein each of said three or more peptides consists of 10 to 14 consecutive amino acid residues derived from IL-1 receptor antagonist protein (IL1RA), each peptide:
   consisting of the amino acid sequence of SEQ ID NO:1 and optionally additional amino acid residues up to a total length of 11 to 14 amino acid residues; or
   consisting of a variant of SEQ ID NO:1 having at least 90% identity to SEQ ID NO:1, said variant comprising one conservative amino acid substitution, and optionally additional amino acid residues up to a total length of 11 to 14 amino acid residues;
   wherein each peptide is capable of binding to IL-1 receptor type 1 (IL1RI), and capable of interfering with the binding of IL-1 to IL1RI.

16. The compound according to claim 15, wherein each of said three or more peptides consists of SEQ ID NO:1.

17. The compound according to claim 15, wherein said multimeric compound is a tetramer.

18. The compound according to claim 15, wherein said multimeric compound is selected from the group consisting of a dendrimer and a tetrameric dendrimer.

19. The compound according to claim 15, wherein said three or more peptides are linked via a linker group.

20. The compound according to claim 19, wherein said linker group is a lysine backbone consisting of one lysine residue, or a lysine backbone consisting of a plurality of lysine residues.

* * * * *

SEQUENCE LISTING

<160> NUMBER OF SEQ ID NOS: 41

<210> SEQ ID NO 1
<211> LENGTH: 10
<212> TYPE: PRT
<213> ORGANISM: Homo sapiens

<400> SEQUENCE: 1

Ser Gly Arg Lys Ser Ser Lys Met Gln Ala 1               5                   10

<210> SEQ ID NO 2
<211> LENGTH: 10
<212> TYPE: PRT
<213> ORGANISM: Homo sapiens

<400> SEQUENCE: 2

Ser Gly Arg Lys Pro Ser Lys Met Gln Ala
1               5                   10

<210> SEQ ID NO 3
<211> LENGTH: 8
<212> TYPE: PRT
<213> ORGANISM: Homo sapiens

<400> SEQUENCE: 3

Ser Gly Arg Lys Ser Gln Lys Met
1               5

<210> SEQ ID NO 4
<211> LENGTH: 8
<212> TYPE: PRT
<213> ORGANISM: Homo sapiens

<400> SEQUENCE: 4

Arg Lys Ala Ser Lys Leu Gln Ala
1               5

<210> SEQ ID NO 5
<211> LENGTH: 8
<212> TYPE: PRT
<213> ORGANISM: Homo sapiens

<400> SEQUENCE: 5

Ser Ala Arg Lys Ser Glu Lys Met
1               5

<210> SEQ ID NO 6
<211> LENGTH: 8
<212> TYPE: PRT
<213> ORGANISM: Homo sapiens

<400> SEQUENCE: 6

Ser Gly Arg Gln Ser Pro Lys Met
1               5

<210> SEQ ID NO 7
<211> LENGTH: 12
<212> TYPE: PRT
<213> ORGANISM: Homo sapiens

<400> SEQUENCE: 7

Ser Gly Arg Lys Ser Pro His Ser Lys Leu Pro Ala
1               5                   10

<210> SEQ ID NO 8
<211> LENGTH: 8
<212> TYPE: PRT
<213> ORGANISM: Homo sapiens

<400> SEQUENCE: 8

Ser Ser Arg Gln Ser Ser Lys Met
1               5

```
<210> SEQ ID NO 9
<211> LENGTH: 10
<212> TYPE: PRT
<213> ORGANISM: Homo sapiens

<400> SEQUENCE: 9

Ser Gly Lys Arg Pro Cys Lys Met Gln Ala
1               5                   10

<210> SEQ ID NO 10
<211> LENGTH: 7
<212> TYPE: PRT
<213> ORGANISM: Homo sapiens

<400> SEQUENCE: 10

Arg Met Asn Ser Lys Met Gln
1               5

<210> SEQ ID NO 11
<211> LENGTH: 6
<212> TYPE: PRT
<213> ORGANISM: Homo sapiens

<400> SEQUENCE: 11

Lys Ser Pro Lys Met Gln
1               5

<210> SEQ ID NO 12
<211> LENGTH: 7
<212> TYPE: PRT
<213> ORGANISM: Homo sapiens

<400> SEQUENCE: 12

Arg Lys Gly Gly Lys Met Gln
1               5

<210> SEQ ID NO 13
<211> LENGTH: 10
<212> TYPE: PRT
<213> ORGANISM: Homo sapiens

<400> SEQUENCE: 13

Ser Gly Arg Gly Lys Ser Ser Ser Lys Met
1               5                   10

<210> SEQ ID NO 14
<211> LENGTH: 10
<212> TYPE: PRT
<213> ORGANISM: Homo sapiens

<400> SEQUENCE: 14

Gly Arg Arg Ser Ser Arg Lys Met Pro Ala
1               5                   10

<210> SEQ ID NO 15
<211> LENGTH: 8
<212> TYPE: PRT
<213> ORGANISM: Homo sapiens

<400> SEQUENCE: 15

Arg Lys Ala Asn Lys Leu Gln Ala
1               5

<210> SEQ ID NO 16
```

```
<211> LENGTH: 9
<212> TYPE: PRT
<213> ORGANISM: Homo sapiens

<400> SEQUENCE: 16

Ser Gly Arg Lys Ser His Arg Leu Gln
1               5

<210> SEQ ID NO 17
<211> LENGTH: 7
<212> TYPE: PRT
<213> ORGANISM: Homo sapiens

<400> SEQUENCE: 17

Arg Lys Ala Trp Lys Met Gln
1               5

<210> SEQ ID NO 18
<211> LENGTH: 8
<212> TYPE: PRT
<213> ORGANISM: Homo sapiens

<400> SEQUENCE: 18

Arg Lys Ala Asn Lys Leu Gln Ala
1               5

<210> SEQ ID NO 19
<211> LENGTH: 9
<212> TYPE: PRT
<213> ORGANISM: Homo sapiens

<400> SEQUENCE: 19

Gly Arg Arg Ser Ser Lys Thr Glu Ala
1               5

<210> SEQ ID NO 20
<211> LENGTH: 7
<212> TYPE: PRT
<213> ORGANISM: Homo sapiens

<400> SEQUENCE: 20

Arg Thr Ser Ser Arg Met Gln
1               5

<210> SEQ ID NO 21
<211> LENGTH: 8
<212> TYPE: PRT
<213> ORGANISM: Homo sapiens

<400> SEQUENCE: 21

Gly Arg Lys Arg Ser Arg Met His
1               5

<210> SEQ ID NO 22
<211> LENGTH: 8
<212> TYPE: PRT
<213> ORGANISM: Homo sapiens

<400> SEQUENCE: 22

Gly Arg Lys Arg Ser Lys Thr Gln
1               5

<210> SEQ ID NO 23
<211> LENGTH: 9
<212> TYPE: PRT
```

<213> ORGANISM: Homo sapiens

<400> SEQUENCE: 23

Ser Gly Arg Lys Leu Ala Lys Leu Gln
1               5

<210> SEQ ID NO 24
<211> LENGTH: 8
<212> TYPE: PRT
<213> ORGANISM: Homo sapiens

<400> SEQUENCE: 24

Arg Lys Ser Thr Glu Met Glu Ala
1               5

<210> SEQ ID NO 25
<211> LENGTH: 8
<212> TYPE: PRT
<213> ORGANISM: Homo sapiens

<400> SEQUENCE: 25

Arg Lys Gln Asn Lys Met Glu Ala
1               5

<210> SEQ ID NO 26
<211> LENGTH: 8
<212> TYPE: PRT
<213> ORGANISM: Homo sapiens

<400> SEQUENCE: 26

Arg Arg Ser Ser Arg Leu Gln Ala
1               5

<210> SEQ ID NO 27
<211> LENGTH: 7
<212> TYPE: PRT
<213> ORGANISM: Homo sapiens

<400> SEQUENCE: 27

Arg Thr Ser Ser Arg Met Gln
1               5

<210> SEQ ID NO 28
<211> LENGTH: 177
<212> TYPE: PRT
<213> ORGANISM: Homo sapiens

<400> SEQUENCE: 28

Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
                20                  25                  30

Ser Lys Met Gln Ala Phe Arg Ile Trp Asp Val Asn Gln Lys Thr Phe
            35                  40                  45

Tyr Leu Arg Asn Asn Gln Leu Val Ala Gly Tyr Leu Gln Gly Pro Asn
        50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
                100                 105                 110

-continued

```
Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu

<210> SEQ ID NO 29
<211> LENGTH: 9
<212> TYPE: PRT
<213> ORGANISM: Homo sapiens

<400> SEQUENCE: 29

Arg Ile Trp Asp Val Asn Gln Lys Thr
1               5

<210> SEQ ID NO 30
<211> LENGTH: 10
<212> TYPE: PRT
<213> ORGANISM: Homo sapiens

<400> SEQUENCE: 30

Ala Gly Tyr Leu Gln Gly Pro Asn Val Asn
1               5                   10

<210> SEQ ID NO 31
<211> LENGTH: 14
<212> TYPE: PRT
<213> ORGANISM: Homo sapiens

<400> SEQUENCE: 31

Asn Gln Leu Val Ala Gly Tyr Leu Gln Gly Pro Asn Val Asn
1               5                   10

<210> SEQ ID NO 32
<211> LENGTH: 9
<212> TYPE: PRT
<213> ORGANISM: Homo sapiens

<400> SEQUENCE: 32

Val Thr Lys Phe Tyr Phe Gln Glu Asp
1               5

<210> SEQ ID NO 33
<211> LENGTH: 13
<212> TYPE: PRT
<213> ORGANISM: Homo sapiens

<400> SEQUENCE: 33

Glu Gly Val Met Val Thr Lys Phe Tyr Phe Gln Glu Asp
1               5                   10

<210> SEQ ID NO 34
<211> LENGTH: 12
<212> TYPE: PRT
<213> ORGANISM: Homo sapiens

<400> SEQUENCE: 34

Asn Gln Lys Thr Phe Tyr Leu Arg Asn Asn Gln Leu
```

```
1               5                  10
```

<210> SEQ ID NO 35
<211> LENGTH: 10
<212> TYPE: PRT
<213> ORGANISM: Homo sapiens

<400> SEQUENCE: 35

```
Thr Ala Met Glu Ala Asp Gln Pro Val Ser
1               5                  10
```

<210> SEQ ID NO 36
<211> LENGTH: 10
<212> TYPE: PRT
<213> ORGANISM: Homo sapiens

<400> SEQUENCE: 36

```
Gly Pro Asn Ala Lys Leu Glu Glu Lys Ala
1               5                  10
```

<210> SEQ ID NO 37
<211> LENGTH: 15
<212> TYPE: PRT
<213> ORGANISM: Homo sapiens

<400> SEQUENCE: 37

```
Arg Pro Ser Gly Arg Lys Ser Ser Lys Met Gln Ala Phe Arg Ile
1               5                  10                  15
```

<210> SEQ ID NO 38
<211> LENGTH: 5
<212> TYPE: PRT
<213> ORGANISM: Homo sapiens

<400> SEQUENCE: 38

```
Leu Val Ala Gly Tyr
1               5
```

<210> SEQ ID NO 39
<211> LENGTH: 10
<212> TYPE: PRT
<213> ORGANISM: Homo sapiens

<400> SEQUENCE: 39

```
Lys Gln Ser Ala Gly Lys Arg Ser Met Ser
1               5                  10
```

<210> SEQ ID NO 40
<211> LENGTH: 10
<212> TYPE: PRT
<213> ORGANISM: Homo sapiens

<400> SEQUENCE: 40

```
Lys Ala Ser Gln Lys Gly Met Ser Arg Ser
1               5                  10
```

<210> SEQ ID NO 41
<211> LENGTH: 10
<212> TYPE: PRT
<213> ORGANISM: Homo sapiens

<400> SEQUENCE: 41

```
Ala Gln Met Lys Ser Ser Lys Arg Gly Ser
1               5                  10
```